US010131875B2

(12) United States Patent
Tedder et al.

(10) Patent No.: US 10,131,875 B2
(45) Date of Patent: Nov. 20, 2018

(54) REGULATORY B CELLS AND THEIR USES

(75) Inventors: Thomas F. Tedder, Durham, NC (US); Takashi Matsushita, Ishikawa (JP); Yohei Iwata, Magoya (JP); Koichi Yanaba, Tokyo (JP); Jean-David Bouaziz, Maison-Alfort (FR)

(73) Assignee: Duke University, Durham, NC (US)

( * ) Notice: Subject to any disclaimer, the term of this patent is extended or adjusted under 35 U.S.C. 154(b) by 496 days.

(21) Appl. No.: 13/814,165

(22) PCT Filed: Aug. 4, 2011

(86) PCT No.: PCT/US2011/046643
§ 371 (c)(1),
(2), (4) Date: Feb. 4, 2013

(87) PCT Pub. No.: WO2012/019041
PCT Pub. Date: Feb. 9, 2012

(65) Prior Publication Data
US 2013/0136754 A1 May 30, 2013

Related U.S. Application Data

(60) Provisional application No. 61/370,677, filed on Aug. 4, 2010.

(51) Int. Cl.
*C12N 5/00* (2006.01)
*C12N 5/02* (2006.01)
*C12N 5/0781* (2010.01)
*C07K 16/28* (2006.01)
*A61K 35/17* (2015.01)
*G01N 33/50* (2006.01)
*G01N 33/68* (2006.01)
*A61K 39/00* (2006.01)

(52) U.S. Cl.
CPC ............ *C12N 5/0635* (2013.01); *A61K 35/17* (2013.01); *C07K 16/2803* (2013.01); *G01N 33/5052* (2013.01); *G01N 33/6893* (2013.01); *A61K 2039/505* (2013.01); *G01N 2800/7095* (2013.01); *Y02A 50/388* (2018.01); *Y02A 50/463* (2018.01); *Y02A 50/471* (2018.01); *Y02A 50/484* (2018.01)

(58) Field of Classification Search
CPC .............................. C12N 5/0603; C12N 5/0606
See application file for complete search history.

(56) References Cited

U.S. PATENT DOCUMENTS

| 7,438,907 | B2 | 10/2008 | Schuurman |
| 7,534,772 | B2 | 5/2009 | Weiner |
| 7,695,716 | B2 | 4/2010 | Drachman |
| 2004/0265315 | A1 | 12/2004 | Dingivan |
| 2009/0074711 | A1 | 3/2009 | Glennie |
| 2009/0123467 | A1 | 5/2009 | Bedi et al. |
| 2010/0266680 | A1 | 10/2010 | Andre et al. |
| 2011/0013566 | A1 | 6/2011 | Tedder et al. |
| 2012/0183535 | A1 | 7/2012 | Buggy |
| 2013/0309244 | A1 | 11/2013 | Tedder et al. |
| 2014/0065118 | A1 | 3/2014 | Tedder et al. |

FOREIGN PATENT DOCUMENTS

WO  WO 2009/131712 A2 * 10/2009

OTHER PUBLICATIONS

Anolik, J. H. et al., "New treatments for SLE: Cell-depleting and anti-cytokine therapies," 2005 Best Practice & Research Clinical Rheumatology 19(5):859-878.
Asadullah, K. et al., "Interleukin-10 therapy—Review of a new approach," 2003 Pharmacol. Rev. 55:241-269.
Colgan, S.P. et al., "Ligation of intestinal epithelial CD1d induces bioactive IL-10: Critical role of the cytoplasmic tail in autocrine signaling," 1999 PNAS 96(24):13938-13943.
Dalwadi, H. et al., "B cell developmental requirement for the Gαi2 Gene1," 2003 J. Immunol. 170:1707-1715.
Hernandez, H.J. et al., "In infection with Schistosoma mansoni, B cells are required for T helper type 2 cell responses but not for granuloma formation," 1997 J. Immunology 158:4832-4837.
Jiang, S. et al., "Regulatory T cells and transplantation tolerance," 2006 Human Immunol. 67:765-776.
Klein, U. et al., "Human immunoglobulin (Ig)M+IgD+ peripheral blood B cells expressing the CD27 cell surface antigen carry somatically mutated variable region genes: CD27 as a general marker for somatically mutated (Memory) B Cells," 1998 J. Exp. Med. 188:1679-1689.
Lyons, J.-A. et al., "B cells are critical to induction of experimental allergic encephalomyelitis by protein but not by a short encephalitogenic peptide," 1999 Eur. J. Immunol. 29:3432-3439.
Mann, M. et al., "B cell regulation of CD4+CD25+ T regulatory cells and IL-10 via B7 is essential for recovery from experimental autoimmune encephalomyelitis1," 2007 J. Immunol. 178:3447-3456.
Matsushita, T. et al., "Regulatory B cells (B10 cells) and regulatory T cells have independent roles in controlling EAE initiation and late-phase immunopathogenesis," J. Immunol. 185, 2240-2252 (2010).
Mauri, C. et al., "The 'short' history of regulatory B cells," 2008, Trends in Immunol. 29: 34-40.

(Continued)

*Primary Examiner* — Michail A Belyavskyi
(74) *Attorney, Agent, or Firm* — Andrus Intellectual Property Law, LLP

(57) ABSTRACT

The present invention relates to a distinct B cell subset, B10 cells, that regulate T cell mediated inflammatory responses through the secretion of interleukin-10 (IL-10). The invention also relates to the use of B10 cells in the manipulation of immune and inflammatory responses, and in the treatment of disease. Therapeutic approaches involving adoptive transfer of B10 cells, or expansion of their endogenous levels for controlling autoimmune or inflammatory diseases and conditions are described. Ablation of B10 cells, or inhibition of their IL-10 production can be used to upregulate immunodeficient conditions, ameliorate infectious diseases and/or to treat tumors/cancer. Diagnostic applications are also encompassed.

Figures 1A, 1B:
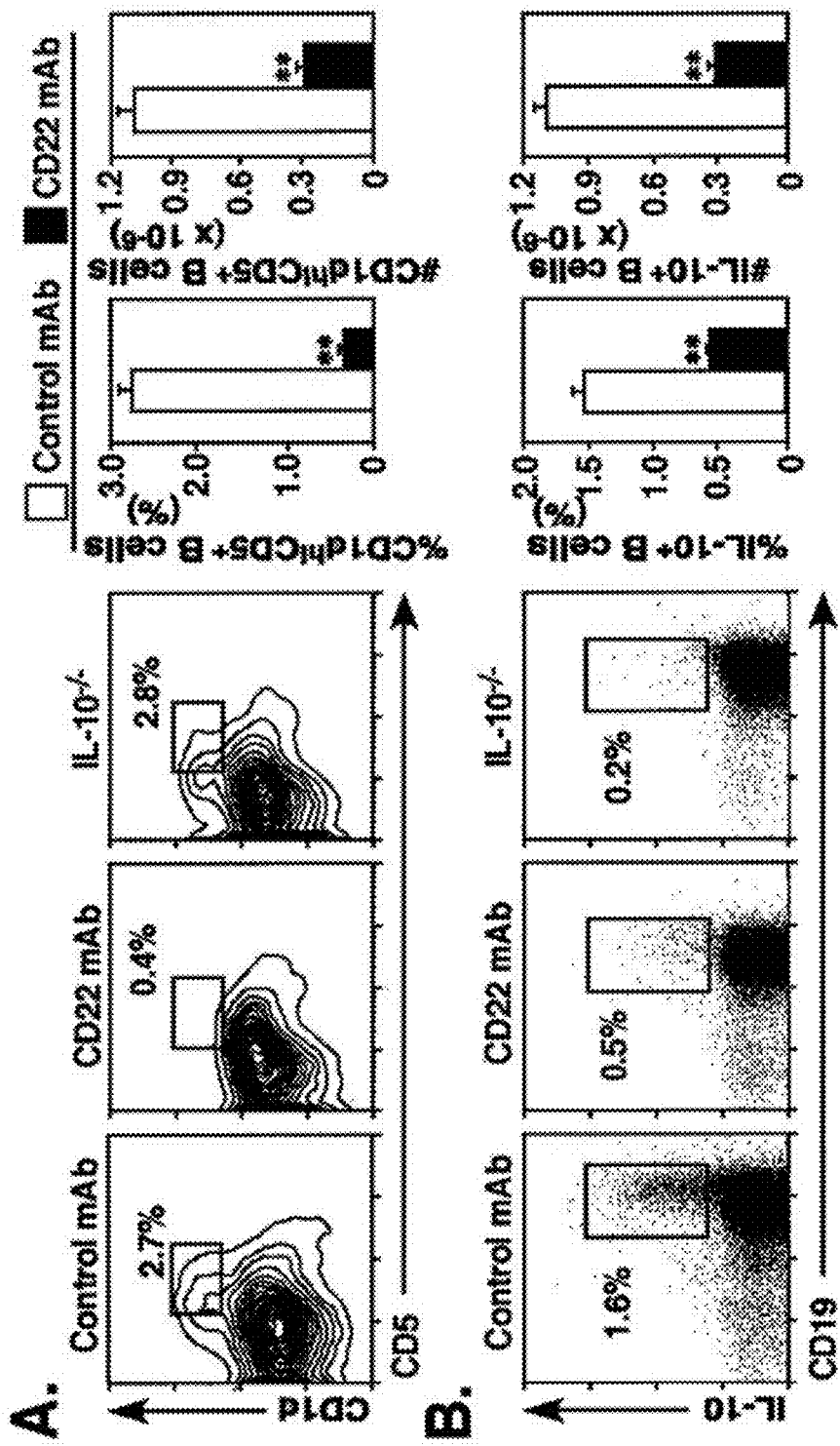

8 Claims, 13 Drawing Sheets
Specification includes a Sequence Listing.

(56) References Cited

OTHER PUBLICATIONS

Mauri C., "Regulation of immunity and autoimmunity by B cells," Curr. Opin. Immunol. 22, 761-767 (2010).
O'Garra, A. et al., "Ly1 B (B-1) cells are the main source of B cell-derived interleukin 10," 1992 Eur. J. Immunol. 22:711-717.
Paciorkowski, N. et al., "Primed Peritoneal B lymphocytes are sufficient to transfer protection against Brugia pahangi infection in mice," 2003 Infection and Immunity 71(3):1370-1378.
Pallier, A. et al., Patients with drug-free long-term graft function display increased numbers of peripheral B cells with a memory and inhibitory phenotype, Kidney International 78:503-513 (2010).
Roncarolo, M.-G. et al., "Regulatory T-cell immunotherapy for tolerance to self antigens and alloangens in humans," 2007 Nature Reviews Immunol. 7:585-598.
Sanz, I. et al., "Phenotypic and functional heterogeneity of human memory B cells," 2008 Sem. Immunol. 20:67-82.
Sonoda, K.-H. et al., "CD1d on antigen-transporting APC and splenic marginal zone B cells promotes NKT cell-dependent tolerance," 2002 Eur. J. Immunol. 32:848-857.
Tangye, S.G. et al., "Identification of functional human splenic memory B cells by expression of CD148 and CD27," 1988 J. Exp. Med. 188:1691-1703.
Velupillai, P. et al., "B-1 cell (CD5+B220+) outgrowth in murine schistosomiasis is genetically restricted and is largely due to activation by polylactosamine sugars," 1997 J. of Immunology 158:338-344.
Watanabe, R. et al., "CD19 expression in B cells is important for suppression of contact hypersensitivity," 2007 American J. of Pathol. 171(2):560-570.
Wei, B. et al., "Mesenteric B cells centrally inhibit CD4+ T cell colitis through interaction with regulatory T cell subsets," 2005 PNAS 102(6):2010-2015.
Wolf, S.D. et al., "Experimental autoimmune encephalomyelitis induction in genetically B cell-deficient mice," 1996 J. Exp. Med. 184:2271-2278.
Xiu, Y. et al., "B lymphocyte depletion by CD20 monoclonal antibody prevents diabetes in nonobese diabetic mice despite isotype-specific differences in FcγR effector funcitons," 2008, J. Immunol. 180:2863-75.
Yanaba, K. et al., "The development and function of regulatory B cells expressing IL-10 (B10 cells) requires antigen receptor diversity and TLR signals," J. Immunol. 182, 7459-7472 (2009).
Yokoyama, S. et al., "Expression of the Blast-1 activation/adhesion molecule and its identification as CD48," 1991 J. Immunol. 146:2192-2200.
Zhang, X. et al., "Type I interferons protect neonates from acute inflammation through interleukin 10-producing B cells," 2007 J. of Experimental Medicine 204(5): 1107-1118.
Bouaziz et al. "Regulatory B cells as inhibitors of immune responses and inflammation," 2008 Immunol. Rev. 224:201-214.
Brummel, R. et al., "Activation of Marginal Zone B Cells from Lupus Mice with Type A(D) CpG-Oligodeoxynucleotides1," 2005 J. Immunol. 174:2429-34.
Brutkiewicz, R.R. et al., "TAP-independent, β2-Microglobulin-dependent surface expression of functional mouse CD1.1,"1995 J. Exp. Med. 182:1913-1919.
Cuss, A.K. et al., "Expansion of functionally immature transitional B cells is associated with human-immunodeficient states characterized by impaired humoral immunity," 2006 J. Immunol. 176:1506-1516).
DiLillo, D. J. et al., "B10 cells and regulatory B cells balance immune responses during inflammation, autoimmunity, and cancer," Ann. N. Y. Acad. Sci. 1183, 38-57 (2010).
Duan, B. et al., "Lupus resistance is associated with marginal zone abnormalities in an NZM murine model," 2007, Lab. Invest. 87:14-28.
Evans, J.G. et al., "Novel suppressive function of transitional 2 B Cells in experimental arthritis," 2007 J. Immunol. 178:7868-78.

Ferguson, T.A. et al., "Regulation of contact hypersensitivity by interleukin 10," (1994) J. Exp. Med. 179:1597-1604.
Fillatreau, S. et al., "B cells regulate autoimmunity by provision of IL-10," Nat. Immunol. 3, 944-950 (2002).
Gray, M. et al., "Apoptotic cells protect mice from autoimmune inflammation by the induction of regulatory B cells," 2007, Proc. Natl. Acad. Sci. USA 104:14080-5.
Haas, K. M. et al., "B-1a and B-1b cells exhibit distinct developmental requirements and have unique functional roles in innate and adaptive immunity to S. pneumoniae," 2005, Immunity 23:7-18.
Haas, K. M. et al., "Protective and pathogenic roles for B cells during systemic autoimmunity in NZB/W F1 mice," J. Immunol. 184, 4789-4800 (2010).
Hasegawa, M. et al., "B-lymphocyte depletion reduces skin fibrosis and autoimmunity in the tight-skin mouse model for systemic sclerosis," 2006, Am. J. Pathol. 169:954-66.
Harris, D.P. et al., "Reciprocal regulation of polarized cytokine production by effector B and T cells," 2000, Nat. Immunol. 1:475-82.
Hayakawa, I. et al., "B-lymphocyte depletion ameliorates Sjogren's syndrome in Id3 knockout mice," 2007, Immunology 122:73-9.
Huggins, J. et al., "CpG DNA activation and plasma-cell differentiation of CD27_ naïve human B cells," Blood 109(4):1611-1619 (2007).
Inoue, S. et al., "Inhibitory effects of B cells on antitumor immunity," 2006 Cancer Res. 66:7741-7747.
Van Krieken, J.H.J.M. et al., "Splenic marginal zone lymphocytes and related cells in the lymph node: A morphologic and immunohistochemical study," 1989 Hum. Pathol. 20:320-325.
Kurosaki, T., "Paradox of B cell-targeted therapies," 2008 J. Clin. Inv. 118(10):3260-3263.
Lampropoulou, V. et al., "TLR-activated B cells suppress T cell-mediated autoimmunity," 2008 J. Immunol. 180:4763-4773.
Levesque, M.C. et al., "B cell-directed therapies for autoimmune disease and correlates of disease response and relapse," 2008 J. Allergy Clin. Immunol. 121:13-21.
Lund, et al., "Cytokine-producing B lymphocytes—key regulators of immunity," 2008 Curr. Op. Immunol. 20(3):332-338.
Makowska, A. et al., "CD1high B cells: A population of mixed origin," 1999 Eur. J. Immunol. 29:3285-3294.
Matsushita, et al., "Inhibitory role of CD19 in the progression of experimental autoimmune encephalomyelitis by regulating cytokine response," 2006 Am. J. Path., 168(3):812-821.
Matsushita, T. et al., "Regulatory B cells inhibit EAE initiation in mice while other B cells promote disease progression,". J. Clin. Invest. 118, 3420-3430 (2008).
Mauri et al., "Prevention of arthritis by interleukin-10-producing B cells," 2003, J. Exp. Med. 197:489-501.
Minard-Colin, V. et al., "Lymphoma depletion during CD20 immunotherapy in mice is mediated by macrophage FcγRI, FcγRIII, and FcγRIV," 2008 Blood 112:1205-1213.
Mizoguchi, A. et al., "Chronic intestinal inflammatory condition generates IL-10-producing regulatory B cell subset characterized by CD1d upregulation," 2002 Immunity 16:219-30.
Mizoguchi, A. et al., "A case for regulatory B cells," 2006, J. Immunol. 176:705-710.
Sato, S. et al., "CD19 regulates B lymphocyte signaling thresholds critical for the development of B-1 lineage cells and autoimmunity," J. Immunol. 157, 4371-4378 (1996).
Schwarz, A. et al., "In vivo effects of interleukin-10 on contact hypersensitivity and delayed-type hypersensitivity reactions," 1994, J. Invest. Dermatol. 103:211-16.
Sims, G.P. et al., "Identification and characterization of circulating human transitional B cells," 2005 Blood 105:4390-4398.
Spencer, N.F. et al., "IL-12 directly stimulates expression of IL-10 by CD5+ B cells and IL-6 by both CD5+ and CD5− B cells: Possible involvement in age-associated cytokine dysregulation," 1997, Int. Immunol. 9:745-54.
Tian, J. et al. Lipopolysaccharide-activated B cells down-regulate Th1 immunity and prevent autoimmune diabetes in nonobese diabetic mice, 2001 J. Immunol. 167:1081-1089.

(56) References Cited

OTHER PUBLICATIONS

Uchida, J. et al, "The innate mononuclear phagocyte network depletes B lymphocytes through Fc receptor-dependent mechanisms during anti-CD20 antibody immunotherapy," 2004 J. Exp. Med. 199:1659-1669.

Yanaba, K. et al., "B cell depletion delays collagen-induced arthritis in mice: Arthritis induction requires synergy between humoral and cell-mediated immunity," 2007, J. Immunol. 179:1369-80.

Yanaba, K. et al., "A regulatory B cell subset with a unique CD1dhiCD5+ phenotype controls T cell-dependent inflammatory responses," Immunity 28, 639-650 (2008).

Becker, P.D. et al., "Generation of human antigen-specific monoclonal IgM antibodies using vaccinated "human immune system" mice," PLoS ONE, 5(10):e13137 (2010).

Blair, P.A. et al., "CD19+CD24hiCD38h cells exhibit regulatory capacity in healthy individuals but are functionally impaired in systemic lupus erythematosus patients," 2010 Immunity 32:129-140.

Cang, S., et al., Novel CD20 monoclonal antibodies for lymphoma therapy, Journal of Hematology and Oncology, 2012, 5:64.

Colliou, N. et al., "Long-Term Remissions of Severe Pemphigus After Rituximab Therapy Are Associated with Prolonged Failure of Desmoglein B Cell Response," Science Translational Medicine 5, 175ra30 (2013).

El Zouhairi, M., et al., Molecularly targeted therapy for metastatic colon cancer: proven treatments and promising new agents, Gastrointest Cancer Res., 2011, 15-21, 4:1.

Fillatreau, S., "Novel regulatory functions for Toll-like receptor-activated B cells during intracellular bacterial infection," Immunol. Rev. 240, 52-71 (2011).

Goodnow, C.C. et al., Altered immunoglobulin expression and functional silencing of self-reactive B lymphocytes in transgenic mice, Nature, 1988, pp. 676-682, vol. 334.

Horikawa, M. et al., "Regulatory B cell production of IL-10 inhibits lymphoma depletion during CD20 immunotherapy in mice," J. Clin. Invest. 121, 4268-4280 (2011).

Kansas, G.S. et al., Transmembrane signals generated through MHC class II, CD19, CD20, CD39 and CD40 antigens induce LFA-1-dependent and -independent adhesion in human B cells through a tyrosine kinase-dependent pathway. J Immunol. 1991; 147: 4094-4102.

Lebien, T. W., and Tedder, T. F., B-lymphocytes: How they develop and function. Blood, 2008, pp. 1570-1579, vol. 112.

Maini, R.N., et. al., How does infliximab work in rheumatoid arthritis, Arthritis Res., 2002, 4 Supp 2:S22-8.

Martin, F. et al., Marginal zone and B1 B cells unite in the early response against T-independent blood-borne particulate antigens, Immunity, 2001, pp. 617-629, vol. 14.

Maseda, D. et al., "Regulatory B10 cells differentiate into antibody-secreting cells after transient IL-10 production in vivo," J. Immunol. 188, 1036-1048 (2012).

Matsushita, T. et al., "Identifying regulatory B cells (B10 cells) that produce IL-10," Methods Mol. Biol. 677, 99-111 (2011).

Mauri, C. et al., Therapeutic activity of agonistic monoclonal antibodies against CD40 in a chronic autoimmune inflammatory process, Nat Med, 2000, pp. 673-679, vol. 6.

Poe, et al., CD22 regulates B lymphocyte function in vivo through both ligand-dependent and ligand-independent mecahnaisms, Nat Immunol, 2004, pp. 1078-1087, vol. 5.

Wehr, C., et al., A new CD21low B cell population in the peripheral blood of patients with SLE, Clin. Immunol., 2004, pp. 161-171, vol. 113.2.

Weitzman, S.A. and Gordon, L.I, et al., Inflammation and cancer: role of phagocyte-generated oxidants in carcinogenesis, Blood, 1990, pp. 655-663, vol. 76.

\* cited by examiner

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic: Sense IL-10 primer

<400> SEQUENCE: 1
ggttgccaag ccttatcgga                                              20
```

```
<210> SEQ ID NO 2
<211> LENGTH: 20
<212> TYPE: DNA
<213> ORGANISM: Artificial Sequence
<220> FEATURE:
<223> OTHER INFORMATION: Synthetic: Antisense IL-10 primer

<400> SEQUENCE: 2
acctgctcca ctgccttgct                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic: sense GAPDH primer

<400> SEQUENCE: 3
ttcaccacca tggagaaggc                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic: antisense GAPDH primer

<400> SEQUENCE: 4
ggcatggact gtggtcatga                                          20

<210> SEQ ID NO 5
<211> LENGTH: 21
<212> TYPE: PRT
<213> ORGANISM: Artificial Sequence
<220> FEATURE:
<223> OTHER INFORMATION: Synthetic: MOG35-55 peptide

<400> SEQUENCE: 5

Met Glu Val Gly Trp Tyr Arg Ser Pro Phe Ser Arg Val Val His Leu
1               5                   10                  15

Tyr Arg Asn Gly Lys
            20

<210> SEQ ID NO 6
<211> LENGTH: 24
<212> TYPE: DNA
<213> ORGANISM: Artificial Sequence
<220> FEATURE:
<223> OTHER INFORMATION: Synthetic: Sense IL-10 primer

<400> SEQUENCE: 6
cttcgagatc tccgagatgc cttc                                     24

<210> SEQ ID NO 7
<211> LENGTH: 24
<212> TYPE: DNA
<213> ORGANISM: Artificial Sequence
<220> FEATURE:
<223> OTHER INFORMATION: Synthetic: Antisense IL-10 primer

<400> SEQUENCE: 7
attcttcacc tgctccacgg cctt                                     24
```

```
<210> SEQ ID NO 8
<211> LENGTH: 24
<212> TYPE: DNA
<213> ORGANISM: Artificial Sequence
<220> FEATURE:
<223> OTHER INFORMATION: Synthetic: sense GAPDH primer

<400> SEQUENCE: 8
gccacccaga agactgtgga tggc                                              24

<210> SEQ ID NO 9
<211> LENGTH: 24
<212> TYPE: DNA
<213> ORGANISM: Artificial Sequence
<220> FEATURE:
<223> OTHER INFORMATION: Synthetic: antisense GAPDH primer

<400> SEQUENCE: 9
catgtaggcc atgaggtcca ccac                                              24
```

REGULATORY B CELLS AND THEIR USES

CROSS-REFERENCE TO RELATED APPLICATIONS

This patent application is a national stage filing under 35 U.S.C. 371 of International Application No. PCT/US2011/046643 filed Aug. 4, 2011, which claims the benefit of priority of U.S. Provisional Patent Application No. 61/370,677, filed Aug. 4, 2010, both of which are incorporated herein by reference in their entirety.

STATEMENT REGARDING FEDERALLY SPONSORED RESEARCH

This invention was made with United States government support awarded by the National Institutes of Health grant number National Cancer Institute grant numbers CA 105001, CA 96547, and National Institute of Allergy and Infectious Disease grant number AI 56363. The United States may have certain rights in this invention.

SEQUENCE LISTING

A Sequence Listing accompanies this application and is incorporated herein by reference in its entirety. The Sequence Listing was filed with the application as a text file on Aug. 4, 2011.

1. INTRODUCTION

The present invention relates to a distinct B cell subset, B10 cells, that regulate T cell mediated inflammatory responses through the secretion of interleukin-10 (IL-10). The invention also relates to the use of B10 cells in the manipulation of immune and inflammatory responses, and in the treatment of disease. Therapeutic approaches involving adoptive transfer of B10 cells, or expansion of their endogenous levels for controlling autoimmune or inflammatory diseases and conditions are described. Ablation of B10 cells, or inhibition of their IL-10 production can be used to upregulate immunodeficient conditions, and/or to treat tumors/cancer. Diagnostic applications are also encompassed.

2. BACKGROUND

The immune response can loosely be divided into two components: the humoral immune response which involves antibody formation, and the cell-mediated immune response which involves the activation of macrophages, natural killer (NK) cells, antigen-specific cytotoxic T-lymphocytes, and the release of various cytokines in response to antigen. Typically, B lymphocytes (B cells) are characterized by their role in antibody production; whereas T lymphocytes (T cells) are characterized by their role in cell-mediated immunity. However, B cells possess additional immune functions, including the production of cytokines, and the ability to function as antigen presenting cells (APCs).

Once generated, immune responses need to be regulated to prevent the responding effector cells from causing harmful effects. Immunoregulation has traditionally been thought of as a function of T cells. Functionally distinct regulatory T cell subsets have been identified and clearly defined. For example, helper T cells that up-regulate the immune response include T helper type 1 (Th1) cells that regulate cell-mediated immune responses, and T helper type 2 (Th2) cells that regulate the humoral immune response. Suppressor T cells crucial for the maintenance of immunological tolerance, currently referred to as T regulatory cells, include IL-10-producing T regulatory 1 (Tr1) cells, and TGF-β1-producing T helper type 3 (Th3) cells. Recent studies of autoimmune conditions gave rise to the notion that B cells may also participate in immunoregulation. However, regulatory B cell subsets have not been clearly defined.

Multiple roles for B cells have been implicated in autoimmune diseases. B cells, a major immune cell population, can play a pathogenic role in acquired immune responses by producing autoantibodies that drive the development of autoimmune diseases. Certain therapies developed for treating autoimmunity are aimed at depleting pathogenic B cells. However, the tools currently available are not specific for the pathogenic B cells and deplete most B cells. For example, B cell depletion in humans using CD20 monoclonal antibody (mAb) can be effective in treating patients with various autoimmune disorders, such as rheumatoid arthritis and lupus (Edwards et al., 2001, Rheumatol. 40:205-11; Edwards et al., 2005, Rheumatol. 44:151-56; El Tal et al., 2006, J. Am. Acad. Dermatol. 55:449-59; Anolik et al., 2004, Arth. Rheum. 50:3580-90; Stasi et al., 2007, Blood 110:2924-30). CD20 is a B cell-specific marker that is first expressed on the cell surface during the pre-B to immature B cell transition, but is lost upon plasma cell differentiation (Tedder & Engel, 1994, Immunol. Today 15:450-54; Uchida et al., 2004, Int. Immunol. 16:119-29). A recent phase II trial using CD20 antibodies indicates clinical efficacy in multiple sclerosis (MS) patients (Hauser et al., 2008, N. Engl. J. Med. 358:676-88). However, the mechanisms underlying the effect of B cell depletion on disease activity remains unknown. On the flip side, B cell depletion may exacerbate disease. Indeed, B cell depletion was recently found to exacerbate ulcerative colitis in human clinical trials (Goetz et al., 2007, Inflamm Bowel Dis. 13:1365-8) and may contribute to the development of psoriasis (Dass et al., 2007, Arthritis Rheum. 56:2715-8).

Over a decade ago, Janeway and colleagues (Wolf et al., 1996, J. Exp. Med. 184: 2271-2278) described studies designed to assess the role of B cells in the course of autoimmune disease by inducing acute experimental autoimmune encephalomyelitis (EAE) in B cell-deficient mice. EAE is an autoimmune disease of the central nervous system (CNS) that models human multiple sclerosis. Results showed that elimination of B cells did not prevent induction of autoimmunity. Instead, the lack of B cells seemed to exacerbate disease outcome, in that the B cell deficient mice did not fully recover as compared to wild-type mice. Thus, while B cells supply the autoantibodies thought to be responsible for disease, these investigators concluded that B cells are not required for activation of disease, and instead, that their presence is required to enhance recovery. More recently, it was reported that B cell IL-10 production correlated with recovery from EAE, a Th1-mediated autoimmune disease (Fillatreau et al., 2002, Nature Immunol. 3: 944-950). IL-10 is an immunoregulatory cytokine produced by many cell populations. IL-10 has been shown to suppress cell-mediated immune and inflammatory responses.

Other recent studies in mouse models indicate that B cells and IL-10 play a protective role in T cell-mediated inflammation, e.g., in Th2-mediated inflammatory bowel disease (Mizoguchi et al., 2002, Immunity 16:216-219), and in contact hypersensitivity (CHS) responses—a cutaneous inflammatory immune reaction that is mediated by T cells in sensitized individuals following subsequent contact with the sensitizing antigen (Enk, 1997, Mol. Med. Today 3:423-8).

In particular, mice with B cells deficient for CD19 expression (CD19$^{-/-}$) have augmented CHS responses (Watanabe et al., 2007, Am. J. Pathol. 171:560-70). IL-10 must be involved in protection since neutralizing IL-10 through mAb treatment enhances CHS responses, while systemic IL-10 administration reduces CHS responses (Ferguson et al., 1994, J. Exp. Med. 179:1597-1604; Schwarz et al., 1994, J. Invest. Dermatol. 103:211-16).

On the basis of these and other studies, it has been proposed that, like their T cell counterparts, B cells can be divided into functionally distinct regulatory subsets capable of inhibiting inflammatory responses and inducing immune tolerance by mechanisms that include IL-10 and TGF-β production, secondary antigen presentation, and interaction with other immune cells either directly or through secreted antibodies. (For reviews on the subject, see Mauri & Ehrenstein, 2007, TRENDS in Immunol. 29: 34-40; and Mizoguchi & Bhan, 2006, J. Immunol. 176:705-710).

However, it remains unclear whether regulatory B cells represent a unique regulatory lineage tasked with maintaining self-tolerance the way that naturally occurring regulatory T cells are. The generation of regulatory B cells has been reported in multiple mouse models of chronic inflammation, although their existence in normal mice remains unknown (Mizoguchi & Bhan, 2006, J. Immunol. 176:705-10). Despite the identification of a regulatory B cell subset generated in these mouse models, no definitive murine phenotype has been established and, in fact, only a general list of cell-surface markers associated with regulatory B cells exists (Mauri & Ehrenstein, 2007, Trends Immun. 29:34-40). Furthermore, the existence of regulatory B cells in humans remains a matter of speculation, and the potential phenotypic markers for human regulatory B cells are unknown (Mauri & Ehrenstein, 2007, Trends Immun. 29:34-40). A role for CD40 in the generation of regulatory B cells and the induction of IL-10 production by these cells has been postulated (Inoue et al., 2006 Cancer Res. 66:7741-7747). Nonetheless, it has yet to be proven whether CD40 can be directly targeted, i.e., with CD40 antibodies, as a means to generate regulatory B cells in vivo (Mauri & Ehrenstein, 2007, Trends Immun. 29:34-40).

Further complicating these issues, during immune responses, IL-10 is also secreted by multiple cell types, including T cells, monocytes, macrophages, mast cells, eosinophils, and keratinocytes, and can suppress both Th1 and Th2 polarization and inhibit antigen presentation and proinflammatory cytokine production by monocytes and macrophages (Asadullah et al., 2003, Pharmacol. Rev. 55:241-69). Clearly, it is unknown whether multiple B cell populations or a novel B cell subset regulates inflammatory responses, whether regulatory B cells produce IL-10 or other cytokines directly, whether regulatory B cells have potent activities in vivo, whether humans possess regulatory B cells, how regulatory B cells can be activated and/or expanded, and the role of regulatory B cells in disease. To advance therapeutic application, subsets of immunoregulatory B cells need to be better defined and their phenotype will need to be more closely correlated with their function in vivo.

3. SUMMARY

The present invention relates to a distinct regulatory B cell subset, termed B10 cells, that regulate T cell-mediated inflammatory and immune responses through secretion of IL-10. The invention also relates to harnessing this B10 cell subset for the manipulation of immune and inflammatory responses in humans and other mammals. Treatments for diseases associated with diminished IL-10 levels, such as inflammatory and autoimmune diseases are described, as well as treatments for diseases associated with elevated IL-10 levels, such as immunosuppression, infectious diseases and cancer.

Cellular compositions enriched for B10 cells, and methods for their preparation are described. B10 cells are characterized by increasing production of IL-10 after stimulation with a CD40 agonist or a TLR (Toll-like Receptor) agonist. For example, without being bound by theory and without limitation, cellular compositions enriched by selection using both CD1d$^{high}$ and CD5 as cellular markers will contain a higher percentage of B10 cells than a population enriched using only one of these markers. Additionally, cellular compositions enriched by selection using both CD24$^{high}$ and CD27 as cellular markers will contain a higher percentage of B10 cells than a population enriched using only one of these markers. Other markers that can be used in selection of B10 cells include, without limitation, CD19, CD20, CD21, CD23, CD25, CD38, CD48, and CD148. These cellular compositions can be expanded and used to treat inflammatory and/or autoimmune conditions or diseases by adoptive transfer.

In an alternative approach, therapeutic regimens designed to expand the endogenous population of B10 cells in subjects in need of such treatment can be used to treat inflammatory and/or autoimmune conditions or diseases. This approach includes methods of treating a disease or condition associated with diminished or insufficient levels of IL-10 or a condition or disease ameliorated by increasing levels of IL-10 or a disease or condition associated with inflammation or immune hyperresponsiveness by administering to a subject in need of such treatment a therapeutically effective amount of an agent that stimulates the expansion of IL-10 producing B10 cells or an agent that increases production of IL-10 by B cells in the subject. The agent may be a TLR agonist or a CD40 agonist. In an alternative approach, the agent may be antibodies that activate and/or stimulate expansion of B10 cells, or increase their production of IL-10.

In an alternative embodiment, methods of treating a disease or condition associated with elevated levels of IL-10 or insufficient or ineffective immune responsiveness by administering to a subject in need of such treatment a therapeutically effective amount of an agent that kills, abrogates, or inhibits the function, localization, or expansion of B10 cells or an agent that inhibits production of IL-10 by B10 cells in the subject. The methods are suitable for treating diseases and/or conditions involving immunosuppression, infectious diseases or cancer by depleting or ablating B10 cells in subjects in need thereof. In this approach, the agent may be antibodies that kill B10 cells, or inhibit their function, proliferation or production of IL-10. In particular, the agent may include antibodies that induce homotypic adhesion and agents that selectively deplete or target B10 cells as opposed to other types of B cells such as follicular B cells.

In yet another embodiment, methods for identifying B10 cells in patients and/or patient samples are described for diagnosing the immune status of affected individuals. The methods include assaying for cells producing IL-10 or capable of producing IL-10 when treated with a CD40 agonist or a TLR agonist. Methods for assessing the number of B10 and B10pro cells are also encompassed.

In still another aspect, methods of generating an antibody that preferentially or selectively depletes B10 cells is described. The method includes selecting an antibody that binds to a marker that is expressed by B10 cells, assaying the antibody for the ability to induce homotypic adhesion of B cells, and assaying the antibody for its ability to deplete the B10 cell population. In some embodiments, the Fc portion of the antibody may be modified so that the mechanism of B10 cell depletion by the antibody is independent of the antibody's Fc region. The antibody may be selected for its ability to deplete the B10 cells by a method that is independent of antibody-dependent cellular cytotoxicity (ADCC), complement-dependent cytotoxicity (CDC) and apoptosis.

In a further aspect, methods of selecting B10 cells is provided. The method includes selecting B lymphocytes in a sample from a subject, stimulating the B cells in vitro with PMA (phorbol 12-myristate 13-acetate) and ionomycin for five hours and selecting IL-10 producing cells. The cells may also be selected by stimulating them for at least 24 hours with a CD40 agonist or a TLR agonist prior to the addition of PMA and ionomycin.

In a still further aspect, methods of inducing an IgG antibody response to an antigen are described. The methods include administering the antigen to a subject and administering an agent that kills or inhibits the function, localization or expansion of B10 cells or inhibits production of IL-10 by B10 cells to the subject. The administration of the agent with the antigen increases the antigen specific IgG antibody production in the subject as compared to a subject administered the antigen alone. The antigen and the agent may be administered together, but need not be.

The invention is based, in part, on the identification of a rare B10 cell subset that controls T cell-mediated immune and inflammatory responses in vivo. The principles of the invention are illustrated in animal models in the studies described in the examples, infra, and resolve previously unexplained contradictions reported in the literature for the role of B cells in disease models such as EAE, arthritis, and inflammatory bowel disease. The examples described infra demonstrate:

a phenotypically unique B cell subset, B10 cells, with potent regulatory activities in vivo;
a reliable method of intracellular cytokine staining that clearly identifies B10 cells;
adoptive transfer of B10 cells has potent IL-10-dependent regulatory functions during inflammation in vivo, which can apply to other T cell-mediated inflammatory or autoimmune diseases;
expansion of B10 cells in human CD19 transgenic mice results in a decreased inflammatory response;
the absence of B10 cells in CD19-deficient mice results in augmented T cell-mediated inflammation; and
the presence of B10 cells in healthy wild type mice (1-2% of spleen B cells) and expansion of the population during contact hypersensitivity responses.

4. DESCRIPTION OF THE FIGURES

FIG. 1. CD22 mAb depletes B10 cells and increases IgG responses. Eight week-old C57BL/6 mice were treated with CD22 mAb (MB22-10; 250 μg/mouse) or control mAb (B1; 250 μg/mouse) 7 days before analysis. (A) Representative CD1d and CD5 expression by $CD19_+$ B cells. Splenocytes were stained with CD1d, CD5, and CD19 mAbs with flow cytometry analysis of viable cells. Results represent one mouse indicating the frequency of $CD1d^{hi}CD5^+$ B cells among total B cells within the indicated gates. Bar graphs indicate mean (±SEM) percentages and numbers of $CD1d^{hi}CD5^+$ B cells in one of two independent experiments with three mice in each group. (B) IL-10 production by B cells. Splenocytes were cultured with LPS (10 PMA (50 ng/ml), ionomycin (500 ng/ml), and monensin (2 μM) for 5 h, then stained with B220 and CD19 mAb to identify B cells, permeabilized, and stained using IL-10 mAb with flow cytometry analysis of viable cells. Representative results demonstrate the frequency of IL-10-producing cells among total $B220_+$ B cells within the indicated gates. Bar graphs indicate mean (±SEM) percentages and numbers of B cells that produced IL-10 in one of two independent experiments with three mice in each group. Leukocytes from $IL-10^{-/-}$ mice served as negative controls to demonstrate specificity and to establish background IL-10 staining levels. (C-D) B10 cells regulate IgG Ab responses. Wild-type mice were given CD22 or control mAb (n=3 per group) on day 0, and immunized with DNP-KLH without adjuvant on days 0 and 21. (C) Serum DNP-specific Abs were quantified by ELISA. (D) The frequency of B cells secreting DNP-specific IgG was determined by ELISPOT analysis of spleen cells harvested on day 28. (A-D) Significant differences between sample means are indicated: *, $p<0.05$; **, $p<0.01$.

FIG. 2. Identification of human blood IL-10-competent B10 and B10pro cells. (A) Frequencies of mouse blood B10 cells after stimulation with PIM, LPS+PIM, or CpG+PIM for 5 h as described (see Yanaba et al., 2008, *Immunity* 28:639-650; Matsushita et al., 2008, *J. Clin. Invest.* 118: 3420-3430; and Yanaba et al., 2009, *J. Immunol.* 182:7459-7472). Representative flow cytometry histograms are shown for one mouse with values from 5 mice shown in the scatter graph. (B) BFA treatment was optimal for visualizing human blood B10 cell numbers. Purified blood mononuclear cells were cultured for 5 h with L+PIB or LPS+PIM as in (A) before immunofluorescence staining and flow cytometry analysis. Bar graph values represent mean (±SEM) B10 cell frequencies from 3 individuals. (C) Representative gating strategy for identifying cytoplasmic $IL-10^+$ human B cells by flow cytometry. Blood mononuclear cells were cultured with LPS+PIB for 5 h and stained for immunofluorescence analysis of viability and cell surface CD19 expression. After membrane permeabilization, the cells were stained with IL-10 mAb. For flow cytometry analysis, single cells were identified by singlet gating using forward scatter area (FSC-A) versus height (FSC-H) plots. The cells outside or below the indicated gate (left panel) were excluded cell doublets. The predominant lymphocyte population within the single cell gate was identified by forward (FSC) and side (SSC-A) light scatter properties. Within the single cell lymphocyte population, the dead cells that were positive for Live/Dead staining were excluded from the analysis. The initial gate for identifying B cells was cell surface CD19 expression. Representative cytoplasmic IL-10 staining by viable, single $CD19^+$ B cells is shown in the dot-plot histograms (right panels). Percentages indicate the frequencies of cytoplasmic $IL-10^+$ B cells within the indicated gates among total $CD19^+$ B cells. Blood mononuclear cells that were cultured with BFA alone before immunofluorescence staining served as negative controls, with background staining similar to that obtained using isotype-matched control mAbs. (D) Representative IL-10 production by human blood B cells from a normal individual with relatively high B10 cell frequencies. B10 cells were identified by cytoplasmic IL-10 expression after in vitro culture with LPS, CpG, and/or PIB as indicated for 5 h. Blood mononuclear cells cultured with BFA alone served as negative controls for background IL-10 staining. Alternatively, B10 cell frequencies were examined after in vitro B10pro cell maturation by stimulation with LPS, CD40L+LPS, CpG, or CD40L+CpG, with PIB added during the final 5 h of 48 h cultures. As negative controls for IL-10 staining, the cells were also stimulated with CD40L+LPS or CD40L+CpG for 48 h, with only BFA added during the final 5 h of culture. Percentages indicate the frequencies of cytoplasmic IL-10$^+$ B cells within the indicated gates among total CD19$^+$ B cells. (E) Frequencies of blood B10 cells in individuals after stimulation with TLR agonists. Cell stimulation and analysis was as described in (C-D). Dots represent results from single individuals after 5 h culture with BFA alone, PIB, or the indicated TLR agonist+PIB. Horizontal bars indicate means. (F) CD40L was optimal for inducing B10+B10pro cell maturation during 48 h in vitro cultures. Purified blood mononuclear cells were cultured with either recombinant CD40L or CD40 mAb, plus LPS for 48 h. PIB was added during the final 5 h of culture. Bar graph values represent mean (±SEM) from 5 different individuals. Similar results were obtained in 2 independent experiments. (G) Representative human blood B10+B10pro cell frequencies after in vitro maturation and stimulation. Blood mononuclear cells were cultured for 48 h with media alone or media containing CD40L, along with the indicated TLR agonists, with PIB added during the last 5 h of each culture. (A, E-G) Significant differences between means of media controls and individual stimuli are indicated: *p<0.05, **p<0.01.

FIG. 3. Human B10 and B10pro cells in cord blood, spleen and tonsil. (A) B10 and B10pro cells in human newborn blood. Mononuclear cells were cultured with the indicated stimuli with PIB added during the last 5 h of culture. Results from a representative cord blood sample are shown along with graphs indicating IL-10$^+$ B cell frequencies in individual newborns. (B) Representative cytoplasmic IL-10 expression by human tissue B cells. B10 and B10pro cells were identified by activation-induced cytoplasmic IL-10 expression as described in FIG. 2C. Cells cultured with BFA alone served as negative controls for background IL-10 staining. (C) Human B10 cell frequencies determined after 5 or 48 h in vitro cultures as described in FIG. 2. Mouse spleen B10 and B10pro cell frequencies are shown for comparison. Dots represent results from single individuals or mice. Significant differences between means of BFA or monensin (Mone) controls and individual stimuli are indicated: *p<0.05, **p<0.01.

FIG. 4. Human B cell stimulation induces IL-10 transcription and secretion in vitro. (A) Time course of Il10 transcript induction. Purified blood CD19$^+$ B cells were cultured with media alone (open bars) or CD40L plus CpG (filled bars) for the times indicated, with Il10 transcripts quantified by real-time RT-PCR analysis. Bar graphs indicate mean IL-10 (±SEM) concentrations of six different individuals. Significant differences between media alone and stimulated B cells are indicated: *p<0.05. Similar results were obtained in 2 independent experiments. (B) Il10 transcript expression correlates with IL-10 secretion. Purified blood B cells were cultured with PMA and ionomycin for 4 h before CD19 staining and secreted IL-10 capture (left panel). Cell surface IL-10$^+$ and IL-10$^-$ B cells were isolated using the indicated gates and subsequently reassessed for IL-10 secretion (right panels) before relative Il10 transcript levels were quantified by real-time RT-PCR analysis. Mean fold-differences (±SEM) for Il10 transcript levels from 3 different individuals are shown, with transcript levels normalized so that the relative mean IL-10$^-$ B cell value is 1.0. Significant differences between means are indicated: *p<0.05. Similar results were obtained in 2 independent experiments. (C) Cell surface signals that regulate cytoplasmic IL-10 expression. Blood B cells were cultured with CpG, CD40L, and anti-IgM Ab (IgM) as indicated for 48 h with PIB added during the final 5 h of culture. The B cells were then stained with CD19 mAb, permeabilized, and stained using IL-10 mAb with flow cytometry analysis. Representative frequencies of IL-10-producing cells within the indicated gates are shown among total CD19$^+$ B cells. Bar graphs indicate mean (±SEM) percentages of B cells that produced IL-10 in 5 different individuals. Similar results were obtained in 2 independent experiments. (D) TLR agonists that induce B10 cell IL-10 secretion. Purified blood CD19$^+$ B cells were cultured with media alone, CD40L, or with TLR agonists and CD40L as indicated for 48 (open bars) or 72 (filled bars) h. IL-10 secreted into the culture supernatant fluid was quantified by ELISA. Bar graphs indicate mean IL-10 (±SEM) concentrations from ≥4 different individuals. Similar results were obtained in 2 independent experiments. (E) LPS and CpG induce mouse blood B10 cell IL-10 secretion. Purified blood B cells were cultured with media alone or with TLR agonists as indicated for 24 (open bars) or 72 (filled bars) h. IL-10 secreted into the culture supernatant fluid was quantified by ELISA. Bar graphs indicate mean IL-10 (±SEM) concentrations from triplicate cultures that represent one of three independent experiments. (D-E) Significant differences between means of cells cultured in media alone and TLR agonists are indicated: *p<0.05, **, p<0.01.

FIG. 5. Representative phenotypes of human and mouse blood and tissue B10 and B10pro cells. (A) Cell surface phenotype of human blood B10 cells. Enriched B cells were cultured with L+PIB for 5 h. (B) Cell surface phenotype of human blood B10+B10pro cells after 48 h stimulation with CD40L+LPS with PIB added during the final 5 h of culture. (E) Cell surface phenotype of mouse blood B10 cells. Purified blood mononuclear cells were cultured with L+PIM for 5 h. (F) Cell surface phenotype of mouse blood B10 plus B10pro cells after 48 h stimulation with CD40 mAb with LPS, PMA, ionomycin, and monensin added during the final 5 h of culture. (C) Cell surface phenotype of human spleen B10 cells. Purified B cells were cultured with CpG+PIB for 5 h. (D) Cell surface phenotype of human spleen B10+ B10pro cells after 48 h stimulation with CD40L+CpG with PIB added during the final 5 h of culture. (G) Cell surface phenotype of mouse spleen B10 cells cultured with L+PIM for 5 h. (H) Cell surface phenotype of mouse spleen B10+ B10pro cells after 48 h stimulation with CD40 mAb with L+PIM added during the final 5 h of culture. (A-H) Cultured cells were stained for viability and cell surface molecule expression, permeabilized, stained with anti-IL-10 mAb, and analyzed by flow cytometry. Representative cell surface molecule expression by IL-10$^+$ (thick line) and IL10$^-$ (thin line) CD19$^+$ B cells from three individuals or >3 mice is shown. Shaded histograms represent isotype-matched control mAb staining.

FIG. 6. Human blood B10 and B10pro cells are predominantly CD24$^{hi}$CD27$^+$. (A) Blood B10 cells were predominantly CD24$^{hi}$CD27$^+$CD48$^{hi}$CD148$^{hi}$. Representative phenotypes of purified blood B cells cultured with CpG+PIB for 5 h before six-color immunofluorescence staining for viability, cell surface molecule expression, and cytoplasmic IL-10. Subsequently, CD24, CD27, CD48, and CD148 expression by IL-10$^+$ (thick line) and IL-10$^-$ (thin line) CD19$^+$ cells was assessed by flow cytometry. (B) Cell surface CD24, CD27, CD38, CD48, or CD148 expression were not affected during IL-10 induction. Representative phenotypes of CD19$^+$ blood B cells cultured with media on ice (thin line) or CpG+PIB (thick line) for 5 h before immunofluorescence staining and flow cytometry analysis as in (A). (A-B) Shaded histograms represent isotype-matched control mAb staining. Results represent those obtained for 3 individuals. (C) Representative distributions of B10 cells within B cell subsets of three individuals as defined by CD24, CD27, IgD/CD38, and IgD/CD27 expression. Purified blood B cells were cultured with LPS+PIB for 5 h before immunofluorescence staining and flow cytometry analysis as in (A). The horizontal and vertical lines on each contour plot are shown for reference, with the lower left quadrants delineating the IgD⁻CD38⁻ and IgD⁻CD27⁻ subsets as determined by control mAb staining, respectively. Results represent those obtained for 5 individuals. (D) Blood B10 cells are predominantly found within the $CD24^{hi}CD27^+$ B cell subset. Purified blood B cells were cultured with LPS+PIB for 5 h before four-color immunofluorescence staining for cell surface CD19, CD24, and CD27 expression and cytoplasmic IL-10 expression, with subsequent flow cytometry analysis. (E) B10pro cells derive from the $CD24^{hi}CD27^+$ B cell subset. Purified blood B cells were stained for CD19, CD24, and CD27 expression and sorted into the $CD24^{hi}CD27^+$ and $CD24^{low}CD27^-$ B cell subsets as indicated by the gates shown. Each purified subset was reanalyzed by flow cytometry to determine purifies, which were always >90%. Subsequently, the purified B cells were cultured with CD40L plus either LPS or CpG for 48 h, with PIB added during the final 5 h of culture. The cultured cells were then stained for cell surface CD19 and intracellular IL-10 expression with the relative percentages of IL-10⁺ B cells within the indicated gates determined. Similar results were obtained in 2 independent experiments. (F) Clonal expansion of IL-10-producing B cells after CpG, but not LPS or CD40L stimulation in vitro. Blood mononuclear cells were labeled with CFSE and cultured with CD40L, and LPS or CPG for 48-96 h, with PIB added for the last 5 h of culture. Histograms (right) represent CFSE expression by the IL-10⁺ (thick line) or IL-10⁻ (thin line) B cell subsets. Results are representative of two independent experiments. (G) IL-10 is predominantly secreted by $CD24^{hi}CD27^+$ B cells. Purified blood B cells were sorted into the $CD24^{hi}CD27^+$ and $CD24^{low}CD27^-$ B cell subsets as in (E) and cultured with the indicated stimuli for 72 h. IL-10 secreted into the culture supernatant fluid was quantified by ELISA. Bar graphs indicate mean IL-10 (±SEM) concentrations from triplicate ELISA determinations. Significant differences between means from $CD24^{hi}CD27^+$ and $CD24^{low}CD27^-$ B cells are indicated: **, $p<0.01$. Significant differences between means from cells cultured in media or with stimuli are indicated: ##, $p<0.01$.

FIG. 7. Blood B10 cell frequencies in patients with autoimmune disease. (A) Representative B cell cytoplasmic IL-10 expression by control (Ctrl) individuals, and SLE, RA, SjS, BD, and MS patients with relatively high B10 cell frequencies after in vitro CpG plus PIB stimulation for 5 h. B10+B10pro cell maturation was induced by 48 h CD40L plus CpG stimulation, with PIB added during the final 5 h of culture. Percentages indicate cytoplasmic IL-10⁺ B cell frequencies within the indicated gates among total CD 19⁺ B cells. (B) IL-10⁺ B cell frequencies in control individuals and patients as represented in (A) with each dot representing single individuals. Horizontal bars indicate group means, the solid horizontal lines indicate means+2 SD (95% confidence interval) for controls, while dashed lines represent means+2 SD for all values. The patients are described in Table 1. (C) Relationship between B10 and B10pro cell frequencies in control individuals and autoimmune patients after in vitro culture with LPS or CpG plus PIB for 5 h. B10+B10pro cells were identified by cytoplasmic IL-10 expression after 48 h stimulation with CD40L plus LPS or CpG with PIB added during the final 5 h of culture. (D) Relative frequencies of B10 cells and B10+B10pro cells identified for control individuals and patients with autoimmune disease are compared after CpG or LPS stimulation as shown in (B) with each dot representing a single individual. (E) Relationship between cytoplasmic IL-10 expression levels and B10pro cell frequencies in control individuals and patients. Each dot representing single individuals after stimulation with CD40L plus CpG, with PIB added during the final 5 h of 48 h cultures. Linear mean fluorescence intensities (MFI) for IL-10⁺ and IL-10⁻ B cells were determined using the gates indicated in (A) with the values shown representing a ratio of IL-10⁺ to IL-10⁻ MFIs. A linear regression line (±95% prediction bands, dashed lines) is shown for reference.

5. DETAILED DESCRIPTION

The present invention relates to a phenotypically distinct B cell subset, B10 cells, that regulate T cell-mediated inflammatory and immune responses through secretion of IL-10. The invention also relates to harnessing B10 cells for the manipulation of the immune and inflammatory responses, and for the treatment of diseases, disorders and conditions associated with altered IL-10 levels, including inflammatory and autoimmune diseases, as well as immunosuppression, infectious diseases and cancer in humans and other mammals.

Cellular compositions enriched for B10 cells, and methods for their preparation are described. The B10 cells are characterized by the ability to produce IL-10, in particular when stimulated with a CD40 or TLR agonist. These cellular compositions can be expanded and used in adoptive transfer therapies to treat conditions associated with diminished IL-10 production or those ameliorated by increased levels of IL-10, e.g., inflammatory and/or autoimmune conditions or diseases. In an alternative approach, therapeutic regimens designed to expand the endogenous population of B10 cells, or increase their production of IL-10 can be used to treat a disease or condition associated with diminished levels of IL-10 or ameliorated by increased levels of IL-10 such as inflammatory, immune hyperresponsive and/or autoimmune conditions or diseases in subjects in need thereof. In this approach, agents capable of activating or stimulating B10 cells are administered to the subject in need of such treatment. The agent may be a TLR agonist or a CD40 agonist. In an alternative approach, the agent may be antibodies that activate and/or stimulate expansion of B10 cells, or increase their production of IL-10. Expansion can be accomplished in vivo (e.g., by direct administration of the agent such as an antibody or receptor agonist) or ex vivo (e.g., by activating and/or expanding the cells obtained from the subject and returning the activated cells to the subject).

Methods of treating a disease or condition associated with elevated levels of IL-10 or insufficient or ineffective immune responsiveness are also provided. These methods include administering a therapeutically effective amount of an agent that kills, abrogates, or inhibits the function, localization, or expansion of B10 cells or an agent that inhibits production of IL-10 by B10 cells to a subject in need of such treatment. The methods are suitable for treating diseases and/or conditions involving immunosuppression, infectious diseases or cancer by depleting or ablating B10 cells in subjects in need thereof. In this approach, the agent may be antibodies that kill B10 cells, or inhibit their function, proliferation or production of IL-10. In particular, the agent may include antibodies that induce homotypic adhesion and agents that selectively deplete or target B10 cells as opposed to other types of B cells such as follicular B cells.

Methods for identifying B10 cells in patients and/or patient samples are described for diagnosing the immune status of affected individuals. The methods include assaying for cells producing IL-10 or capable of producing IL-10 when treated with a CD40 agonist or a TLR agonist. Methods for assessing the number of B10 and B10pro cells in a subject are also encompassed. The immune status of the individual may be useful in predicting the likelihood of contracting a particular disease, such as an autoimmune disease, or in predicting responsiveness to particular diseases or particular therapeutics.

In another embodiment, a method for generating an antibody that preferentially or selectively depletes B10 cells as compared to other subsets of B cells is provided. The method comprises: (i) selecting an antibody that binds to a marker that is expressed by B10 cells including but not limited to, e.g. CD1d, CD5, CD19, CD20, CD21, CD22, CD23, CD24, CD25, CD27, CD38, CD40, CD48, CD72, and CD148; (ii) assaying the antibody for the ability to induce homotypic adhesion of B cells (Kansas G S, Wood G S, Tedder T F. Expression, distribution and biochemistry of human CD39: Role in activation-associated homotypic adhesion of lymphocytes. *J Immunol.* 1991; 146:2235-2244; Kansas G S, Tedder T F. Transmembrane signals generated through MHC class II, CD19, CD20, CD39 and CD40 antigens induce LFA-1-dependent and -independent adhesion in human B cells through a tyrosine kinase-dependent pathway. *J Immunol.* 1991; 147: 4094-4102; Wagner N, Engel P, Vega M, Tedder T F. Ligation of MHC class I and class II molecules leads to heterologous desensitization of signal transduction pathways that regulate homotypic adhesion in human lymphocytes. *J. Immunol.* 1994; 152:5275-5287.); (iii) assaying the antibody for the ability to deplete the B10 cell population. Optionally, the ability of the antibody to deplete or avoid depletion of other B cell subsets may also be assessed. In some embodiments, the Fc portion of the antibody may be modified so that the mechanism of B10 cell depletion by the antibody is independent of the antibody's Fc region. The antibody may be selected for its ability to deplete the B10 cells by a method that is independent of antibody-dependent cellular cytotoxicity (ADCC), complement-dependent cytotoxicity (CDC) and apoptosis.

Methods of selecting B10 cells are also provided. The method includes selecting B lymphocytes in a sample from a subject, stimulating the B cells in vitro with PMA and ionomycin for five hours and selecting IL-10 producing cells. The cells may also be selected by stimulating them for at least 24 hours with a CD40 agonist or a TLR agonist prior to the addition of PMA and ionomycin. The cells may be further selected by screening for markers of B10 cells including but not limited to expression of CD1d, CD5, CD19, CD20, CD21, CD22, CD23, CD24, CD25, CD27, CD38, CD40, CD48, CD72, or CD148 or the relative levels of expression of these markers on the cell surface.

Methods of inducing an IgG antibody response to an antigen, such as in a vaccine or vaccination protocol are described. The methods include administering the antigen to a subject and administering an agent that kills or inhibits the function, localization or expansion of B10 cells or inhibits production of IL-10 by B10 cells to the subject. The administration of the agent with the antigen increases the antigen specific IgG antibody production in the subject as compared to a subject administered the antigen alone. The antigen and the agent may be administered together, but need not be.

5.1 The B10 Cell Subset

The present invention relates to a regulatory subset of the normal B cell population, B10 cells, with the ability to produce IL-10. The invention also relates to therapeutic uses of B10 cells.

The phenotype of B10 cells can be determined by antibody staining and flow cytometry, FACS, using antibodies to phenotypic markers of B10 cells, and techniques known in the art, including but not limited to those described in the examples, infra. See, e.g., Section 6 et seq and U.S. Patent Publication No. 2011/0135666. The invention is based, in part, on the surprising discovery that cellular compositions enriched by selection for B10 cell cellular markers (such as $CD24^{high}CD27^+$ or $CD1d^{high}CD5^+$) will contain a high percentage of IL-10 producing B cells. It is also based on the discovery that these B10 cells can be selected based on their ability to produce IL-10 when stimulated with CD40 agonists or TLR agonists.

The ability of the cells to produce IL-10 can be assessed by measuring IL-10 production in naïve cells and in cultured cells stimulated with LPS (lipopolysaccharide), PMA (phorbol 12-myristate 13-acetate), ionomycin, CpG oligodeoxynucleotides or comparable stimulatory Toll-like receptor (TLR) agonists, or with an agonist of CD40 (e.g., using an antibody to CD40). Production of IL-10 by the cells can be assessed by assaying for IL-10 in the cell culture supernatant. In addition, production of IL-10 can be verified directly by intracellular cytokine staining after additional treatment with Brefeldin A or monensin. Standard immunoassays known in the art can be used for such purpose. Examples of assays for IL-10 production are described in Section 7, infra. While IL-10 is produced at low levels in naïve B10 cells, IL-10 production is increased in response to stimulation.

5.1.1 Cellular Compositions Enriched in B10 Cells

The enriched, isolated and/or purified B10 cell subset composition can comprise anywhere from 0.5% to 50%, at least 55%, at least 60%, at least 65%, at least 70%, at least 75%, at least 80%, at least 85%, at least 90%, at least 95%, at least 99%, or 100% B10 cells (as determined, e.g., by the assays described above). In a preferred embodiment, the enriched/purified B10 cell subset comprises greater than 50% B10 cells. In a more preferred embodiment, the enriched/purified B10 cell subset comprises greater than 75% B10 cells. In a still more preferred embodiment, the enriched/purified B10 cell subset comprises greater than 90% B10 cells. In certain embodiments, the enriched, isolated and/or purified B10 cells have a $CD1d^{high}CD5^+$ phenotype. In certain embodiments, the enriched, isolated and/or purified B10 cells have a $CD24^{hi}CD27^+$ phenotype.

The enriched, isolated and/or purified B10 cells can be obtained from a mammalian subject, including but not limited to rodents, e.g. mice, rats; livestock, e.g. pigs, horses, cows, etc., pets, e.g. dogs, cats; and primates, e.g. humans. In one embodiment, the subject is an animal model of an IL-10 associated disease.

Alternatively, B10 cells may be enriched/purified from any tissue where they reside including, but not limited to, blood (including blood collected by blood banks and cord blood), spleen, bone marrow, lymph nodes, tissues removed and/or exposed during surgical procedures, and tissues obtained via biopsy procedures. Tissues/organs from which the B10 cells are enriched, isolated, and/or purified may be isolated from both living and non-living subjects, wherein the non-living subjects include organ donors.

Methods for the isolation of B10 cells are based on selecting cells having the B10 cell-specific markers. In a specific embodiment, the B10 cell-specific markers comprise $CD1d^{high}$ and CD5. In another specific embodiment, the B10 cell-specific markers comprise $CD24^{high}$ and CD27. In certain embodiments, additional B cell-specific markers can be used for selection including, but not limited to, CD1d, CD19, CD20, CD21, CD23, CD24, CD25, CD38, CD48, and CD148. Several of these markers or combinations of these markers can be used to specifically select B10 cells. In a particular aspect of this embodiment, a B10 cells are enriched/purified by flow cytometry as demonstrated in the examples described in Section 6 and 7, infra. However, a variety of cell separation techniques known in the art can be used, including but not limited to magnetic separation using antibody-coated magnetic beads and/or particles, FACS, affinity chromatography, affinity column separation, "panning" with antibody attached to a solid matrix, density gradient centrifugation, and counter-flow centrifugal elutriation. (See, e.g., Kumar and Lykke, 1984, Pathology, 1:53-62).

According to these embodiments, a cellular composition enriched for B10 cells that has been enriched by selection using both $CD1d^{high}$ and CD5 as cellular markers or $CD24^{high}$ and CD27 as cellular markers will contain a higher percentage of B10 cells than one enriched using only one of these markers. The use of these markers to isolate/enrich/purify B10 cells has several advantages. Using these cell surface markers, as opposed to intracellular IL-10 as a marker, allows for the selection/sorting of the IL-10 producing B cell population without permeabilizing the cells, which would make them therapeutically useless. Once enriched, the cells may be further purified or expanded by stimulating or activating the cells with a CD40 agonist or a TLR agonist. These agonists may be used in combination with PMA and ionomycin.

B10 cells can also be isolated by negatively selecting against cells that are not B10 cells. This can be accomplished by performing a lineage depletion, wherein cells are labeled with antibodies for particular lineages such as the T lineage, the macrophage/monocyte lineage, the dendritic cell lineage, the granulocyte lineages, the erythrocytes lineages, the megakaryocytes lineages, and the like. Cells labeled with one or more lineage specific antibodies can then be removed either by affinity column processing (where the lineage marker positive cells are retained on the column), by affinity magnetic beads or particles (where the lineage marker positive cells are attracted to the separating magnet), by "panning" (where the lineage marker positive cells remain attached to the secondary antibody coated surface), or by complement-mediated lysis (where the lineage marker positive cells are lysed in the presence of complement by virtue of the antibodies bound to their cell surface). Another lineage depletion strategy involves tetrameric complex formation. Cells are isolated using tetrameric anti-human antibody complexes (e.g., complexes specific for multiple markers on multiple cell types that are not markers of B10 cells, given in more detail infra) and magnetic colloid in conjunction with StemSep columns (Stem Cell Technologies, Vancouver, Canada). The cells can then optionally be subjected to centrifugation to separate cells having tetrameric complexes bound thereto from all other cells.

In a certain embodiment, the enriched/purified B10 cells can be stored for a future use. In this regard, the B10 cells can be stored by "cryopreservation." Cryopreservation is a process where cells or whole tissues are preserved by cooling to low sub-zero temperatures, such as 77 K or −196° C. in the presence of a cryoprotectant. At these low temperatures, any biological activity, including the biochemical reactions that would lead to cell death, is effectively stopped. Storage by cryopreservation includes, but is not limited to, storage in liquid nitrogen, storage in freezers maintained at a constant temperature of 0° C., storage in freezers maintained at a constant temperature of −20° C., storage in freezers maintained at a constant temperature of −80° C., and storage in freezers maintained at a constant temperature of lower than −80° C. In one aspect of this embodiment, the cells may be "flash-frozen," e.g., in ethanol/dry ice or in liquid nitrogen prior to storage. In another aspect of this embodiment, the cells can be preserved in medium comprising a cryprotectant including, but not limited to dimethyl sulfoxide (DMSO), glycerol, ethylene glycol, propylene glycol, sucrose, and trehalose. Other methods of storing biological matter are well known to those of skill in the art, such as "hibernation," wherein cells are stored at temperatures above freezing or by preservation of the cells in a "static" state, as described in U.S. patent application publication No. 2007/0078113, incorporated herein by reference in is entirety.

In certain embodiments, B10 cells can be obtained from a subject in need of therapy or suffering from a disease associated with elevated or diminished levels of IL-10. Alternatively, B10 cells can be obtained from a donor, preferably a histocompatibility matched donor. B10 cells may be harvested from the peripheral blood, bone marrow, spleen, or any other organ/tissue in which B10 cells reside in said subject or donor. In a further aspect, the B10 cells may be isolated from a pool of subjects and/or donors, or from pooled blood.

When the population of B10 cells is obtained from a donor distinct from the subject, the donor is preferably syngeneic, but can also be allogeneic, or even xenogeneic, provided the cells obtained are subject-compatible in that they can be introduced into the subject. Allogeneic donor cells are preferably human-leukocyte-antigen (HLA)-compatible, and are typically administered in conjunction with immunosuppressive therapy. To be rendered subject-compatible, xenogeneic cells may be subject to gamma irradiation or PEN110 treatment as described (Fast et al., 2004, Transfusion 44:282-5).

5.1.2. Enrichment of B10 Cells

B10 cells can be enriched by selecting cells having the $CD1d^{high}CD5^+$ surface markers or the $CD24^{high}CD27^+$ surface markers and separating using automated cell sorting such as fluorescence-activated cell sorting (FACS), solid-phase magnetic beads, etc. as demonstrated in examples described in sections 6 and 7 infra. To enhance enrichment, positive selection may be combined with negative selection; i.e., by removing cells having surface markers specific to non-B cells and/or those specific to non-B10 cells. Non-limiting examples of methods of negative selection are described supra. Exemplary surface markers specific to non-B10 cells include CD3, CD4, CD7, CD8, CD15, CD16, CD34, CD56, CD57, CD64, CD94, CD116, CD134, CD157, CD163, CD208, F4/80, Gr-1, and TCR.

The cells may be used to make pharmaceutical compositions. Pharmaceutical compositions comprising the B10 cells described herein and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, oil-based or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified.

5.2 Expansion of the B10 Cell Subset and/or Enhancing their Production of IL-10

In a particular embodiment, expansion of the B10 cell population is achieved by contacting a population of B10 cells with a stimulatory composition sufficient to cause an increase in the number of B10 cells. This may be accomplished by contacting the enriched, isolated and/or purified B10 cell subset with a mitogen, cytokine, growth factor, antibody, CD40 agonist or TLR agonist. The B10 cells are preferably expanded at least 10-fold and preferably at least 50, 100, 200, 300, 500, 800, 1000, 10,000, or 100,000-fold. In a specific aspect of this embodiment, the expanded B10 cell population retains all of the genotypic, phenotypic, and functional characteristics of the original population. In another embodiment, one or more of the characteristics of the B10 cell population is lost or modified following expansion.

Levels of IL-10 produced by the B10 cell subset can be increased by, e.g., administration of agonists to the B cell surface receptor CD40. Non-limiting examples of CD40 agonists include CD40 antibodies and fragments thereof, the CD40 ligand and polypeptide fragments thereof, small molecules, synthetic drugs, peptides (including cyclic peptides), polypeptides, proteins, nucleic acids, synthetic or natural inorganic molecules, mimetic agents, and synthetic or natural organic molecules.

In a certain embodiment, the CD40 agonist is a CD40 antibody. The CD40 antibodies of the invention can be of any form, as disclosed above. Antibodies to CD40 are known in the art (see, e.g., Buhtoiarov et al., 2005, J. Immunol. 174:6013-22; Francisco et al., 2000, Cancer Res. 60:3225-31; Schwulst et al., 2006, 177:557-65, herein incorporated by reference in their entireties).

Levels of IL-10 produced by the B10 cell subset can also be increased by, e.g., administration of agonists to TLRs on the B10 cell surface. In particular embodiments the TLR agonist may be an agonist of TLR1, TLR4, TLR6, TLR7, or TLR9. These agonists include natural ligands of these receptors and non-natural ligands or agonists. Non-limiting examples of TLR agonists include LPS, CpG oligodeoxynucleotides, Pam3CSK4, Pam2CGDPKHPKSF, or Imiquimod and also include variations of these molecules or other small molecules, synthetic drugs, peptides (including cyclic peptides), polypeptides, proteins, nucleic acids, synthetic or natural inorganic molecules, mimetic agents, and synthetic or natural organic molecules.

Expansion of IL-10 production by the B10 cell subset can be advantageously achieved ex vivo, e.g., by isolating the enriched B10 cell population and contacting the cells with a CD40 agonist or a TLR agonist. In an aspect of this embodiment, the cells are contacted with a CD40 agonist or a TLR agonist and relevant antigen(s). In a specific aspect of this embodiment, the cells are contacted with a CD40 agonist, a TLR agonist and relevant antigen(s).

5.3 Ablation of the B10 Cell Subset and/or Inhibiting their Production of IL-10

The B10 cell subset can be ablated by, e.g., engaging a B cell surface markers e.g., CD20 or CD22. Non-limiting examples of compounds capable of engaging B cell surface markers to ablate the B10 cell population include antibodies and fragments thereof, the ligand for the cell surface marker and fragments thereof, ligand mimetics, small molecules, synthetic drugs, peptides (including cyclic peptides), polypeptides, proteins, nucleic acids, synthetic or natural inorganic molecules, mimetic agents, and synthetic or natural organic molecules. Antibodies to B cell surface markers are known in the art (for CD22 see, e.g., Tuscano et al., 2003, Blood 101:3641-7; US 2004/0001828 A1; and US 2007/0264360, for CD20 see, e.g., US 2009/0136516 incorporated by reference herein in their entireties).

Alternatively, a bispecific antibody for CD and CD5 may be used to target the B10 cell subset (these will be referred to herein as bispecific "CD1d/CD5" antibodies). Bispecific antibodies can be prepared from CD1d and CD5 antibodies using techniques that are known in the art (see, e.g., U.S. Pat. Nos. 5,534,254, 5,837,242, 6,492,123; U.S. Patent application publication Nos. 20040058400 and 20030162709, which are all herein incorporated by reference in their entireties). In another embodiment, a bispecific antibody for CD24 and CD27 may be used to target the B10 cell subset.

In order to kill or ablate the B10 cell subset, targeting antibodies (e.g., CD20, CD22, bispecific CD1d/CD5, or bispecific CD24/CD27) of an isotype that mediate ADCC (antibody-dependent and mediated toxicity) or CDC (complement-dependent cytotoxicity) can be used. Of the various human immunoglobulin classes, IgG1, IgG2, IgG3, IgG4 and IgM are known to activate complement. Human IgG1 and IgG3 are known to mediate ADCC. Antibodies to CD20 may be used to deplete B10 cells selectively. The antibodies demonstrated to target the IL-10 producing B10 cell subset were antibodies that were not capable of inducing ADCC, CDC or apoptosis. Instead the effective antibodies were those that induced homotypic adhesion. Thus, antibodies to B cell surface markers with IgG3 or IgG2b Fc regions which do not efficiently engage most Fcy receptors, but induce homotypic adhesion are useful in the methods described herein. Optionally the Fc portion of a known antibody may be modified so that the mechanism of depletion of B10 cells is independent of the antibody's Fc region.

Antibodies targeting the B10 cell subset can be further conjugated to a cytotoxic agent, using methods known in the art (see, e.g., DiJoseph et al., 2004, Clin. Cancer Res. 10:8620-9). This may be preferred when using antibodies or antibody fragments that do not mediate ADCC or CDC. Non-limiting examples of cytotoxic agents include antimetabolites (e.g., cytosine arabinoside, aminopterin, methotrexate, 6-mercaptopurine, 6-thioguanine, cytarabine, and 5-fluorouracil decarbazine); alkylating agents (e.g., mechlorethamine, thiotepa chlorambucil, melphalan, carmustine (BCNU) and lomustine (CCNU), cyclophosphamide, busulfan, dibromomannitol, streptozotocin, mitomycin C, cis-dichlorodiammine-platinum (II) (CDDP), and cisplatin); vinca alkaloid; anthracyclines (e.g., daunorubicin (formerly daunomycin) and doxorubicin); antibiotics (e.g., dactinomycin (formerly actinomycin), bleomycin, mithramycin, and anthramycin (AMC)); calicheamicin; CC-1065 and derivatives thereof; auristatin molecules (e.g., auristatin PHE, bryostatin-1, and dolastatin-10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad, et al., Int. J. Oncol. 15:367-72 (1999), all of which are incorporated by reference herein in their entireties); DNA-repair enzyme inhibitors (e.g., etoposide or topotecan); kinase inhibitors (e.g., compound ST1571, imatinib mesylate (Kantarjian et al., Clin. Cancer Res. 8(7): 2167-76 (2002)); demecolcine; and other cytotoxic agents (e.g., paclitaxel, cytochalasin B, gramicidin D, ethidium bromide, emetine, mitomycin, etoposide, tenoposide, vincristine, vinblastine, colchicine, doxorubicin, daunorubicin, dihydroxy anthracenedione, mitoxantrone, mithramycin, actinomycin D, 1-dehydrotestosterone, glucorticoids, procaine, tetracaine, lidocaine, propranolol, and puromycin and analogs or homologues thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459, all of which are incorporated by reference herein in their entirety); farnesyl transferase inhibitors (e.g., R115777, BMS-214662, and those disclosed by, for example, U.S. Pat. Nos. 6,458,935, 6,451, 812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305, all of which are herein incorporated by reference in their entirety); topoisomerase inhibitors (e.g., camptothecin, irinotecan, SN-38, topotecan, 9-aminocamptothecin, GG211 (GI147211), DX-8951f, IST-622, rubitecan, pyrazoloacridine, XR5000, saintopin, UCE6, UCE1022, TAN-1518A, TAN 1518B, KT6006, KT6528, ED-110, NB-506, ED-110, NB-506, and rebeccamycin); bulgarein; DNA minor groove binders such as Hoechst dye 33342 and Hoechst dye 33258; nitidine; fagaronine; epiberberine; coralyne; beta-lapachone; BC-4-1; antisense oligonucleotides (e.g., those disclosed in the U.S. Pat. Nos. 6,277,832, 5,998,596, 5,885,834, 5,734,033, and 5,618,709, all of which are herein incorporated by reference in their entirety); adenosine deaminase inhibitors (e.g., fludarabine phosphate and 2-chlorodeoxyadenosine); and pharmaceutically acceptable salts, solvates, clathrates, and prodrugs thereof.

In another embodiment, the targeting antibodies, such as a CD20, CD22, bispecific CD1d/CD5, or bispecific CD24/CD27 antibody, can be conjugated to a radioactive metal ion, such as the alpha-emitters $^{211}$astatine, $^{212}$bismuth, $^{213}$bismuth; the beta-emitters $^{131}$iodine, $^{90}$yttrium, $^{177}$lutetium, $^{153}$samarium, and $^{109}$palladium; or macrocyclic chelators useful for conjugating radiometal ions, including but not limited to, $^{131}$indium, $^{131}$L, $^{131}$yttrium, $^{131}$holmium, $^{131}$samarium, to polypeptides or any of those listed supra. In certain embodiments, the macrocyclic chelator is 1,4,7,10-tetraazacyclododecane-N,N',N'',N'''-tetraacetic acid (DATA), which can be attached to the antibody via a linker molecule. Such linker molecules are commonly known in the art and described in Denardo, et al., 1998, Clin Cancer Res 4(10):2483-90; Peterson, et al., 1999, Bioconjug Chem 10(4):553-7; and Zimmerman, et al., 1999, Nucl Med Biol 26(8):943-50, each incorporated by reference herein in their entireties.

In still another embodiment, the targeting antibody, e.g. the CD20, CD22, bispecific CD1d/CD5, or bispecific CD24/CD27 antibody is conjugated to a proteinaceous agent that modifies a given biological response and leads to cytotoxicity. In one embodiment, the antibody is conjugated to a plant-, fungus-, or bacteria-derived toxin. Non-limiting examples of such toxins include A chain toxins, ribosome inactivating proteins, ricin A, deglycosylated ricin A chain, abrin, alpha sarcin, aspergillin, restrictocin, ribonucleases, diphtheria toxin, bacterial endotoxin, saporin toxin, Granzyme B or the lipid A moiety of bacterial endotoxin, cholera toxin, or *Pseudomonas* exotoxin and derivatives and variants thereof.

In another embodiment, an antagonist capable of engaging a B cell surface marker such as CD20, CD22, CD1d or CD5 may be used to ablate the B10 cell population is a synthetic ligand targeted to a B10 cell specific marker, such as that described in Collins et al., 2006, J. Immunol. 5:2994-3003, incorporated herein by reference in its entirety. In one aspect of this embodiment, the synthetic ligand may be further conjugated to a toxin, such as the saporin toxin.

Alternatively, a compound capable of engaging a marker or markers on the B10 cell subset can inhibit the production of IL-10 by the B10 cells. Non-limiting examples of such compounds include antibodies and fragments thereof, small molecules, synthetic drugs, peptides (including cyclic peptides), polypeptides, proteins, nucleic acids, synthetic or natural inorganic molecules, mimetic agents, and synthetic or natural organic molecules. In one embodiment, the compound engages CD22. In an aspect of this embodiment, the compound is a CD22 antibody. In another aspect of this embodiment, the compound engages CD5. In an aspect of this embodiment, the compound is a CD5 antibody. In another aspect of this embodiment, the compound engages CD1d. In an aspect of this embodiment, the compound is a CD1d antibody. In still another aspect of this embodiment, the compound is a bispecific CD1d/CD5 antibody. In another aspect of this embodiment, the compound engages CD24. In an aspect of this embodiment, the compound is a CD24 antibody. In another aspect of this embodiment, the compound engages CD27. In an aspect of this embodiment, the compound is a CD27 antibody. In still another aspect of this embodiment, the compound is a bispecific a CD24/CD27 antibody. In yet another aspect of this embodiment, the compound engages CD19. In an aspect of this embodiment, the compound is a CD19 antibody. In one embodiment, the compound engages CD20. In an aspect of this embodiment, the compound is a CD20 antibody. Alternatively, the compound may bind one or more of CD1d, CD5, CD19, CD20, CD21, CD22, CD24, CD27, CD38, CD40, CD48, CD72, or CD148. In one aspect the compound may be an antibody or a bispecifica antibody directed to one or more of CD1d, CD5, CD19, CD20, CD21, CD22, CD24, CD27, CD38, CD40, CD48, CD72, or CD148.

5.4 Production of Therapeutic Antibodies

Antibodies that target, activate, inhibit and/or kill the B10 cell subset and which can be used in the therapeutic regimens described herein can be made using techniques well known in the art. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Sambrook et al, 2001, Molecular Cloning: A Laboratory Manual, Cold Spring Harbor Laboratory Press, Cold Spring Harbor, N.Y.; Ausubel et al, Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al (eds.) (1999) Genome Analysis: A Laboratory Manual, Cold Spring Harbor Laboratory Press, each of which is incorporated by reference herein in its entirety.

Antibodies for use in the methods of the invention include, but are not limited to, synthetic antibodies, monoclonal antibodies (mAbs), recombinantly produced antibodies, multispecific antibodies (including bi-specific antibodies), human antibodies, humanized antibodies, chimeric antibodies, intrabodies, diabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

In particular, antibodies to be used in the methods of the invention include immunoglobulin molecules and immunologically active portions of immunoglobulin molecules, i.e., molecules that contain an antigen binding site that binds to a CD1d, CD5, CD22, CD24, CD27 or CD40 antigen, or bispecifically to the CD1d and CD5 antigens or the CD24 and CD27 antigens. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule.

Variants and derivatives of antibodies include antibody fragments that retain the ability to specifically bind to an epitope. In certain embodiments, fragments include Fab fragments; Fab'; F(ab')$_2$; a bispecific Fab; a single chain Fab chain comprising a variable region, also known as, a sFv; a disulfide-linked Fv, or dsFv; a camelized VH; a bispecific sFv; a diabody; and a triabody. Derivatives of antibodies also include one or more CDR sequences of an antibody combining site. In certain embodiments, the antibody to be used with the invention comprises a single-chain Fv ("scFv").

The antibodies used in the methods of the invention may be from any animal origin including birds and mammals (e.g., human, murine, donkey, sheep, rabbit, goat, guinea pig, camel, horse, or chicken).

In certain embodiments, the antibodies of the invention are monoclonal antibodies (mAbs). Monoclonal antibodies can be prepared using a wide variety of techniques known in the art including the use of hybridoma, recombinant, and phage display technologies, or a combination thereof. For example, mAbs can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563 681 (Elsevier, N.Y., 1981) (each of which is herein incorporated by reference in their entireties).

Antibodies can also be generated using various phage display methods. Examples of phage display methods that can be used to make the antibodies include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al, 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated by reference herein in its entirety.

In certain embodiments, the antibodies of the invention are chimeric antibodies or single chain antibodies. Techniques developed for the production of "chimeric antibodies" (Morrison et al., 1984, Proc Natl Acad Sci 81:851; Neuberger et al., 1984 Nature 312:604; Takeda et al., 1985, Nature 314:452, each incorporated by reference herein in its entirety) and single chain antibodies (U.S. Pat. No. 4,946,778; Bird, 1988, Science 242:423; Huston et al, 1988, Proc Natl Acad Sci USA 85:5879; and Ward et al, 1989, Nature 334:544, each incorporated by reference herein in its entirety) are well known in the art.

In a certain embodiment, antibodies used in the methods of the invention are humanized antibodies. Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089, each of which is herein incorporated by reference in its entirety), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al, 1994, PNAS 91:969-973, each of which is incorporated by reference herein in its entirety), chain shuffling (U.S. Pat. No. 5,565,332, herein incorporated by reference in its entirety), and techniques disclosed in, e.g., U.S. Pat. No. 6,407,213, U.S. Pat. No. 5,766,886, WO 9317105, Tan et al., 2002, J. Immunol. 169:1119 25, Caldas et al., 2000 Protein Eng. 13(5):353-60, Morea et al., 2000, Methods 20(3):267 79, Baca et al., 1997, J. Biol. Chem. 272(16):10678-84, Roguska et al., 1996, Protein Eng. 9(10):895 904, Couto et al., 1995 Cancer Res. 55 (23 Supp):5973s-5977s, Couto et al., 1995, Cancer Res. 55(8):1717-22, Sandhu J S, 1994, Gene 150(2):409-10, and Pedersen et al., 1994, J. Mol. Biol. 235(3):959-73 U.S. Patent Pub. No. US 2005/0042664 A1 (Feb. 24, 2005), each of which is incorporated by reference herein in its entirety. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Reichmann et al., 1988, Nature 332:323, each of which is incorporated by reference herein in its entirety).

Single domain antibodies can be produced by methods well-known in the art. (See, e.g., Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety).

Further, antibodies that bind to a desired antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438, herein incorporated by reference in their entireties).

Bispecific antibodies can be prepared using techniques that are known in the art. (See, e.g., U.S. Pat. Nos. 5,534,254, 5,837,242, 6,492,123; U.S. patent application publication Nos. 20040058400 and 20030162709, which are all herein incorporated by reference in their entireties).

The present invention contemplates the use of antibodies recombinantly fused or chemically conjugated (including both covalently and non-covalently conjugations) to a polypeptide. Fused or conjugated antibodies of the present invention may be used for ease in purification. For example, the antibodies or fragments thereof for use in the present invention can be fused to marker sequences, such as a peptide to facilitate purification. See e.g., PCT publication WO 93/21232; EP 439,095; Naramura et al., 1994, Immunol Lett 39:91; U.S. Pat. No. 5,474,981; Gillies et al., 1992, Proc Natl Acad Sci USA 89:1428; Fell et al., 1991, J Immunol 146:2446, which are herein incorporated by reference in their entireties.

In certain aspects, the antibodies used in the present invention can be produced intracellularly, in the periplasmic space, or directly secreted into the medium. If the antibodies are produced intracellularly, as a first step, the particulate debris, either host cells or lysed fragments, may be removed, for example, by centrifugation or ultrafiltration.

Exemplary methods for the use of host cells and vectors in the production of antibody can be found in U.S. Pat. Nos. 4,816,567 and 6,331,415 to Cabilly et al., each of which is incorporated by reference herein in its entirety.

5.5 Therapeutic Applications of the B10 Cell Subset to Treat Diseases and Disorders Associated with Diminished IL-10 Levels Diseases or disorders associated with diminished levels of IL-10 and elevated immune/inflammatory responses (particularly inflammatory diseases and autoimmune diseases) can be treated in accordance with the invention using different therapeutic modalities designed to supply the B10 cell subset to an affected subject (e.g., by adoptive transfer/transplant); expand the endogenous B10 cell subset in an affected subject; and/or enhance production of IL-10 by the B10 cell subset (either adoptively transferred cells or the endogenous population) in the affected subject.

In one approach, a cellular composition enriched for the B10 cell subset is administered to a subject in need thereof in amounts effective to increase IL-10. The cellular composition can be obtained from a histocompatibilty matched donor. Alternatively, lymphocytes may be obtained from the subject to be treated, enriched for the B10 cell subset and returned to the patient. In either case the enriched cells can be exposed to an antigen of interest prior to introduction into the subject to further fine-tune the regulation of the immune response. The enriched or selected B10 cells may also be expanded by stimulation in vitro prior to introduction into the subject.

Alternatively, an effective amount of a therapeutic agent capable of stimulating the proliferation of the endogenous B10 cell subset, and/or increasing the amounts of IL-10 produced by the B10 cell subset can be administered to a subject in need thereof in amounts effective to increase IL-10 levels in said subject. These agents may be targeted to the B10 cell cell subset. Such agents include CD40 agonists and TLR agonists.

5.5.1. Diseases and Disorders Associated with Reduced IL-10 Production that can be Treated Using the B10 Cell Subset Diseases and conditions associated with diminished IL-10 levels can be treated in accordance with this aspect of the invention. Decreased levels of IL-10 have been demonstrated in autoimmune and inflammatory diseases including, but not limited to psoriasis (Asadullah et al., 1998, J. Clin. Investig. 101:783-94, Nickoloff et al., 1994, Clin. Immunol. Immunopathol., 73:63-8, Mussi et al. 1994, J. Biol. Regul. Homeostatic Agents), rheumatoid arthritis (Jenkins et al., 1994, Lymphokine Cytokine Res. 13:47-54; Cush et al., 1995, Arthritis Rheum. 38:96-104; Al Janadi et al., 1996, J. Clin. Immunol. 16:198-207), allergic contact dermatitis (Kondo et al., 1994, J. Investig. Dermatol. 103:811-14; Schwarz et al., 1994, J. Investig. Dermatol. 103:211-16), inflammatory bowel disease (Kuhn et al., 1993, Cell 75:263-74; Lindsay and Hodgson, 2001, Aliment. Pharmacol. Ther. 15:1709-16) and multiple sclerosis (Barrat et al., 2002, J. Exp. Med. 195:603-16; Cua et al., 2001, J. Immunol. 166: 602-8; Massey et al., 2002, Vet. Immunol. Immunopathol. 87:357-72; Link and Xiao, 2001, Immunol. Rev. 184:117-28).

Any type of autoimmune disease can be treated in accordance with this method of the invention. Non-limiting examples of autoimmune disorders include: alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteritis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. As described herein, some autoimmune disorders are associated with an inflammatory condition. Thus, there is overlap between what is considered an autoimmune disorder and an inflammatory disorder. Therefore, some autoimmune disorders may also be characterized as inflammatory disorders.

In an aspect of this embodiment, the methods of the invention can be used to treat inflammatory diseases associated with diminished IL-10 levels, but not autoimmune diseases.

In another aspect of this embodiment, the methods of the invention can be used to treat autoimmune diseases associated with diminished IL-10 levels, but not inflammatory diseases.

In yet another aspect of this embodiment, the methods of the invention can be used to treat autoimmune diseases associated with diminished IL-10 levels, wherein the autoimmune disease to be treated is not systemic lupus erythematosus.

Any type of inflammatory disease can be treated in accordance with this method of the invention. Non-limiting examples of inflammatory diseases include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

In still another aspect of this embodiment, the methods of the invention encompass therapies that are aimed at treating diseases associated with a helper T (Th) 1-mediated inflammatory response but not diseases associated with a Th2-mediated inflammatory response.

In an alternative aspect of this embodiment, the methods of the invention encompass therapies that are aimed at treating diseases associated with a Th2-mediated inflammatory response but not diseases associated with a Th1-mediated inflammatory response.

IL-10 is capable of inhibiting ischemia/reperfusion injury (Deng et al., 2001, Kidney Int. 60:2118-28), graft-versus-disease, and transplant-related mortality (Baker et al., 1999, Bone Marrow Transplant 23:1123-9; Holler et al., 2000, Bone Marrow Transplant 25:237-41). As such, one embodiment of the present invention involves treating transplant-associated diseases/conditions by increasing the level of IL-10 in a patient in need thereof.

In another embodiment, the levels of endogenous IL-10 are increased in a subject receiving an organ transplant by administration of a B10 cell subset. In one aspect of this embodiment, the B10 cell population is isolated from the patient themselves, i.e., the subject is the donor. In another aspect of this embodiment, the B10 cell population is isolated from a donor that is not the subject. The donor of the B10 cells may be the same as the organ donor. In another embodiment, the B10 cell population is pooled from several donors.

5.5.2. Therapeutic Modalities

In one embodiment, a subject suffering from an autoimmune disease or an inflammatory disease associated with diminished levels of IL-10 is administered a population of B10 cells. In one aspect of this embodiment, the B10 cell population is isolated from the patient themselves, i.e., the subject is the donor. In another aspect of this embodiment, the B10 cell population is isolated from a donor that is not the subject. In an aspect of this embodiment, the B10 cell population is pooled from several donors. According to this embodiment, administration of a B10 cell population to a subject in need thereof results in an increased level of IL-10 production in the patient sufficient to control, reduce, or eliminate symptoms of the disease being treated.

In one aspect of this embodiment, the therapeutic agent is an antibody, in particular, a CD40 antibody or a CD40 agonist. In other aspects, the therapeutic agent is a small molecule, a polypeptide, DNA, or RNA that interacts with the B cell CD40 receptor. In another embodiment the therapeutic agent is a TLR agonist, such as LPS or CpG. The therapeutic agent may be a different TLR agonist or a small molecule, polypeptide, RNA, dsRNA, or DNA capable of interacting with a TLR receptor.

In another embodiment, a subject suffering from an inflammatory or autoimmune disease associated with diminished levels of IL-10 is treated by administration of a therapeutic agent capable of causing an increase in IL-10 production by the B10 cells in the patient. In a specific aspect of this embodiment, the therapeutic agent targets the B cell CD40 receptor or a TLR. In another aspect of this embodiment, the therapeutic agent is a CD40 antibody a TLR agonist, a small molecule, a polypeptide, DNA, or RNA that is capable of binding, targeting, and or modulating CD40 so as to result in an increase in IL-10 production by the B10 cells in the subject.

An antibody according to these embodiments can be any type of antibody or fragment thereof, as described above. According to this embodiment administration of a CD40 antibody or fragment thereof to a subject with an autoimmune disease or an inflammatory disease associated with diminished levels of IL-10 results in an upregulation of IL-10 production by the endogenous B10 cell population in the subject.

In still another embodiment, a patient receiving a transplant is administered a therapeutic agent capable of increasing endogenous IL-10 production by the B10 cell subset of that patient to increase the patient's tolerance to the transplant. In yet another embodiment, a patient receiving a transplant is administered a B10 cell subset to increase the patient's tolerance to the transplant.

The subject is preferably a mammal such as non-primate (e.g., cows, pigs, horses, cats, dogs, rats, etc.) and a primate (e.g., monkey, such as a cynomolgous monkey and a human). In a preferred embodiment, the subject is a human.

5.5.2.1. B10 Cells as Therapeutic Agents

In one embodiment, adoptive transfer of B10 cells can be effective to suppress a wide variety of diseases, including, but not limited to any of those described above, i.e., autoimmune diseases, inflammatory diseases, or any other disease which may be treated by introduction of a B10 cell population into a subject. Adoptive transfer of B10 cells can further be employed to minimize the immune/inflammatory response associated with transplant of cells and/or tissues.

In an exemplary adoptive cell transfer protocol, a mixed population of B10 cells is initially extracted from a target donor. The B10 cells isolated from the donor may be isolated from any location in the donor in which they reside including, but not limited to, the blood, spleen, lymph nodes, and/or bone marrow of the donor. Depending on the application, the B10 cells may be extracted from a healthy donor; a donor suffering from a disease that is in a period of remission or during active disease; or from the organs, blood, or tissues of a donor that has died. In the case of the latter, the donor is an organ donor. In yet another embodiment, the B10 cells can be obtained from the subject, expanded or activated and returned to the subject.

Harvested lymphocytes may be separated by flow cytometry or other cell separation techniques based on B10 cell markers such as those described herein (e.g., CD1d, CD5, CD24, and CD27), and then transfused to a recipient. Alternatively, the cells may be stored for future use. In one aspect of this embodiment, the donor and the recipient are the same subject. In another aspect of this embodiment, the donor is a subject other than the recipient. In a further aspect of this embodiment, the "donor" comprises multiple donors other than the recipient, wherein the B10 cells from said multiple donors are pooled.

In another embodiment, the B10 cell population obtained from a donor can be expanded, enriched, or made to produce elevated levels of IL-10, as described in sections 5.1 and 5.2, supra, prior to being administered to a recipient.

In the adoptive transfer techniques contemplated herein, wherein the donor is a subject other than the recipient, the recipient and the donor are histocompatible. Histocompatibility is the property of having the same, or mostly the same, alleles of a set of genes called the major histocompatibility complex (MHC). These genes are expressed in most tissues as antigens, to which the immune system makes antibodies. When transplanted cells and/or tissues are rejected by a recipient, the bulk of the immune system response is to the MHC proteins. MHC proteins are involved in the presentation of foreign antigens to T-cells, and receptors on the surface of the T-cell are uniquely suited to recognition of proteins of this type. MHC are highly variable between individuals, and therefore the T-cells from the host recognize the foreign MHC with a very high frequency leading to powerful immune responses that cause rejection of transplanted tissue. As such, the chance of rejection of the B10 cell population by the recipient is minimized.

The amount of B10 cells which will be effective in the treatment and/or suppression of a disease or disorder which may be treated by introduction of a B10 cell population into a subject can be determined by standard clinical techniques. The dosage will depend on the type of disease to be treated, the severity and course of the disease, the purpose of introducing the B10 cell population, previous therapy the recipient has undertaken, the recipient's clinical history, and the discretion of the attending physician. The B10 cell population can be administered in treatment regimes consistent with the disease, e.g., a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Exemplary, non-limiting doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ B10 cells/m$^2$. In a certain embodiment, the dose used in the treatment of human subjects ranges from about $3.8 \times 10^9$ to about $3.8 \times 10^{10}$ B10 cells/m$^2$.

In another aspect of this embodiment, the B10 cells obtained from the donor can be introduced into a recipient at a desired location, so as to specifically target the therapeutic effects of the B10 cell population, i.e., IL-10 production. Such techniques can be accomplished using implantable immune modulation devices, e.g., virtual lymph nodes, such as those described in U.S. patent application publication No. 2003/0118630; WO1999/044583; and U.S. Pat. No. 6,645,500, which are incorporated by reference herein in their entireties. According to this embodiment, a B10 cell population can be isolated from a donor as described above, added to an implantable immune modulation device, and said device then can be inplanted into a recipient at a location where the therapeutic effects of the B10 cell population, i.e., IL-10 production, are needed.

5.5.2.2. Antigen-Specific B10 Cells

In another embodiment, the B10 cell population can be made responsive to a certain antigen involved in a specific disease. In an aspect of this embodiment, the B10 cell population, when sensitized with a certain antigen, will produce therapeutic amounts of IL-10 upon subsequent encounters with the antigen. In an aspect of this embodiment, such an antigen-specific B10 cell population may be used in an adoptive transfer technique, wherein a subject is or has previously been immunized with a certain antigen and the antigen-sensitized B10 cells from said subject are isolated and transplanted to the same or another subject. In still another aspect of this embodiment, a B10 cell population from a subject can be isolated and subsequently can be sensitized with a disease-specific antigen ex vivo or in vitro. The sensitized B10 cell population can then be transplanted into the original or another subject by any method known in the art. In still another aspect of this embodiment, the antigen-specific B10 cell population can be added to an implantable immune modulation device, as described above. According to this embodiment, the implanted B10 cell population will produce strategically localized IL-10 when encountering antigen in the host. In a further aspect, the B10 cell population and a disease-specific antigen can both be placed in an implantable immune modulation device, and said device then can be transplanted into a recipient at a location where the therapeutic effects of the B10 cell population, i.e., IL-10 production, are needed, thus resulting in an amplified response to the disease in vivo.

In another aspect, a certain disease-specific antigen can be administered in conjunction with a CD40 agonist or a TLR agonist. In a certain aspect of this embodiment, the therapeutic agent is an antibody, in particular, a CD40 antibody or LPS or CpG oligodeoxynucleotides. In other aspects, the therapeutic agent is a small molecule, a polypeptide, DNA, or RNA that interacts with the B cell CD40 receptor or TLRs.

Any antigen from any disease, disorder, or condition may be used in accordance with the methods of the invention. Exemplary antigens include but are not limited to bacterial, viral, parasitic, allergens, autoantigens and tumor-associated antigens. If a DNA based vaccine is used the antigen will typically be encoded by a sequence of the administered DNA construct. Alternatively, if the antigen is administered as a conjugate the antigen will typically be a protein comprised in the administered conjugate. Particularly, the antigen can include protein antigens, peptides, whole inactivated organisms, and the like.

Specific examples of antigens that can be used in the invention include antigens from hepatitis A, B, C or D, influenza virus, *Listeria, Clostridium botulinum*, tuberculosis, tularemia, *Variola major* (smallpox), viral hemorrhagic fevers, *Yersinia pestis* (plague), HIV, herpes, pappilloma virus, and other antigens associated with infectious agents. Other antigens include antigens associated with autoimmune conditions, inflammatory conditions, allergy, and asthma. Non-limiting examples of autoimmune diseases and inflammatory diseases are provided, supra.

In an aspect of this embodiment, a B10 cell population sensitized with a disease-specific antigen can be administered alone or in conjunction with a CD40 agonist or TLR, in particular, a CD40 antibody, for use as a therapeutic or prophylactic vaccine for conferring immunity against such disease conditions.

In another embodiment, a B10 cell subset may be sensitized with antigen from a prospective transplant donor, so as to increase the levels of IL-10 production by the B10 cells in a transplant recipient. In an aspect of this embodiment, the increased IL-10 production by the B10 cell subset in the transplant recipient results in a decreased immune/inflammatory response to the transplant in the transplant recipient. The role of B10 cells in transplants is described in section 5.5.2.3, infra.

5.5.2.3. B10 Cells in Organ Transplant Patients

In another embodiment, the levels of endogenous IL-10 are increased in a subject receiving an organ transplant by administration of a B10 cell subset. In one aspect of this embodiment, the B10 cell population is isolated from the patient themselves, the subject is the donor. In another aspect of this embodiment, the B10 cell population is isolated from a donor that is not the subject. In an aspect of this embodiment, the B10 cell population is pooled from several donors. In another aspect of this embodiment, the B10 cell subset is isolated from a subject that has died, wherein said subject is an organ donor. In embodiments wherein the B10 cells are from a donor that is not the subject, the subject and the donor are histocompatible.

In one aspect of this embodiment, the B10 cell subset is administered prior to the transplant. According to this aspect, the therapeutic agent can be administered at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. Administration of the therapeutic agent can be by any method known to those of skill in the art.

In another aspect of this embodiment, the B10 cell subset is administered at the same time as the transplant.

In still another aspect of this embodiment, the B10 cell subset is administered following the transplant.

In a certain aspect, the B10 cell subset is administered before, during, and after the transplant. According to this aspect, when the B10 cell subset is administered after the transplant, it may be administered for at least 12 hours, at least 1 day, at least 2 days, at least 3 days, at least 4 days, at least 5 days, at least 6 days, at least 1 week, at least 2 weeks, at least 3 weeks, at least 4 weeks, least 1 month, or at least 1 year following the transplant or for the duration of the patient's life.

As described in section 5.5.2.2, supra, in one embodiment, a B10 cell subset administered to a patient that is receiving a transplant can be sensitized with antigens specific to the transplanted material. According to this embodiment, the transplant recipient will have a decreased immune/inflammatory response to the transplanted material and, as such, the likelihood of rejection of the transplanted material is minimized.

In another embodiment, the levels of endogenous IL-10 are increased in a subject receiving an organ transplant by administration of a therapeutic agent capable of causing an increase in IL-10 production by the B10 cells in the patient. The therapeutic agent can be administered in viva or ex vivo; i.e., the B10 cell population can be isolated/enriched from the patient, contacted with the therapeutic agent ex vivo, and the "activated" population returned to the patient. In a specific aspect of this embodiment, the therapeutic agent targets the B cell CD40 receptor or a TLR. In another aspect of this embodiment, the therapeutic agent is a CD40 antibody, a small molecule, a polypeptide, DNA, or RNA that is capable of binding, targeting, and or modulating CD40 so as to result in increase in IL-10 production by the B10 cells in the subject.

In one aspect of this embodiment, the therapeutic agent capable of causing an increase in IL-10 production by the B10 cells in the patient is administered prior to the transplant. According to this aspect, the therapeutic agent can be administered at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. Administration of the therapeutic agent can be by any method known to those of skill in the art.

In another aspect of this embodiment, the therapeutic agent capable of causing an increase in IL-10 production by the B10 cells in the patient is administered at the same time as the transplant.

In still another aspect of this embodiment, the therapeutic agent capable of causing an increase in IL-10 production by the B10 cells in the patient is administered following the transplant.

In a certain aspect, the therapeutic agent capable of causing an increase in IL-10 production by the B10 cells in the patient is administered before, during, and after the transplant. According to this aspect, when the therapeutic agent capable of causing an increase in IL-10 production by the B10 cells in the patient is administered after the transplant, it may be administered for at least 12 hours, at least 1 day, at least 2 days, at least 3 days, at least 4 days, at least 5 days, at least 6 days, at least 1 week, at least 2 weeks, at least 3 weeks, at least 4 weeks, least 1 month, or at least 1 year following the transplant or for the duration of the patient's life.

According to these embodiments, administration of a therapeutic agent capable of causing an increase in IL-10 production by the B10 cells in the patient or administration of a B10 cell subset results in a decreased immune response in the patient receiving the transplant, wherein the decreased immune response results in an increased likelihood that the transplant will be accepted, an increased tolerance to the transplant, an increased duration of time in which the transplant is accepted, and/or an increased lifespan in the transplant recipient.

Any type of transplant can be performed according to these methods.

5.6 Therapeutic Targeting of the B Cell Subset to Treat Diseases and Disorders Associated with Enhanced IL-10 Levels In another embodiment, the invention provides methods for treating and/or managing a disease or disorder associated with a decreased/depressed/impaired immune/inflammatory response, particularly cancer or an infectious disease, by administrating to a subject in need thereof a therapeutically or prophylactically effective amount of a therapeutic agent capable of ablating the population of B10 cells and/or the amounts of IL-10 being produced by the B10 cell subset. In another embodiment, the invention provides methods for the treatment of cancer by administrating to a subject in need thereof a therapeutically or prophylactically effective amount of a therapeutic agent capable of ablating the population of B10 cells and/or the amounts of IL-10 being produced by the B10 cell subset.

In an aspect of this embodiment, the therapeutic agent is an antibody that mediates CDC or ADCC and kills target cells, or an immunoconjugate that alters the function of or kills target cells is used. In particular, a CD22 mAb that kills or inhibits the proliferation of the B10 cell subset can be used. Alternatively, a CD1d, a CD5, a CD24, or a CD27 antibody or a bispecific a CD1d/CD5 or a CD24/CD27 antibody can be used.

In another aspect of this embodiment, the therapeutic agent is an antibody that does not utilize CDC or ADCC to kill the target cells. In another aspect, the antibody does not kill the target cells by apoptosis.

In another aspect of this embodiment, the therapeutic agent is an antibody that does not utilize CDC, ADCC, or apoptosis as the primary mechanism for killing target cells, i.e., the majority of target cells are killed by a mechanism that is CDC-, ADCC-, and apoptosis-independent.

In another aspect of this embodiment, the therapeutic agent is a small molecule, a polypeptide, DNA, or RNA that interacts with the B cell CD22 receptor or with CD1d, CD5, CD20, CD24, or CD27.

The subject is preferably a mammal such as non-primate (e.g., cows, pigs, horses, cats, dogs, rats, etc.) and a primate (e.g., monkey, such as a cynomolgous monkey and a human). In a preferred embodiment, the subject is a human.

5.6.1 Diseases and Disorders Associated with Increased IL-10 Production

IL-10 has been shown to promote tumor growth and overexpression of IL-10 has been demonstrated in certain cancers (Matsuda et al., 1994, J. Exp. Med. 180:2371-6; Salazar-Onfray et al., 1997, J. Immunol. 159:3195-3202; Hagenbaugh et al. 1997, J. Exp. Med. 185:2101-110; Kruger-Kraskagakes et al. 1994, Br. J. Cancer 70:1182-5, Dummer et al., 1996, Int. J. Cancer 66:607-10; Kim et al., 1995, J. Immunol. 155:2240-47; Blay et al., 1993, Blood 82:2169-74; Asadullah et al., 2000, Exp. Dermatol. 9:71-6). As such, one embodiment of the present invention involves treating cancer by decreasing the level of IL-10 in a patient in need thereof by ablation of the B10 cell subset and/or reducing the amount of IL-10 produced by the B10 cell subset.

Any type of cancer can be treated in accordance with this method of the invention. Non-limiting examples of cancers include: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al, 1985, Medicine, 2d Ed., J.B. Lippincott Co., Philadelphia and Murphy, 1997, Informed Decisions: The Complete Book of Cancer Diagnosis, Treatment, and Recovery, Viking Penguin, Penguin Books U.S.A., Inc., United States of America, incorporated by reference herein in its entirety).

Increased levels of IL-10 have been demonstrated in certain autoimmune and inflammatory diseases including, but not limited to systemic lupus erythematosus (Park et al., 1998, Clin. Exp. Rheumatol. 16:283-88; Llorente et al., 1995, J. Exp. Med. 181:839-44), systemic sclerosis (Hasegawa et al., 1997, J. Rheumatol. 24:328-32), Bullous Pemphigoid (Schmidt et al., 1996, Arch. Dermatol. Res. 228: 353-7; Giacalone et al., 1998, Exp. Dermatol. 7:157-61), and atopic dermatitis (Ohmen et al., 1995, J. Immunol. 154: 1956-63; Asadullah et al., 1996, J. Investig. Dermatol. 197:833-7). As such, one embodiment of the present invention involves treating an autoimmune or inflammatory by decreasing the level of IL-10 in a patient in need thereof by ablation of the B10 cell subset and/or reducing the amount of IL-10 produced by the B10 cell subset.

Any type of autoimmune disease that is accompanied by increased IL-10 production can be treated in accordance with this method of the invention. A non-limiting list of autoimmune disorders is provided above.

Any type of inflammatory disease that is accompanied by increased IL-10 production can be treated in accordance with this method of the invention. A non-limiting list of inflammatory diseases is provided above.

In an aspect of this embodiment, the methods of the invention can be used to treat inflammatory diseases associated with diminished IL-10 levels, but not autoimmune diseases.

In another aspect of this embodiment, the methods of the invention can be used to treat autoimmune diseases associated with diminished IL-10 levels, but not inflammatory diseases.

In yet another aspect of this embodiment, the methods of the invention can be used to treat autoimmune diseases associated with diminished IL-10 levels, wherein the autoimmune disease to be treated is not systemic lupus erythematosus.

In still another aspect of this embodiment, the methods of the invention encompass therapies that are aimed at treating diseases associated with a helper T (Th) 1-mediated inflammatory response but not diseases associated with a Th2-mediated inflammatory response.

In an alternative aspect of this embodiment, the methods of the invention encompass therapies that are aimed at treating diseases associated with a Th2-mediated inflammatory response but not diseases associated with a Th1-mediated inflammatory response.

IL-10 has also been shown to be associated with the pathogenesis or ineffective immune response to many infectious diseases as well. The infectious diseases may be mediated by viruses, bacteria, yeast, parasites or prions. A non-limiting list of infectious diseases that may benefit from decreasing or inhibiting IL-10 production by the B10 cell subset includes, but is not limited to Diphtheria, Tetanus, Pertussis, *Haemophilus influenzae* type b, Anthrax, Measles, Rubella, Mumps, Botulism, Chickenpox, Cholera, Hepatitis B, Influenza, Hepatitis A, Hepatitis C, Rabies, Polio, Japanese Encephalitis Virus, Meningitis, Typhoid, Pneumonia, Rocky Mountain Spotted Fever, Lyme Disease, Smallpox, Tetanus, *Mycobacterium*, Malaria, HIV/AIDS, RSV, Herpesviruses, and Yellow Fever.

5.6.2 Therapies

In one embodiment, a subject suffering from cancer who has elevated levels of IL-10 is treated by administration of a therapeutic agent capable of ablating the population of B10 cells in the patient and/or reducing the amount of IL-10 produced by the B10 cell population. In a specific aspect of this embodiment, the therapeutic agent targets the B cell CD22 receptor. In another aspect of this embodiment, the therapeutic agent is a CD22 antibody, a small molecule, a polypeptide, DNA, or RNA that is capable of binding, targeting, and or modulating CD22 so as to result in ablation of the B10 cell subset. In a specific aspect of this embodiment, the therapeutic agent targets the B cell CD20 receptor. In another aspect of this embodiment, the therapeutic agent is a CD20 antibody, a small molecule, a polypeptide, DNA, or RNA that is capable of binding, targeting, and or modulating CD20 so as to result in ablation of the B10 cell subset.

In another embodiment, a subject suffering from an immune deficiency disease associated with elevated levels of IL-10 is treated by administration of a therapeutic agent capable of ablating the population of B10 cells in the patient and thereby reducing the amount of IL-10 produced by the B10 cell population. In a specific aspect of this embodiment, the therapeutic agent targets the B cell CD22 receptor. In another aspect of this embodiment, the therapeutic agent is a CD22 antibody, a small molecule, a polypeptide, DNA, or RNA that is capable of binding, targeting, and or modulating CD22 so as to result in ablation of the B10 cell subset.

In an alternative embodiment, a subject suffering from cancer or an immune deficiency disease associated with elevated levels of IL-10 is treated by administration of a CD1d, CD5, CD24, CD27 antibody or a bispecific CD1d/CD5 or CD24/CD27 antibody capable of ablating the population of B10 cells in the patient and thereby reducing the amount of IL-10 produced.

In order to kill or ablate the B10 cell subset, targeting antibodies of an isotype that mediate ADCC (antibody-dependent and mediated toxicity) or CDC (complement-dependent cytotoxicity) can be used. Of the various human immunoglobulin classes, IgG1, IgG2, IgG3, IgG4 and IgM are known to activate complement. Human IgG1 and IgG3 are known to mediate ADCC. Antibodies to CD20 may be used to deplete B10 cells selectively. The antibodies demonstrated to target the IL-10 producing B10 cell subset were antibodies that were not capable of inducing ADCC, CDC or apoptosis. Instead the effective antibodies were those that induced homotypic adhesion. Thus, antibodies to B cell surface markers with IgG3 or IgG2b Fc regions which do not efficiently engage most Fcy receptors, but induce homotypic adhesion are useful in the methods described herein. Optionally the Fc portion of a known antibody may be modified so that the mechanism of depletion of B10 cells is independent of the antibody's Fc region.

Antibodies targeting the B10 cell subset can be further conjugated to a cytotoxic agent, using methods known in the art (see, e.g., DiJoseph et al., 2004, Clin. Cancer Res. 10:8620-9). This may be preferred when using antibodies or antibody fragments that do not mediate ADCC or CDC. Non-limiting examples of cytotoxic agents include antimetabolites (e.g., cytosine arabinoside, aminopterin, methotrexate, 6-mercaptopurine, 6-thioguanine, cytarabine, and 5-fluorouracil decarbazine); alkylating agents (e.g., mechlorethamine, thiotepa chlorambucil, melphalan, carmustine (BCNU) and lomustine (CCNU), cyclophosphamide, busulfan, dibromomannitol, streptozotocin, mitomycin C, cis-dichlorodiammine-platinum (II) (CDDP), and cisplatin); vinca alkaloid; anthracyclines (e.g., daunorubicin (formerly daunomycin) and doxorubicin); antibiotics (e.g., dactinomycin (formerly actinomycin), bleomycin, mithramycin, and anthramycin (AMC)); calicheamicin; CC-1065 and derivatives thereof; auristatin molecules (e.g., auristatin PHE, bryostatin-1, and dolastatin-10; see Woyke et al., Antimicrob. Agents Chemother 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad, et al., Int. J. Oncol. 15:367-72 (1999), all of which are incorporated by reference herein in their entireties); DNA-repair enzyme inhibitors (e.g., etoposide or topotecan); kinase inhibitors (e.g., compound ST1571, imatinib mesylate (Kantarjian et al., Clin. Cancer Res. 8(7): 2167-76 (2002)); demecolcine; and other cytotoxic agents (e.g., paclitaxel, cytochalasin B, gramicidin D, ethidium bromide, emetine, mitomycin, etoposide, tenoposide, vincristine, vinblastine, colchicine, doxorubicin, daunorubicin, dihydroxy anthracenedione, mitoxantrone, mithramycin, actinomycin D, 1-dehydrotestosterone, glucorticoids, procaine, tetracaine, lidocaine, propranolol, and puromycin and analogs or homologues thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459, all of which are incorporated by reference herein in their entirety); farnesyl transferase inhibitors (e.g., R115777, BMS-214662, and those disclosed by, for example, U.S. Pat. Nos. 6,458,935, 6,451, 812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305, all of which are herein incorporated by reference in their entirety); topoisomerase inhibitors (e.g., camptothecin, irinotecan, SN-38, topotecan, 9-aminocamptothecin, GG211 (GI147211), DX-8951f, IST-622, rubitecan, pyrazoloacridine, XR5000, saintopin, UCE6, UCE1022, TAN-1518A, TAN 1518B, KT6006, KT6528, ED-110, N13-506, ED-110, NB-506, and rebeccamycin); bulgarein; DNA minor groove binders such as Hoechst dye 33342 and Hoechst dye 33258; nitidine; fagaronine; epiberberine; coralyne; beta-lapachone; BC-4-1; antisense oligonucleotides (e.g., those disclosed in the U.S. Pat. Nos. 6,277,832, 5,998,596, 5,885,834, 5,734,033, and 5,618,709, all of which are herein incorporated by reference in their entirety); adenosine deaminase inhibitors (e.g., fludarabine phosphate and 2-chlorodeoxyadenosine); and pharmaceutically acceptable salts, solvates, clathrates, and prodrugs thereof.

In another embodiment, the targeting antibody, such as a CD20, CD22, bispecific CD1d/CD5, or bispecific CD24/CD27 antibody, can be conjugated to a radioactive metal ion, such as the alpha-emitters $^{211}$astatine, $^{212}$bismuth, $^{213}$bismuth; the beta-emitters $^{131}$iodine, $^{90}$yttrium, $^{177}$lutetium, $^{153}$samarium, and $^{109}$palladium; or macrocyclic chelators useful for conjugating radiometal ions, including but not limited to, $^{131}$indium, $^{131}$L, $^{137}$yttrium, $^{131}$holmium, $^{131}$samarium, to polypeptides or any of those listed supra. In certain embodiments, the macrocyclic chelator is 1,4,7,10-tetraazacyclododecane-N,N',N'',N'''-tetraacetic acid (DOTA), which can be attached to the antibody via a linker molecule. Such linker molecules are commonly known in the art and described in Denardo, et al., 1998, Clin Cancer Res 4(10):2483-90; Peterson, et al., 1999, Bioconjug Chem 10(4):553-7; and Zimmerman, et al., 1999, Nucl Med Biol 26(8):943-50, each incorporated by reference herein in their entireties.

In still another embodiment, the targeting antibody, such as a CD20, CD22, bispecific CD1d/CD5, or bispecific CD24/CD27 antibody, can be conjugated to a proteinaceous agent that modifies a given biological response and leads to cytotoxicity. In one embodiment, the antibody is conjugated to a plant-, fungus-, or bacteria-derived toxin. Non-limiting examples of such toxins include A chain toxins, ribosome inactivating proteins, ricin A, deglycosylated ricin A chain, abrin, alpha sarcin, aspergillin, restrictocin, ribonucleases, diphtheria toxin, bacterial endotoxin, saporin toxin, Granzyme B or the lipid A moiety of bacterial endotoxin, cholera toxin, or *Pseudomonas* exotoxin and derivatives and variants thereof.

In another embodiment, an antagonist capable of engaging a B10 cell specific surface marker to ablate the B10 cell population is a synthetic ligand specific for the marker, such as that described in Collins et al., 2006, J. Immunol. 5:2994-3003, incorporated herein by reference in its entirety. In one aspect of this embodiment, the synthetic ligand may be further conjugated to a toxin, such as the saporin toxin.

In an alternative embodiment, a subject suffering from cancer, an infectious disease or an immune deficiency disease associated with elevated levels of IL-10 is treated by administration of a compound capable of engaging a marker or markers on the B10 cell subset that can inhibit the production of IL-10 by the B10 cells. Non-limiting examples of such compounds include antibodies and fragments thereof, small molecules, synthetic drugs, peptides (including cyclic peptides), polypeptides, proteins, nucleic acids, synthetic or natural inorganic molecules, mimetic agents, and synthetic or natural organic molecules. In one embodiment, the compound engages CD22. In an aspect of this embodiment, the compound is a CD22 antibody.

In another aspect of this embodiment, the compound engages CD5. In an aspect of this embodiment, the compound is a CD5 antibody. In another aspect of this embodiment, the compound engages CD1d. In an aspect of this embodiment, the compound is a CD1d antibody. In still another aspect of this embodiment, the compound is a bispecific CD1d/CD5 antibody. In another aspect of this embodiment, the compound engages CD24. In an aspect of this embodiment, the compound is a CD24 antibody. In another aspect of this embodiment, the compound engages CD27. In an aspect of this embodiment, the compound is a CD27 antibody. In still another aspect of this embodiment, the compound is a bispecific CD24/CD27 antibody. In yet another aspect of this embodiment, the compound engages CD19. In an aspect of this embodiment, the compound is a CD19 antibody.

An antibody according to these embodiments can be any type of antibody or fragment thereof, as described above. According to this embodiment, administration of an antibody that targets the B10 cell population or fragment thereof, including a CD22 antibody or fragment thereof to a patient with cancer, an infectious disease, an autoimmune disease, or an inflammatory disease associated with increased levels of IL-10 results in a downregulation of IL-10 production by the B10 cell population in the patient.

In another embodiment, a patient suffering from cancer, an infectious disease or an immune deficiency disease associated with elevated levels of IL-10 is treated by administration of an antibody that binds to a B cell marker and selectively depletes the B10 cell population in the patient. According to this embodiment, the B cell marker can be any antigen that is presently known or subsequently determined to be expressed by B10 cells including, e.g. CD1d, CD5, CD19, CD20, CD21, CD23, CD24, CD25, CD27, CD3, CD48, and CD148. In one aspect of this embodiment, the antibody that binds to a B cell marker and selectively depletes the B10 cell population in the patient does not cause depletion of the B10 cell population by an antibody-dependent cell-mediated cytotoxicity (ADCC) mechanism, by complement-dependent cytotoxicity (CDC), or by apoptosis. In another aspect, depletion of the B10 cell population by the antibody is independent of the antibody's Fc region. In another aspect of this embodiment, the antibody that binds to a B cell marker and selectively depletes the B10 cell population depletes splenic Marginal Zone B cells but does not substantially deplete splenic Follicular B cells. In a specific aspect, the antibody that binds to a B cell marker and selectively depletes the B10 cell population is an IgG2b or an IgG3 isotype.

In another embodiment, the antibody for use in treating a patient suffering from cancer or an immune deficiency disease associated with elevated levels of IL-10 that binds to a B cell marker and selectively depletes the B10 cell population comprises a human IgG isotype or Fc region that does not activate complement or lead to ADCC or kill cells by inducing apoptosis. Any human isotype or Fc region that does not activate complement or lead to ADCC or kill cells by inducing apoptosis can be used in accordance with this embodiment. In one aspect, the isotype is IgG4.

In a specific embodiment, a patient suffering from cancer is treated by administration of a CD20 antibody that selectively depletes the B10 cell population in the patient, wherein the depletion of the B10 cell population by the CD20 antibody is not caused by ADCC, CDC, or apoptosis. In another aspect, depletion of the B10 cell population by the antibody is independent of the antibody's Fc region. In an aspect of this embodiment, the CD20 antibody depletes splenic Marginal Zone B cells but does not substantially deplete splenic Follicular B cells. In a specific aspect, the CD20 is an IgG2b or an IgG3 isotype. In another aspect, the CD20 antibody comprises a human IgG isotype or Fc region that does not activate complement or lead to ADCC or induce apoptosis. Any human isotype or Fc region that does not activate complement or lead to ADCC or kill cells by inducing apoptosis can be used in accordance with this embodiment. In one aspect, the isotype is IgG4.

In certain embodiments, the B10 cell population is depleted by at least 1%, at least 1% to 5%, at least 1% to 10%, at least 1% to 25%, at least 1% to 50%, at least 55%, at least 60%, at least 65%, at least 70%, at least 75%, at least 80%, at least 85%, at least 90%, at least 95%, at least 99%, or by 100% as measured by assays known to one of skill in the art including those described in the Examples infra, e.g., immunofluorescence staining with flow cytometry analysis, ELISA assay for IL-10 secretion, or ELISpot analysis for determining numbers of IL-10-secreting cells.

In certain embodiments, the antibodies described herein are administered alone. In other embodiments, the antibodies described herein are administered to patients as a front-line therapy. In other embodiments, the antibodies described herein are administered to patients as a secondary therapy. In certain embodiments, the patient has not previously been treated for the cancer, infectious disease or the immune deficiency disease. In other embodiments, the patient is undergoing or has undergone treatment for the cancer or the immune deficiency disease. In yet other embodiments, the patient has failed treatment for the cancer or the immune deficiency disease.

In certain embodiments, the antibodies described herein are administered in combination with other therapeutic agents. Any therapy that is useful, has been used, or is currently being used for the prevention, treatment, and/or management of cancer, infectious disease or an immune deficiency disease can be used in compositions and methods of the invention. Such therapies include, but are not limited to, peptides, polypeptides, antibodies, conjugates, nucleic acid molecules, small molecules, mimetic agents, synthetic drugs, inorganic molecules, and organic molecules.

Non-limiting examples of cancer therapies include chemotherapy, radiation therapy, hormonal therapy, surgery, small molecule therapy, anti-angiogenic therapy, differentiation therapy, epigenetic therapy, radioimmunotherapy, targeted therapy, and/or biological therapy including immunotherapy including, but not limited to acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; histone deacetylase inhibitors (HDACs) gemcitabine hydrochloride; hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; VITAXIN™

(see U.S. Patent Pub. No. US 2002/0168360 A1, dated Nov. 14, 2002, entitled "Methods of Preventing or Treating Inflammatory or Autoimmune Disorders by Administering Integrin αvα3 Antagonists in Combination With Other Prophylactic or Therapeutic Agents"); vorozole; zanoterone; zeniplatin; zilascorb; and zinostatin stimalamer.

5.7 Vaccine Formulations

In another embodiment, a therapeutic agent capable of ablating the B10 cell subset can be administered in conjunction with a vaccine or other antigen in order to increase the immune response directed against an infectious disease or cancer-associated target, e.g., a tumor or antigen. In the methods, the antigen is administered to the subject and an agent that kills or inhibits the function, localization or expansion of the IL-10 producing B10 cells or an agent that inhibits production of IL-10 by B10 cells in subject is also administered to the subject. The administration of the antigen and the agent increases or enhances the immune response directed to the antigen after administration as compared to the immune response directed to the antigen if administered in the absence of the agent. In particular, the method increases Ig class switching and in particular the levels of IgG are enhanced. According to this embodiment, ablation of the B10 cell subset serves to decrease endogenous levels of IL-10 in the subject being vaccinated or administered the antigen and thereby boosts the immune response, in particular the IgG response, directed to the infectious agent, infected cells, antigen or tumor antigen. Any antigen, including antigens associated with any infectious disease or malignant cell can be vaccinated against according to this method of the invention.

A non-limiting list of FDA licensed vaccines (and associated disease) that could be administered in accordance with the methods of the invention includes: Acel-Immune (Diphtheria, tetanus, pertussis), ActHIB (*Haemophilus influenzae* type b), Anthrax vaccine, Attenuvax (Measles), Biavax II (Rubella, Mumps), Botox (Botulism), Chickenpox vaccine, Cholera vaccine, Comvax (*Haemophilus influenzae* type b, Hepatitis B), DTP (Diphtheria, Tetanus, Pertussis), Diphtheria vaccine, Engerix-B (Hepatitis B), Influenza vaccine, Fluvirin (Influenza), German Measles vaccine, Havrix (Hepatitis A), HBIG (Hepatitis B), Hepatitis A vaccine, Hepatitis B vaccine, Heptavax (Hepatitis B), HibTITER (*Haemophilus influenzae* type b, Diphtheria), Imovax Rabies vaccine, Infanrix (Diphtheria, Tetanus, Pertussis), Ipol (Polio), JE-Vax (Japanese Encephalitis Virus), Pedvax-HIB (*Haemophilus influenzae* type b, Meningitis), Meningococcal polysaccharide vaccine (Meningitis), Menomune-A/C/Y/W-135 (Meningitis), Meruvax-II (Rubella), M-M-R II (Measles, Mumps, Rubella), M-R-VAX II (Measles, Mumps, Rubella), Mumpsvax (Mumps), OmniHIB (*Haemophilus influenzae* type b, Diphtheria), Orimune (Polio), Paratyphoid vaccine (Typhoid), Pertussis vaccine, Plague vaccine, Pneumococcal vaccine (Pneumonia), Pneumovax 23 (Pneumonia), Pne-Imune 23 (Pneumonia), Polio vaccine, Recombivax HB (Hepatitis B), RhoGAM (Rhesus), Rocky Mountain Spotted Fever vaccine, Rubella vaccine, Rubeola vaccine, Smallpox vaccine, Tetanus vaccine, Tetramune (Diphtheria, Tetanus, Pertussis, *Haemophilus influenzae* type b), Tice BCG USP (*Mycobacterium Bovis* Infection), Tri-Immunol (Diphtheria, Tetanus, Pertussis), Tripedia (Diphtheria, Tetanus, Pertussis), Typhim Vi (Typhoid), Typhoid vaccine, Typhus vaccine, Vaqta (Hepatitis A), Varicella vaccine, Varivax (Varicella), Vivotif Berna (Typhoid), and Yellow Fever vaccine. Some infectious diseases and tumors have been resistant to immunization protocols or have demonstrated limited immunity or required multiple boosts to elicit an effective immune response. The methods described herein may be combined with known vaccines or vaccines that failed during development stages to elicit a robust immune response to the antigen to reduce the number of boosters required or to increase the immune response directed to the antigen and increase the efficacy of the vaccine. As an example, the *Mycobacterium bovis* BCG vaccine is known to only provide partially protective immunity and thus is not used to vaccinate against tuberculosis in much of the world. The BCG vaccine could be administered with a an agent that inhibits the function, localization or expansion of B10 cells or an agent that inhibits IL-10 production to help elicit a more robust immune response to the vaccine.

In one aspect of this embodiment, the therapeutic agent capable of ablating the B10 cell subset and the vaccine or antigen are administered concurrently. In another aspect of this embodiment, the therapeutic agent capable of ablating the B10 cell subset is administered prior to administration of the vaccine or antigen. Alternatively, the therapeutic agent capable of ablating the B10 cell subset can be administered following the administration of the vaccine or antigen.

In another aspect of this embodiment, the therapeutic agent capable of ablating the B10 cell subset and the vaccine are administered in conjunction with an adjuvant. A non-limiting list of adjuvants administered in accordance with the methods of the invention includes: alum (e.g., aluminum hydroxide, aluminum phosphate); Montanide ISA 720; MF-59; PROVAX; immunostimulatory nucleic acids, such as CpG oligodeoxynucleotides; saponins purified from the bark of the *Q. saponaria* tree, such as QS21; poly[di(carboxylatophen-oxy)phosphazene, derivatives of lipopolysaccharides (LPS), such as monophosphoryl lipid A, muramyl dipeptide (MDP; Ribi) andthreonyl-muramyl dipeptide (t-MDP; Ribi); OM-174; *Leishmania* elongation factor; ISCOMs; SB-AS2; SB-AS4; non-ionic block copolymers that form micelles such as CRL 1005; Syntex Adjuvant Formulation CpG nucleic acids; Bacterial toxins, e.g., Cholera toxin (CT), CT derivatives including but not limited to CT B subunit (CTB); *Zonula occludens* toxin, zot; *Escherichia coli* heat-labile enterotoxin; Labile Toxin (LT), LT derivatives including but not limited to LT B subunit (LTB); Pertussis toxin, PT; toxin derivatives; Lipid A derivatives (e.g., monophosphoryl lipid A, MPL); bacterial outer membrane proteins (e.g., outer surface protein A (OspA) lipoprotein of *Borrelia burgdorferi*, outer membrane protein of *Neisseria meningitidis*).

In the methods described herein, the increase immune response in response to administration of the antigen and an agent that reduces B10 cell function, localization expansion or production of IL-10 can be measured by methods known to those of skill in the art including but not limited to ELISA, Western blot, ELISpot, dot blot. The enhanced immune response may include enhanced antigen specific antibody production and in particular enhanced class switching, e.g. enhanced IgG production. As described above the subjects include mammals, including domesticated animals such as livestock, pets, and primates including monkeys and humans.

5.8 Diagnostics

In another embodiment, methods are provided for diagnosing a subject suffering from a disease that is associated with elevated or diminished levels of IL-10 production. In another embodiment, a subject with a predisposition to a certain disease can be diagnosed. In an aspect of these embodiments, B10 cells are isolated from the subject and assayed for specificity to a certain disease-specific antigen.

The B10 cells to be analyzed may be collected from any location in which they reside in the subject including, but not limited to, blood, spleen, thymus, lymph nodes, and bone marrow. The isolated B10 cells may be analyzed intact, or lysates may be prepared for analysis.

Methods for the quantitation of cells and detection of antigenic specificity are known in the art, and may include pre-labeling the sample directly or indirectly; adding a second stage antibody that binds to the antibodies or to an indirect label, e.g., labeled goat anti-human serum, rat anti-mouse, and the like. For example, see U.S. Pat. No. 5,635,363. Generally, assays will include various negative and positive controls, as known in the art.

Various methods are used to determine the antigenic specificity profile from a patient sample. The comparison of a binding pattern obtained from a patient sample and a binding pattern obtained from a control, or reference, sample is accomplished by the use of suitable deduction protocols including, but not limited to, AI systems, statistical comparisons, and pattern recognition algorithms. Typically a data matrix is generated, where each point of the data matrix corresponds to a readout from a specific epitope. The information from reference patterns can be used in analytical methods to determine relative abundance, changes over time, and any other factors relevant to analysis.

Any disease can be diagnosed according to these embodiments. In particular, diseases associated with diminished levels of endogenous IL-10, e.g., immune and inflammatory diseases, and diseases associated with elevated levels of endogenous IL-10, e.g., cancer can be diagnosed based on isolation of B10 cells in a subject with disease-specific antigen specificity.

In another embodiment, a subject diagnosed with a given disease can be monitored for disease progression. Formats for patient sampling include time courses that follow the progression of disease, comparisons of different patients at similar disease stages, e.g., early onset, acute stages, recovery stages; and tracking a patient during the course of response to therapy. In an aspect of this embodiment, the numbers of B10 cells having specificity to a certain disease-specific antigen can be monitored over the course of a given therapy. As a non-limiting example, a therapy designed to expand the endogenous population of B10 cells that respond to a given disease should result in an increase in the numbers of B10 cells with specificity to a certain antigen associated with said disease relative to the general population of B10 cells.

Figures 1C, 1D:
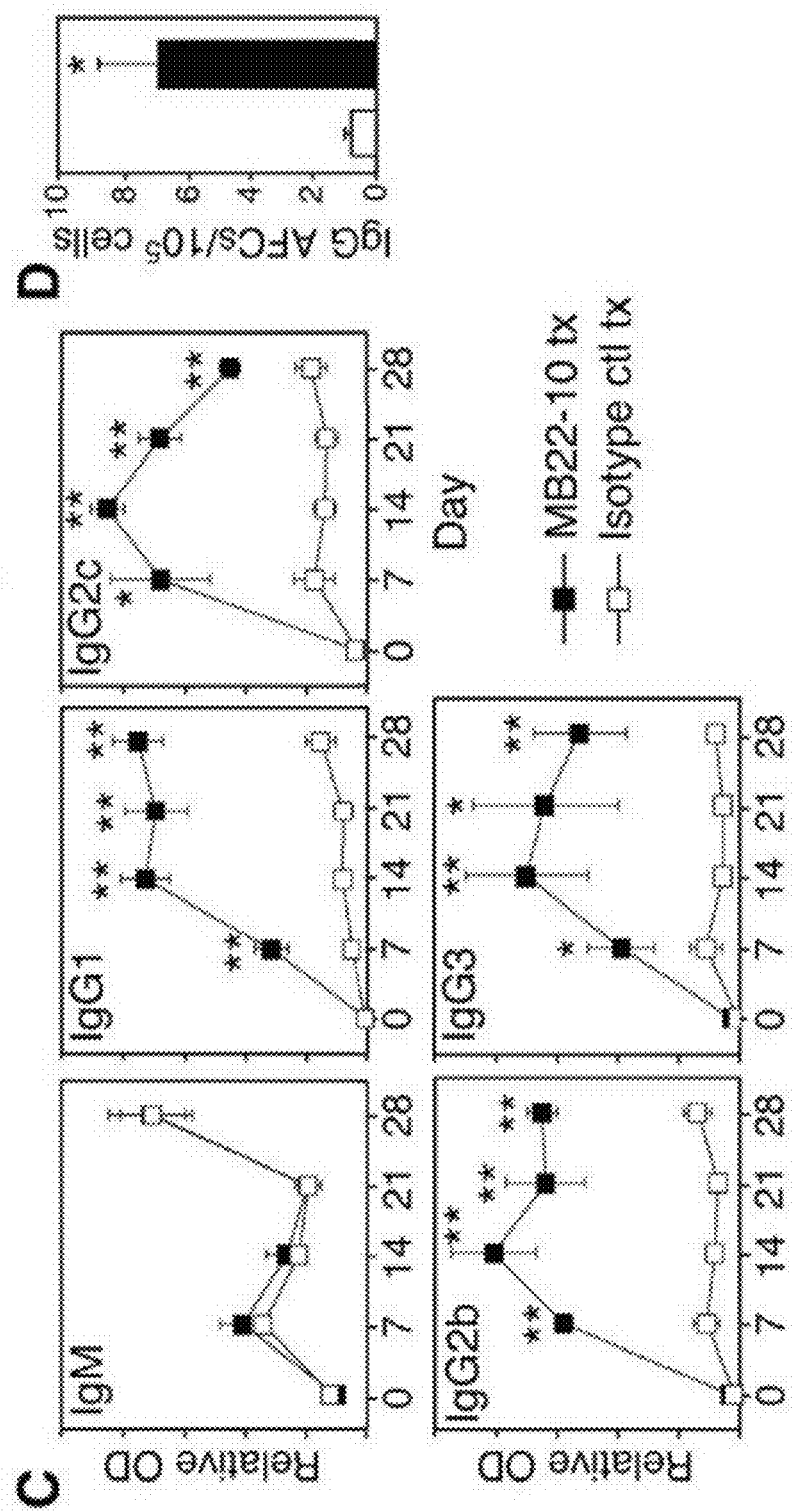

6. Example 1: CD22 Antibodies Deplete the Regulatory B Cell Population and Depletion Enhances IgG Production Administration of CD22 mAbs to mice results in depletion of the regulatory B cell population as evidenced by a decrease in $CD1d^{high}CD5^+$ B cells (FIG. 1A) and a decrease in B cell IL-10 production (FIG. 1B). Thus, CD22 mAb treatment efficiently depleted spleen B10 cells while leaving most other spleen B cells intact. Effective B10 cell depletion by MB22-10 mAb in wild-type mice provides a system to investigate whether B10 cell depletion by CD22 mAb would enhance the IgG responses in wild-type mice immunized with a T cell dependent antigen in the absence of adjuvant. DNP-KLH immunization induced significant primary and secondary (day 21 boost) DNP-specific IgM responses in control mAB-treated wild-type mice, while DNP-specific IgG responses rose only slightly above background levels (FIG. 1C). By contrast, CD22 mAb-treated mice generated normal Ag-specific IgM responses and robust DNP-specific IgG1, IgG2c, IgG2b, and IgG3 Ab responses that remained high. CD22 mAb treatment also significantly expanded the frequency of spleen IgG-secreting B cells in comparison with control mAb-treated mice (FIG. 1D). Thereby B10 cell depletion dramatically enhances IgG responses in wild-type mice.

7. Example 2: Characterization of the Human B10 Cell Population

The results shown below identify IL-10 competent B10 and B10pro cells in man that are comparable to those identified in mice, and show that both adaptive and innate signals can drive human B10 cell maturation and IL-10 production.

7.1 Materials and Methods

7.1.1 Cell Preparation

Heparinized blood samples were obtained from healthy 22 to 53 year-old adult donors or from patients with autoimmune disease, with B cells examined immediately thereafter. Tissue samples were obtained anonymously at surgery or postmortem from individuals without identifiable hematologic disorders, with the B cells purified and immediately cryopreserved and then kept frozen in liquid nitrogen until use. Tonsils were obtained from patients undergoing a routine tonsillectomy. Umbilical cord blood samples were obtained from frozen research units that were processed at the Duke University Stem Cell Laboratory and the Carolinas Cord Blood Bank.

7.1.2 Mice

C57BL16 mice were from the Jackson Laboratory (Bar Harbor, Me.). All mice were housed in a specific pathogen-free barrier facility and used at 8-12 wk of age.

7.1.3 Antibodies

Anti-human mAbs included: IgD (IA6-2) from BD PharMingen (San Diego, Calif.); CD21 (BU33), CD22 (RFB4), CD23 (D.6) from Ancell (Bayport, Minn.); IgM (MHM-88), CD1d (51.1), CD5 (UCHT2), CD19 (HIB19), CD24 (MLS), CD25 (BC96), CD27 (O323), CD38 (HIT2), CD40 (HB14), CD48 (BJ40), and CD148 (A3) mAbs from BioLegend (San Diego, Calif.). Anti-human IgM Ab was from Jackson ImmunoResearch Laboratories, Inc. (West Grove, Pa.). Phycoerythrin-conjugated anti-human IL-10 mAb (JES3-19F1) was from BioLegend (San Diego, Calif.).

Anti-mouse mAbs included: CD20 mAb (MB20-11; Uchida et al., 2004. Int. Immunol. 16:119-129); B220 mAb RA3-6B2 (obtained from Dr. Robert Coffman, DNAX Corp., Palo, Alto, Calif.); and CD19 (1D3), CD5 (53-7.3), CD1d (1B1), CD21/35 (7G6), CD23 (B3B4), CD24 (M1/69), CD25 (PC61), and CD40 (3/23) mAbs from BD PharMingen (San Diego, Calif.); CD27 (LG.3A10), CD38 (90) from BioLegend (San Diego, Calif.); IgM (11/41) from eBioscience (San Diego, Calif.); and IgD (11-26) from Southern Biotechnology Associates (Birmingham, Ala.); FITC-conjugated anti-mouse CD22 N-terminus (Cy34, TIB163, American Type Culture Collection). Phycoerythrin-conjugated anti-mouse IL-10 mAb (JES5-16E3) was from eBioscience (San Diego, Calif.).

7.1.4. B Cell Isolation, Immunofluorescence Analysis and Cell Sorting

Blood mononuclear cells were isolated from heparinized blood after centrifugation over a discontinuous Lymphoprep (Axis-Shield PoC As, Oslo, Norway) gradient. Single cell splenocyte, lymph node, and tonsil suspensions were generated by gentle dissection with >90% cell viability as determined by trypan blue exclusion. Cell numbers were quantified using a hemocytometer, with relative lymphocyte percentages among viable cells (based on scatter properties) determined by flow cytometry analysis. In some experiments, B cells were enriched using RosetteSep (STEMCELL Technologies, Vancouver, BC, Canada) following the manufacturer's protocols. CD19-mAb coated microbeads (Miltenyi Biotech) were used to purify blood B cells by positive selection following the manufacturer's instructions. When necessary, the cells were enriched a second time using a fresh MACS column to obtain >99% purities.

Single cell leukocyte suspensions were stained on ice using predetermined optimal concentrations of each Ab for 20-60 min, and fixed as described (Sato et al., 1996, *J. Immunol.* 157:4371-4378). Cells with the light scatter properties of lymphocytes were analyzed by 2-6 color immunofluorescence staining and FACScan or FACSCalibur flow cytometers (Becton Dickinson, San Jose, Calif.). Dead cells were excluded from the analysis based on their forward- and side-light scatter properties and the use of LIVE/DEAD Fixable Dead Cell Stain Kits (Invitrogen-Molecular Probes, Carlsbad, Calif.). All histograms are shown on a 4-decade logarithmic scale, with gates shown to indicate background isotype-matched control mAb staining set with <2% of the cells being positive. Blood $CD24^{hi}CD27^+$ and $CD24^{low}/CD27^-$ B cells were isolated using a FACSVantage SE flow cytometer (Becton Dickinson, San Jose, Calif.) with 90-95% purities.

7.1.5. Analysis of IL-10 Production

Intracellular IL-10 analysis by flow cytometry was as described (Yanaba et al., 2008, *Immunity* 28:639-650). Briefly, isolated mononuclear cells or purified B cells were resuspended ($2 \times 10^6$ cells/ml) in complete medium [RPMI 1640 media containing 10% FCS, 200 µg/ml penicillin, 200 U/ml streptomycin, and 4 mM L-Glutamine, with $5 \times 10^{-5}$ M 2-mercaptoethanol in mice, without 2-mercaptoethanol in human (all from Gibco, Carlsbad, Calif.)]. The cells were stimulated with LPS (10 µg/ml, *Escherichia coli* serotype 0111: B4; Sigma), CpG (human ODN 2006, mouse ODN 1826, 10 µg/ml; Invivogen), or other TLR agonists (TLR1, Pam3CSK4, 1 µg/ml; TLR2, heat-killed *Listeria monocytogenes*, $10^8$ cells/ml; TLR3, Poly(I:C), 10 µg/ml; TLR5, *S. typhimurium* flagellin, 1 µg/ml; TLR6, Pam2CGDPKHPKSF, 1 µg/ml; TLR7, Imiquimod, 1 µg/ml; TLR8, ssRNA40, 1 µg/ml; all from Invivogen), CD40L (1 µg/ml; R&D Systems, Minneapolis, Minn.), anti-human CD40 mAb (1 µg/ml; BioLegend), anti-mouse CD40 mAb (1 µg/ml; BD Pharmingen), PMA (50 ng/ml; Sigma), ionomycin (human 1 µg/ml, mouse 500 ng/ml; Sigma), BFA (1× solution/ml; BioLegend), monensin (2 mM; eBioscience), and anti-human IgM Ab (10 µg/ml; Jackson ImmunoResearch Laboratories) as indicated for 5 or 48 h, in 48-well flat-bottom plates before staining and flow cytometry analysis. For analysis of cell proliferation, lymphocytes were stained with CFSE Vybrant™ CFDA SE fluorescent dye (5 µM; Invitrogen-Molecular Probes) according to the manufacturer's instructions. For IL-10 detection, Fc receptors were blocked with mouse Fc receptor mAb (2.4G2; BD PharMingen) or human FcγR-Binding inhibitor (eBioscience) with dead cells detected by using a LIVE/DEAD® Fixable Violet Dead Cell Stain Kit (Invitrogen-Molecular Probes) before cell surface staining. Stained cells were fixed and permeabilized using a Cytofix/Cytoperm kit (BD PharMingen) according to the manufacturer's instructions and stained with phycoerythrin-conjugated anti-human or anti-mouse IL-10 mAb.

Secreted IL-10 was quantified by ELISA. Purified B cells ($4 \times 10^5$) were cultured in 0.2 ml of complete medium in a 96-well flat-bottom tissue culture plates. Culture supernatant fluid IL-10 concentrations for triplicate samples were quantified using IL-10 OptEIA ELISA kits (BD PharMingen) following the manufacturer's protocols.

7.1.6. B Cell IL10 Transcript Expression

In some experiments, IL-10-secreting blood B cells were identified after 4 h of in vitro stimulation using an IL-10 secretion detection kit (Miltenyi Biotech, Auburn, Calif.) with subsequent staining for CD19 expression before cell sorting into $IL-10^+CD19^+$ and $IL-10^-CD19^+$ populations. Total RNA was extracted from the purified B cells using Qiagen RNeasy spin columns (Qiagen Ltd., Crawley, UK). Random hexamer primers (Promega, Madison, Wis.) and Superscript II RNase H Reverse Transcriptase (Invitrogen, Carlsbad, Calif.) were used to generate cDNA. IL-10 transcripts were quantified by real-time PCR analysis using SYBR Green as the detection agent as described. The PCR was performed with the iCycler iQ system (Bio-Rad, Hercules, Calif.). All components of the PCR mix were purchased from Bio-Rad and used according to the manufacturer instructions. The reaction conditions were as follows: 2 min at 50° C. (1 cycle), 10 min at 95° C. (1 cycle), 15 s at 95° C., and 1 min at 60° C. (50 cycles). Specificity of the RT-PCR was controlled by the generation of melting curves. Relative expression of PCR products was determined using the $\Delta\Delta CT$ method. Briefly, each set of samples was normalized using the difference in threshold cycle (CT) between the target gene and housekeeping gene (GAPDH): $\Delta CT=(CT$ target gene$-CT$ GAPDH). Relative mRNA levels were calculated by the expression $2^{-\Delta\Delta CT}$, where $\Delta\Delta CT=\Delta CT$ sample$-\Delta CT$ calibrator. For all reactions, each condition was performed in triplicate. Data analysis was performed using iQ Cycler analysis software. The sense IL-10 primer was 5'-CTTCGAGATCTCCGAGATGCCTTC-3' (SEQ ID NO: 6) and the antisense primer was 5'-ATTCTTCACCTGCTCCACGGCCTT-3' (SEQ ID NO: 7). The sense GAPDH primer was 5'-GCCACCCAGAAGACTGTGGATGGC-3' (SEQ ID NO: 8) and the antisense primer was 5'-CATGTAGGCCATGAGGTCCACCAC-3' (SEQ ID NO: 9).

7.1.7. Patients

All subjects with rheumatoid arthritis (RA) met the American College of Rheumatology 1987 revised criteria for classification (Arnett et al., 1988, Arthritis Rheum. 31:315-324); subjects with systemic lupus erythematosus (SLE) satisfied the 1982 revised criteria for the classification (Tan et al., 1982, *Arthritis Rheum.* 25:1271-1277); and subjects with primary Sjögren's syndrome (SjS) fulfilled the American-European consensus group revised criteria for the classification (Vitali et al., 2002, *Ann. Rheum. Dis.* 61:554-558). Patients with autoimmune vesiculobullous skin disease (BD) included bullous pemphigoid (BP), pemphigus foliaceus (PF), and pemphigus vulgaris (PV). All patients had typical clinical and histologic findings with diagnostic findings on direct immunofluoroesence of perilesional skin or oral mucosa (Yancey and Egan, 2000, *J. Amer. Med. Assoc.* 284:350-356; Udey and Stanley, 1999, *JAMA* 282: 572-576). Informed consent for multiple sclerosis (MS) patient's blood samples was obtained in each instance according to protocols approved by the Institutional Review Board of St. Luke's—Roosevelt Hospital Center Institute for Health Sciences. All patients with MS fulfilled 2005 revised McDonald criteria for relapsing remitting or primary progressive MS (Polman et al., 2005, *Ann. Neurol.* 58:840-846). Secondary progressive MS was defined using the Lublin and Reingold criteria (Lublin and Reingold, 1996, *Neurology* 46:907-911). Most patients were receiving treatment with immunomodulatory drugs and/or low doses of prednisone (see Table 1, below).

7.1.8. Statistical Analysis

All data are shown as means (±SEM). Significant differences between sample means were determined using the Student's t test.

7.2 Results 7.2.1. Identification of Human IL-10-Producing B Cells

Figures 2A, 2B, 2C, 2D:
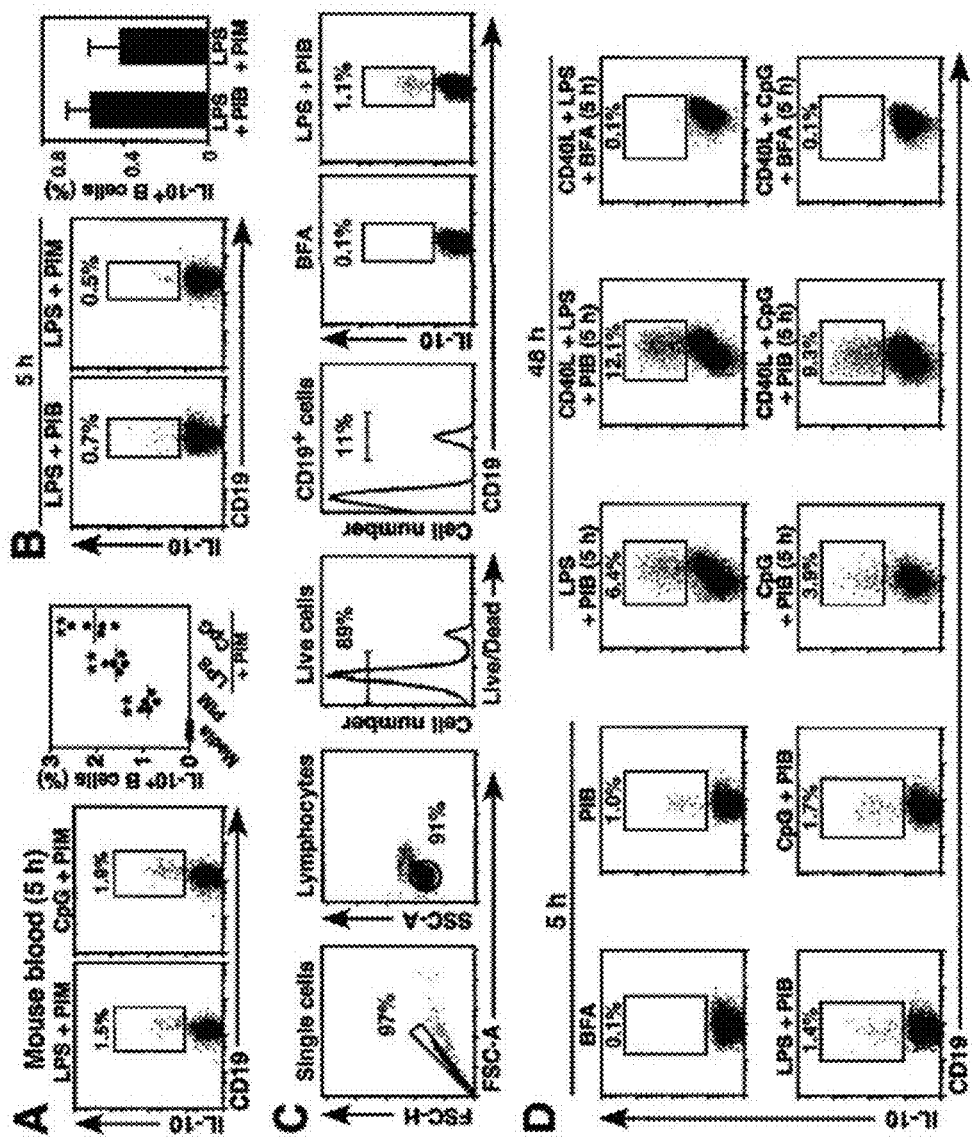

Mouse blood B10 cell frequencies were determined after culturing the cells with media, PIM, L+PIM, or CpG oligonucleotides plus PIM (CpG+PIM) for 5 h in vitro. Blood B cells did not express detectable IL-10 without in vitro stimulation. However, IL-10 competent B10 cells represented <3% of mouse blood B cells, with the combination of CpG+PIM inducing higher frequencies of B10 cells than L+PIM or PIM alone (FIG. 2A). A similar strategy to that used in mice was optimized to maximize human IL-10 competent B10 cell enumeration. Brefeldin A (BFA) was used to block IL-10 golgi transport rather than monensin since it optimized human B cell cytoplasmic IL-10 expression (FIG. 2B). Optimal human B10 cell numbers were observed after 5 h of PIB stimulation in vitro, with overall B cell viability decreasing after this time point. Background IL-10 mAb staining was reduced by the exclusion of all cell doublets and dead cells from the flow cytometry analysis with BFA cultures used as negative controls (FIG. 2C). These assay conditions were then used to identify human IL-10-competent blood B cells.

Human blood was found to contain a rare, but distinct subset of IL-10-competent B10 cells that was detectable at low 0.25-2% frequencies after in vitro stimulation. B cell activation with PMA, ionomycin, and BFA (PIB) for 5 h induced 0.8±0.1% of B cells on average to express IL-10 (n=14, 1.9±0.3×10$^{-3}$ B10 cells/ml, FIG. 2D-E). Some blood B cells may spontaneously express IL-10, but their frequencies and levels of IL-10 expression were below the 0.2% threshold of quantification by immunofluorescence staining; which is similar to background cytoplasmic IL-10 staining when using B cells from IL-10$^{-/-}$ mice (see Yanaba et al., 2008, *Immunity* 28:639-650; Matsushita et al., 2008, *J. Clin. Invest.* 118:3420-3430; and Yanaba et al., 2009, *J. Immunol.* 182:7459-7472). B cell stimulation using TLR agonists did not substantially alter mean B10 cell numbers, although IL-10$^+$ B cell frequencies were enhanced in some individuals by adding either CpG (TLR9 agonist) or LPS to the PIB cultures. Thus, blood B10 cells were rare, a trait shared by both healthy humans and mice.

7.2.2. Human B10pro Cell Identification

Figures 2E, 2F, 2G:
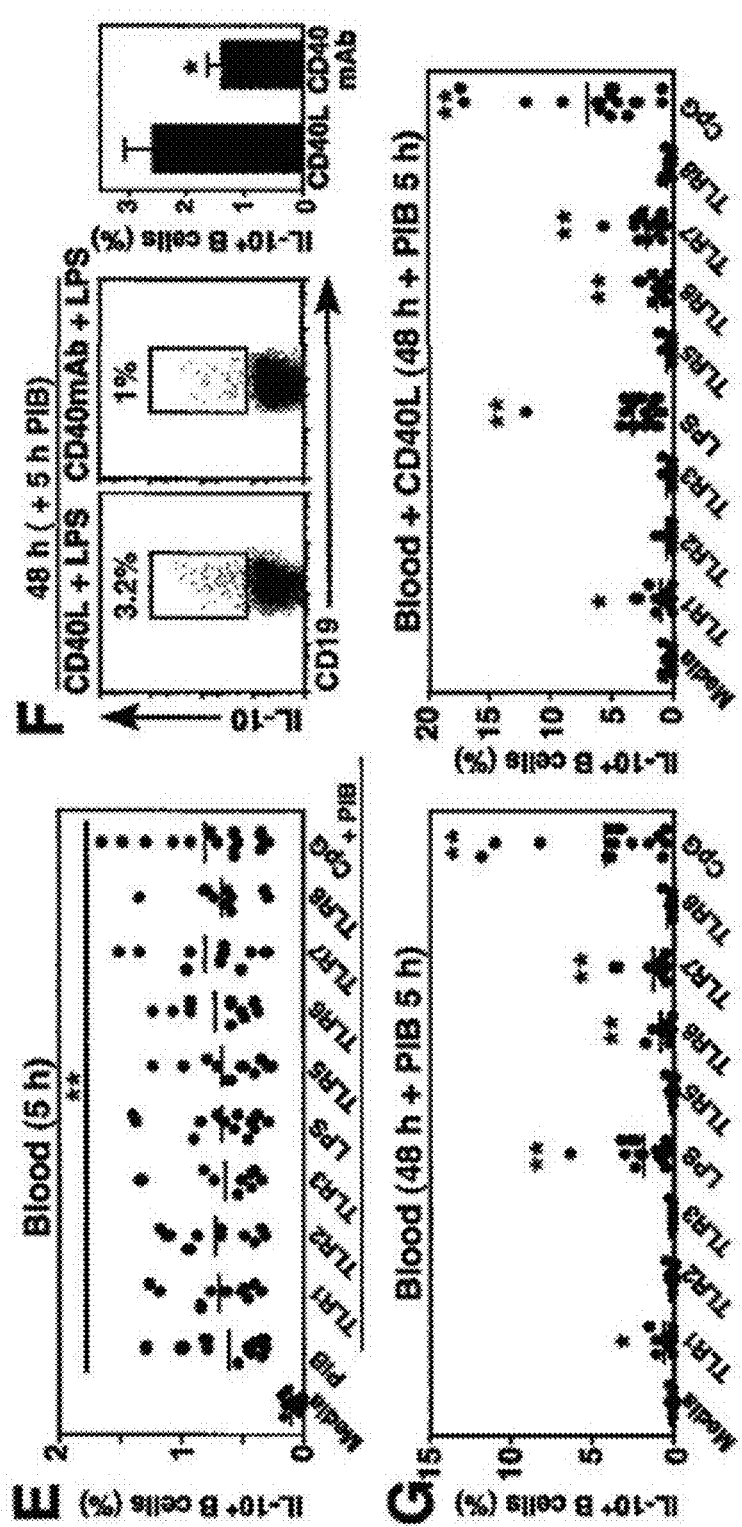

In mice, B10pro cell maturation into IL-10-competent B10 cells can be induced by 48 h stimulation with either LPS or agonistic CD40 mAb (Yanaba et al., 2009, *J. Immunol.* 182:7459-7472). B10pro cells capable of maturing into IL-10 competent B10 cells after in vitro culture for 48 h were identified in human blood by their ability to express cytoplasmic IL-10 after 5 h PIB stimulation (FIG. 2D). The total frequency of B10 and B10pro cells (B10+B10 pro) is quantified in this assay, as the B cells that acquire IL-10 competence in vitro (e.g. matured B10pro cells) cannot be differentiated from preexisting blood B10 cells. Culturing human B cells with LPS, CpG, or recombinant CD40 ligand (CD40L, CD154) alone, together, or in combination with BFA did not induce detectable cytoplasmic IL-10 expression, while ~0.2% of B cells cultured in media alone with 5 h PIB stimulation during the last 5 h of culture expressed cytoplasmic IL-10 (FIG. 2F-G). However, 1-4% of human blood B cells expressed IL-10 following TLR agonist (48 h)+PIB (5 h) stimulation. B10+B10pro cell frequencies increased to 0.6±0.1, 1.9±0.4, 0.8±0.1, 1.2±0.2, and 4.1±1.0% following TLR1 agonist, LPS, TLR6 agonist, TLR7 agonist, and CpG stimulation, respectively.

The addition of recombinant CD40L alone to B cell cultures did not induce B10pro cell maturation, while the addition of CD40L to B cells stimulated with LPS induced higher frequencies of B10+B10pro cells. CD40L induced 47% higher frequencies of IL-10$^+$ B10 cells than agonistic CD40 mAb (FIG. 2F). CD40L stimulation also significantly enhanced mean B10+B10pro cell frequencies when combined with TLR1 agonist (1.1±0.2%), LPS (3.4±0.7%), TLR6 agonist (1.4±0.2%), TLR7 agonist (2.2±0.4%), or CpG (7.0±1.4%) stimulation (FIG. 2G right panel). Thus, dual CD40 and TLR stimulation induced the highest frequencies of human B10pro cells to become IL-10 competent B10 cells, with the highest numbers of B10+B10pro cells (1.6±0.3×10$^4$ cells/ml, n=14) induced after 48 h of CD40L plus CpG stimulation. Thereby, human blood B10 and B10pro cells can be readily and reproducibly quantified after stimulation or in vitro maturation with CD40 ligation in combination with select TLR signals.

7.2.3. B10 Cell Numbers in Newborn Blood and Adult Lymphoid Tissues

Figures 3A, 3B:
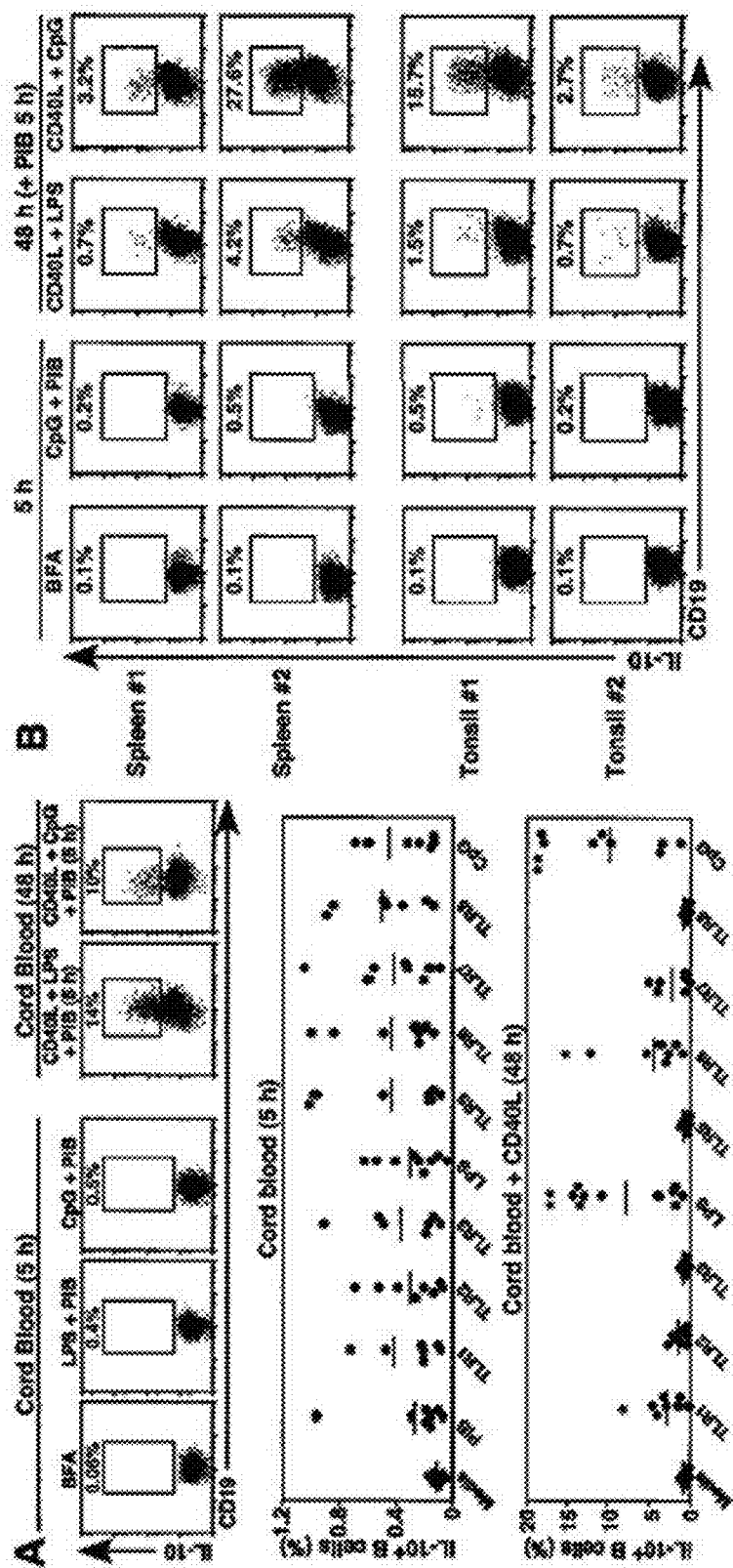

Newborn mice have higher spleen B10 and B10pro cell frequencies than adult mice (Yanaba et al., 2009, *J. Immunol.* 182:7459-7472). Mean B10 cell frequencies in human newborn blood after 5 h of CpG+PIB stimulation (0.45±0.14%, n=8; FIG. 3A) were 42% lower than those observed for adult human blood (FIG. 2E), although this may reflect donor pool diversity rather than represent differences between newborns and adults. Nonetheless, B10+B10pro cell frequencies were similar or higher in newborn blood relative to adult human blood after culture with CD40L and TLR agonists; TLR1 (2.6±0.6%), LPS (7.6±1.8%), TLR6 (4.2±1.4%), or TLR9 (CpG, 9.6±2.3%) agonists with PIB added during the final 5 h of culture. Thus, newborn and adult blood contained both B10 and B10pro cells.

Figure 3C:
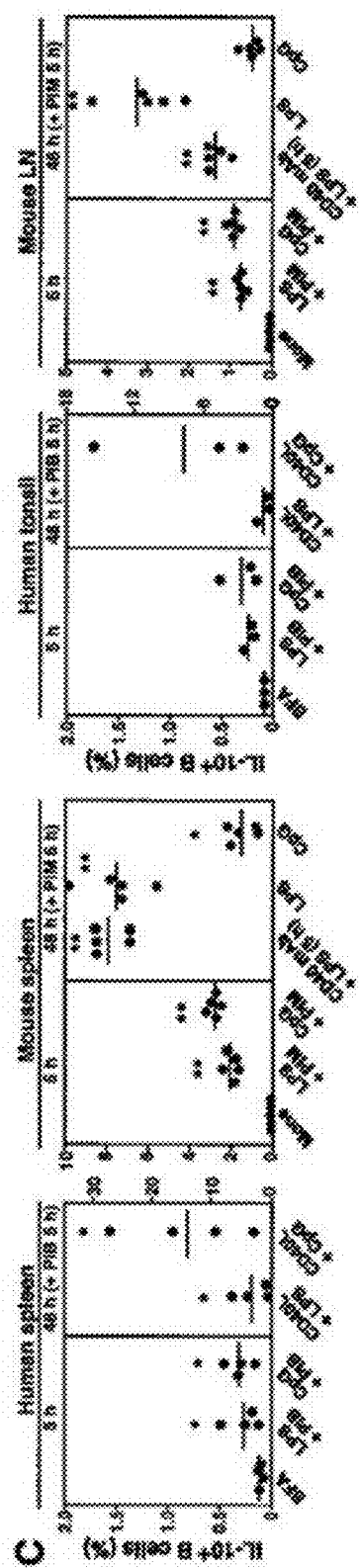

B10 cells were also found within spleens (0.31±0.06, n=4, CpG+PIB) and tonsils (0.31±0.11, n=3, CpG+PIB) of individuals without known disease (FIG. 3B-C). Stimulating spleen and tonsil B cells with LPS or CpG in combination with CD40L also induced B10pro cells to mature into IL-10 competent B10 cells, with B10+B10pro cell frequencies ranging from <0.5% to almost 30% (FIG. 3B). Human tonsil and spleen B10 cell frequencies were numerically similar to those observed in blood, but spleen B10+B10pro cell frequencies were 2.2-fold higher. In these samples, human spleen and tonsil B10 cell frequencies were 62-85% lower than those observed for mouse spleen (0.3% vs. 2.1%) and lymph node (0.3% vs. 0.8%), respectively, but B10+B10pro cell frequencies were higher within human tissues. It was observed that CpG stimulation induced human B10pro cell maturation, while CpG failed to induce mouse B10pro cell maturation (FIG. 3C). Regardless, B10 cells represented a small subset of human spleen and lymph node B cells.

7.2.4. Regulation of B10 Cell IL-10-Production and Secretion In Vitro

Figures 4A, 4B, 4C, 4D, 4E:
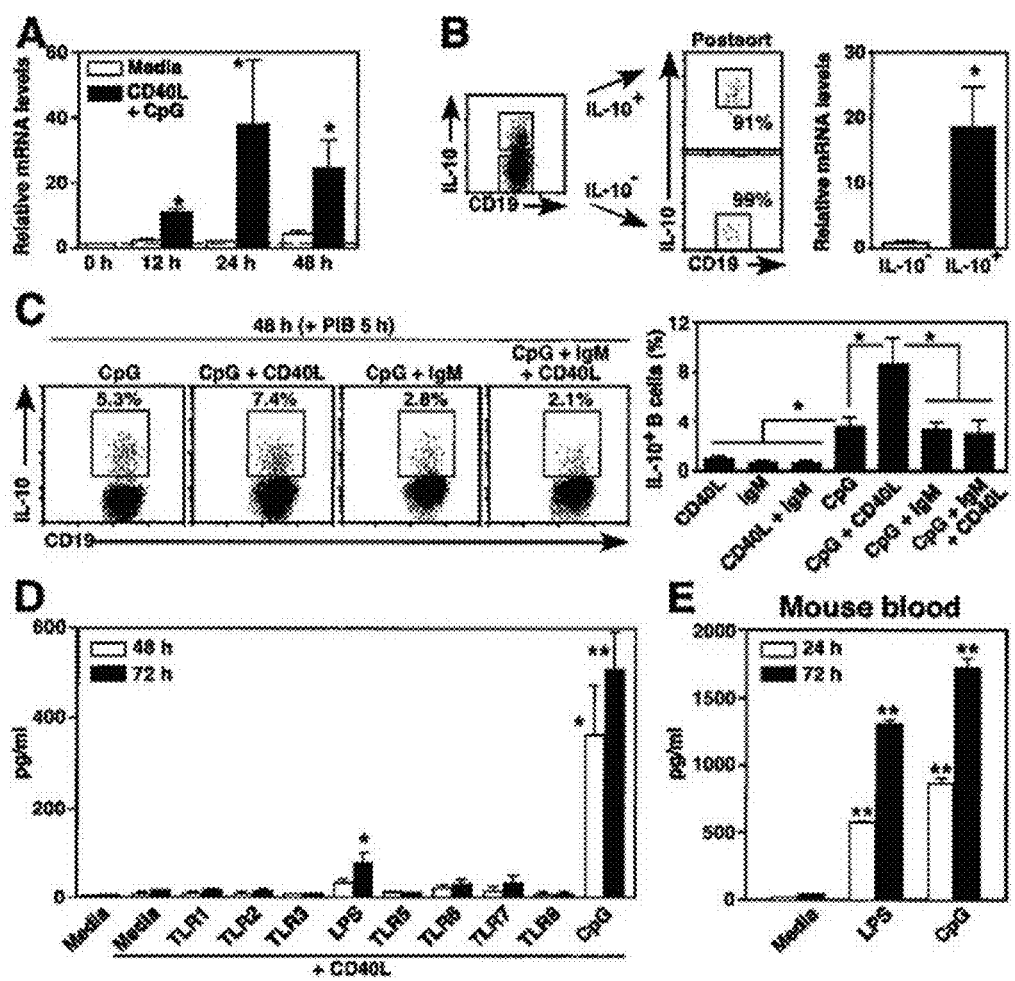

The time course of B10 cell IL-10 induction was assessed in vitro by quantifying IL-10 transcripts in cultured human blood B cells stimulated with CD40L+CpG. By 12, 24, and 48 h, B cell stimulation induced 6.8-, 24-, and 5.9-fold higher 1110 transcript levels, respectively, than was observed for unstimulated B cells (p<0.05; FIG. 4A). Human blood B10 cells that were actively secreting IL-10 expressed 1110 transcripts at 19-fold higher levels than IL-10⁻ B cells after in vitro stimulation (FIG. 4B). Thus, B10 cell IL-10 expression paralleled 1110 gene transcription.

The response of human B10+B10pro cells to CD40L, CpG, and antigen receptor generated signals was examined. In comparison with CD40L alone, CpG alone induced the highest levels of B10pro cell maturation into IL-10-competent B10 cells, which was further increased when both CD40L and CpG were added to the cultures (FIG. 4C). By contrast, BCR ligation using mitogenic anti-IgM Ab did not induce cytoplasmic IL-10 expression, but actually inhibited the B10 cell inducing effects of CpG+CD40L stimulation. In vitro BCR signals also inhibit mouse B10pro cell maturation and cytoplasmic IL-10 induction (Yanaba et al., 2009, *J. Immunol.* 182:7459-7472). Among TLR agonists, LPS and CpG were also the most potent stimuli for inducing IL-10 secretion by human blood B cells (FIG. 4D) and mouse blood B cells (FIG. 4E). Thus, similar signals regulate human and mouse B10 and B10pro cells to mature and express cytoplasmic IL-10 in vitro.

7.2.5. Phenotypic Characterization of Blood and Spleen IL-10-Competent B Cells

Figures 5A, 5B, 5C, 5D:
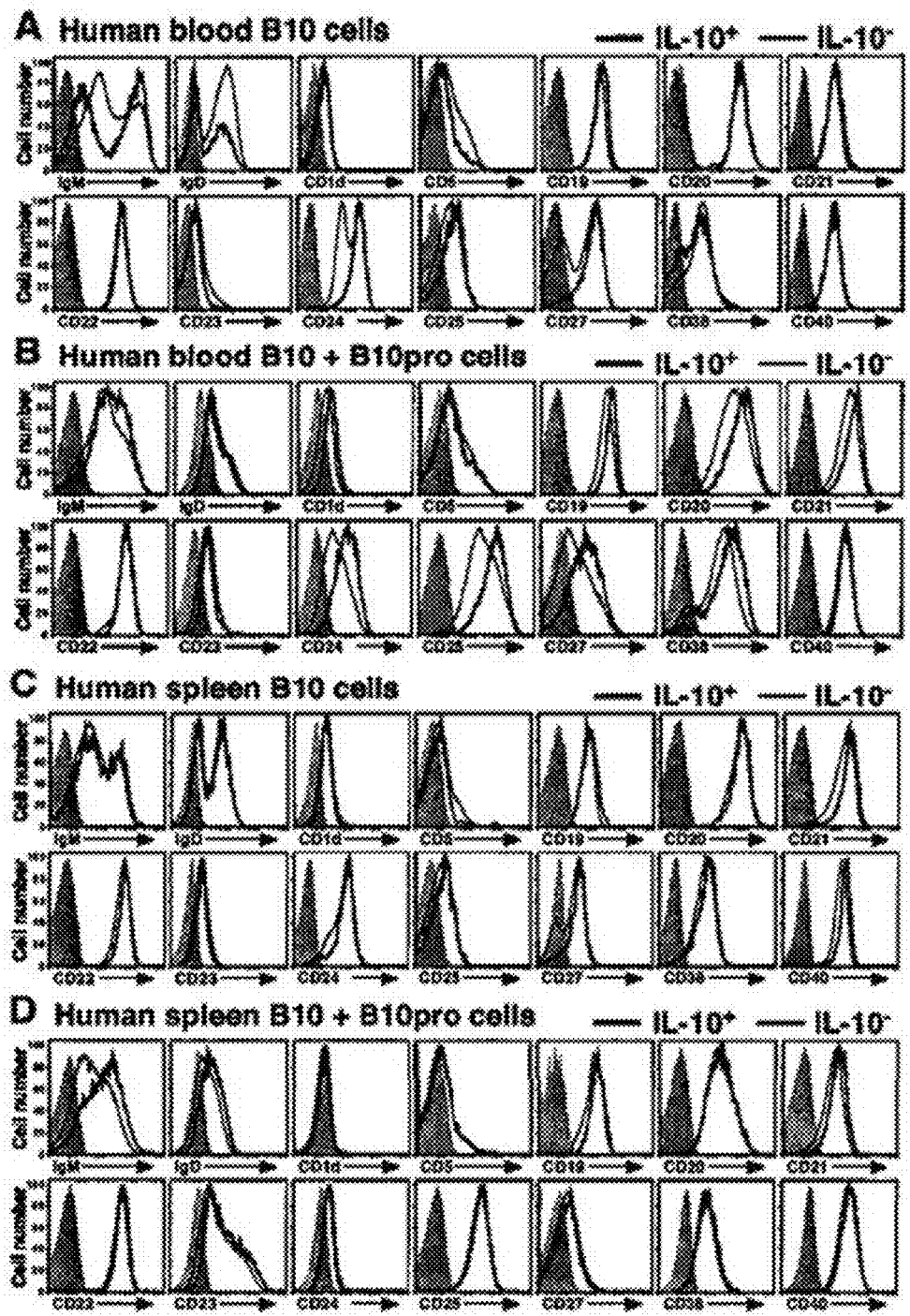

Whether human B10 cells represent a phenotypically defined B cell subset was determined by immunofluorescence staining. B cells that were either untreated, stimulated with PIB, L+PIB, or CpG+PIB for 5 h, and/or permeabilized, were found to express identical cell surface IgM, IgD, CD1d, CD5, CD10, CD19, CD21, CD22, CD23, CD24, CD25, CD27, CD38, and CD40 densities. The transport of newly synthesized proteins to the cell surface is also inhibited by BFA. The use of ten-fold higher PMA concentrations did not alter B cell surface phenotypes or survival during these 5 h assays, while the use of ionomycin at ten-fold higher concentrations significantly altered B cell surface phenotypes even in the presence of BFA due to extensive cell death. Since these cell surface molecules were not affected by the stimulation and/or cell permeabilization protocols used to visualize cytoplasmic IL-10 expression, they were used to categorize the phenotype of freshly isolated blood B10 cells. Half of blood B10 cells expressed high IgM levels and low IgD levels (FIG. 5A). Both CD24 and CD27 expression were high on the majority of B10 cells, while IL-10⁻ B cells expressed either high or low density CD24 and CD27. CD19 and CD25 expression were also higher on B10 cells than IL-10⁻ B cells. Otherwise, the remaining cell surface markers were absent or expressed similarly by both B10 cells and IL-10⁻ B cells. The same results were obtained following PIB, L+PIB, or CpG+PIB stimulation. Thereby, freshly isolated human blood IL-10-competent B10 cells were predominantly CD24$^{hi}$CD27⁺ B cells.

The phenotype of blood B10+B10pro cells induced during 48 h in vitro cultures was also assessed. In comparison with freshly isolated B cells after 5 h of L+PIB stimulation (FIG. 5A), prolonged cell culture and these stimulation conditions induced significant changes in the cell surface phenotype of B10 and non-B10 cells (FIG. 5B). For example, most B cells were induced to express CD25 and CD38 at high densities. Nonetheless, B10+B10pro cells on average expressed higher densities of CD1d, CD19, CD20, CD21, CD23, CD24, CD25, CD27, and CD38 when compared with IL-10⁻ B cells, consistent with an activated phenotype. Spleen B10 cells were also predominantly CD27⁺, although the expression of most cell surface molecules was similar if not identical for B10 cells and IL-10⁻ B cells (FIG. 5C). Spleen B10+B10pro cells and IL-10⁻ B cells also had similar phenotypes after 48 h of stimulation in vitro, with the exception that IL-10⁺ B10 cells were predominantly IgM$^{hi}$ while IL-10⁻ B cells were predominantly IgM$^{low}$ (FIG. 5D). Thereby, spleen B10 cells were also predominantly CD24$^{hi}$CD27⁺.

Figures 5E, 5F, 5G, 5H:
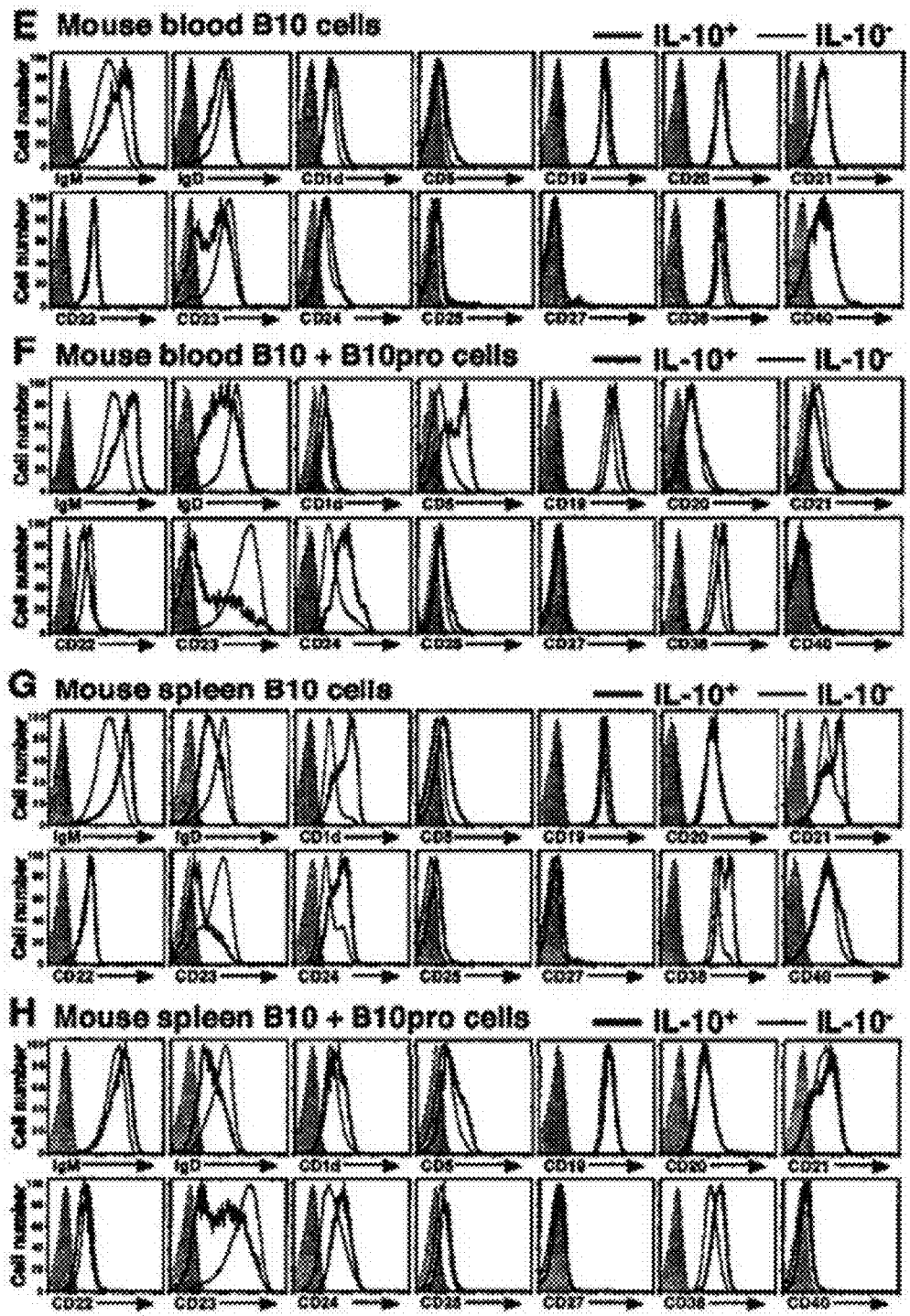

The phenotype of mouse blood B10 cells was also assessed for comparison. Mouse blood B10 cells expressed higher levels of IgM than IL-10⁻ B cells, but most other cell surface molecules were expressed at similar densities (FIG. 5E). CD1d, CD5, CD19, CD24, and CD38 expression were slightly higher on IL-10⁺ than IL-10⁻ B cells, while CD23 expression was heterogeneous in comparison to IL-10⁻ B cells. Mouse blood B10+B10pro cells were predominantly IgM$^{hi}$ CD5⁺CD19$^{hi}$ CD23$^{low}$ CD24$^{hi}$ CD38$^{hi}$ after in vitro activation (FIG. 5F). Spleen B10 cells were predominantly IgM$^{hi}$ IgD$^{low}$ CD1d$^{hi}$ CD5⁺CD19$^{hi}$ CD21$^{hi/int}$ CD23$^{low}$ CD24$^{hi}$ CD38$^{hi}$ (FIG. 5G). Mouse spleen B10+B10pro cells were more similar to IL-10⁻ B cells after 48 h of culture (FIG. 5H). Thereby, human blood B10 cells were predominantly CD24$^{hi}$CD27⁺, while mouse spleen B10+B10pro cells were predominantly CD1d$^{hi}$CD5⁺.

Figures 6A, 6B, 6C:
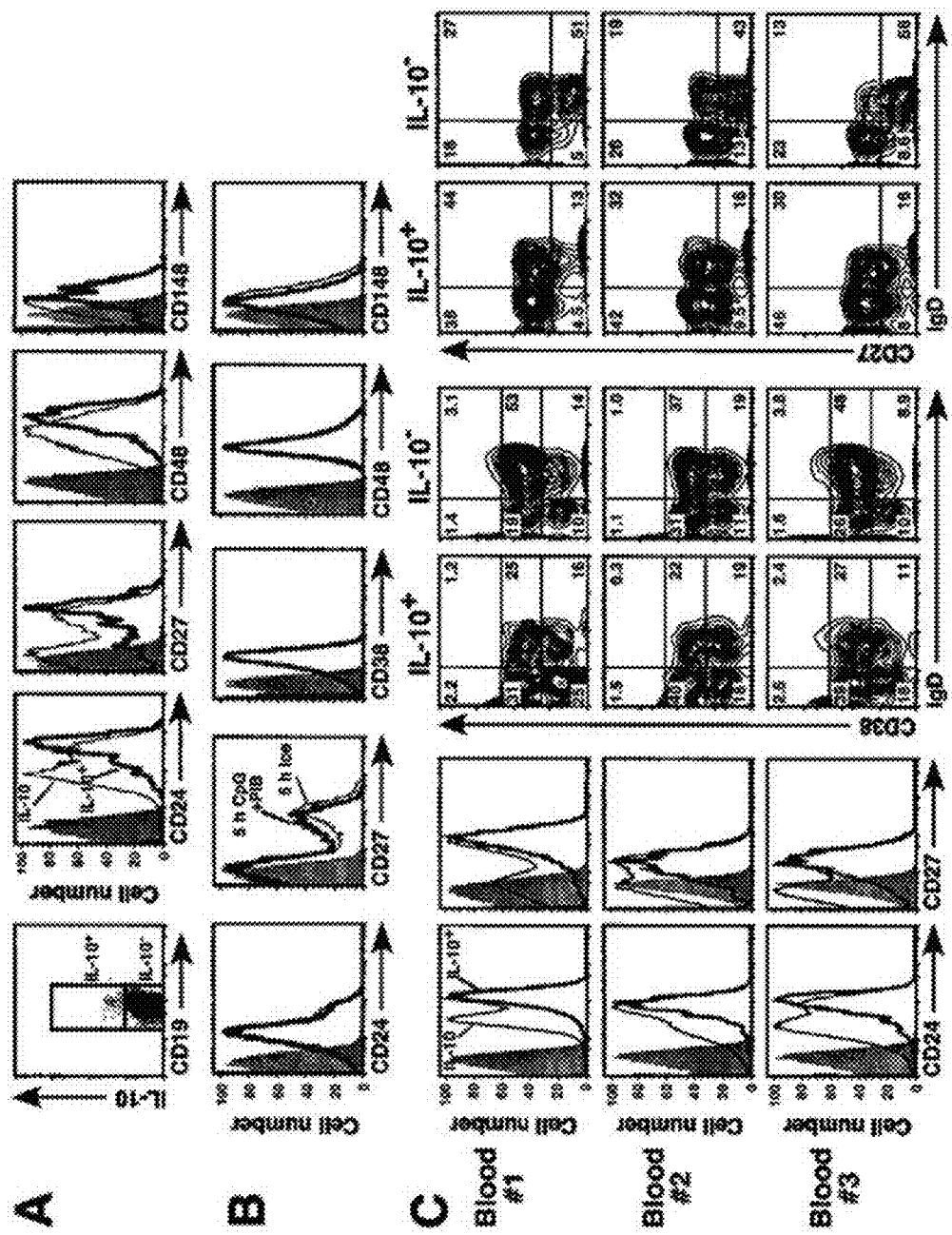

7.2.6. Blood B10 Cells are Enriched within the CD24$^{hi}$CD27⁺ B Cell Subpopulation When the spectrum of normal control blood donors was compared, blood B10 cells were predominantly CD24$^{hi}$ and CD27⁺ (FIG. 5A). Most B10 cells also expressed additional cell surface markers of activation (CD48$^{hi}$) and memory (CD148$^{hi}$) (FIG. 6A). Since cell surface CD24, CD27, CD38, and CD48, and CD148 expression were not affected by the 5 h culture conditions used to induce B cell cytoplasmic IL-10 expression (FIG. 6B), circulating B10 cells were predominantly CD24$^{hi}$, CD27⁺, CD48$^{hi}$, and CD148$^{hi}$. Cell surface CD27 and CD38 expression profiles have been used frequently to define human blood B cell subsets (see, e.g., Levesque and St. Clair, 2008, *J. Allergy Clin. Immunol.* 121:13-21; and Sanz et al., 2008, *Sem. Immunol.* 20:67-82). However, when blood B10 cells were analyzed based on their CD38 versus IgD expression profiles, IL-10⁺ B10 cells from representative blood donors fell into both the CD38$^{hi}$ and CD38$^{lo}$ populations (FIG. 6C). Similarly, when blood B10 cells were analyzed based on CD27 versus IgD expression, IL-10⁺ B cells from representative blood donors did not fall into pre-defined subsets, but were predominantly CD27$^{hi}$.

Figures 6D, 6E, 6F, 6G:
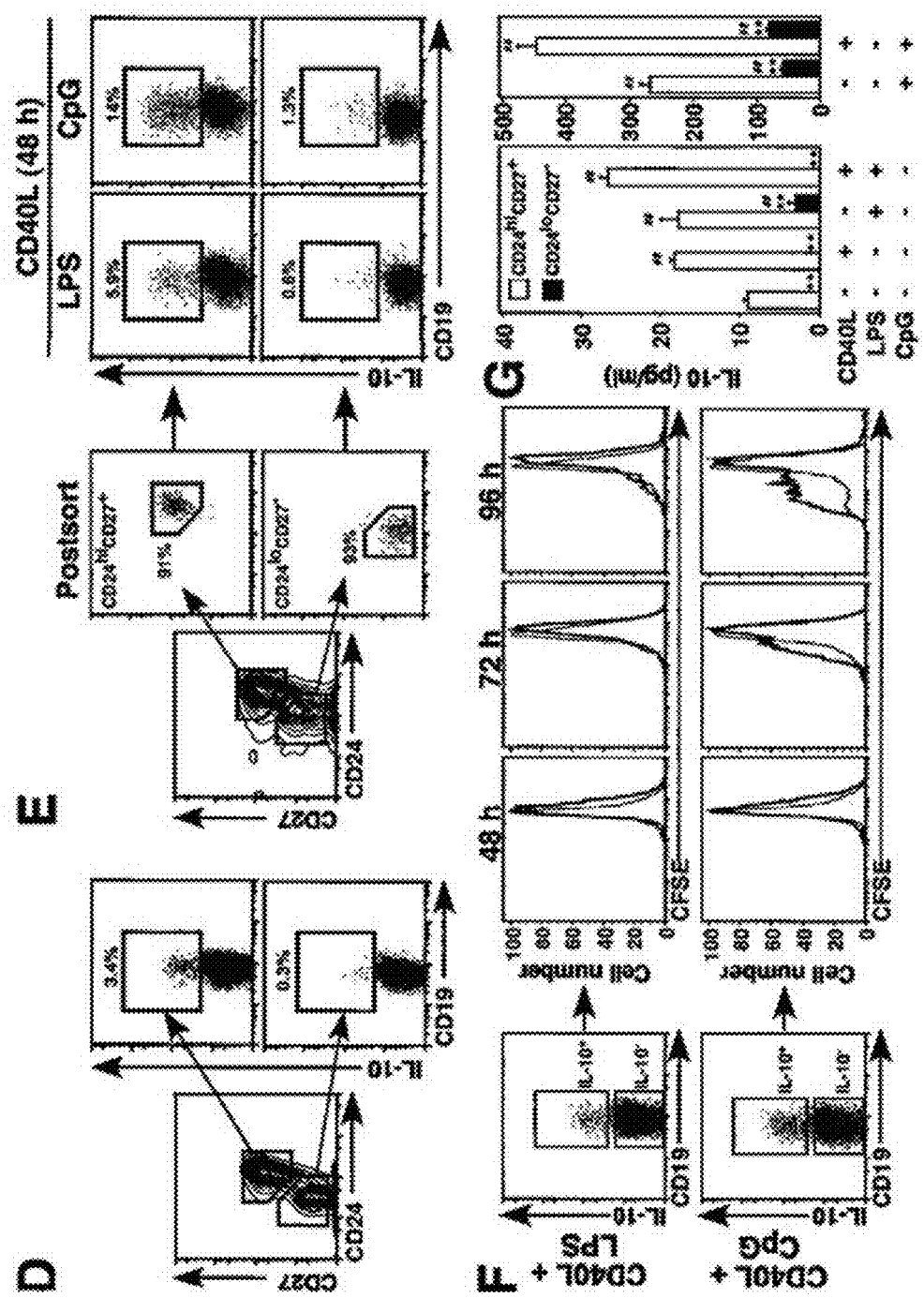

To determine whether B10 cells predominantly localize within the CD24$^{hi}$CD27⁺ subpopulation that represented 24±5% (n=7) of blood B cells, blood CD24$^{hi}$CD27⁺ and CD24$^{low}$CD27⁻ subpopulations were first purified and then cultured individually with L+PIB for 5 h to induce IL-10 expression (FIG. 6D). Following cell permeabilization and cytoplasmic IL-10 staining, B10 cell frequencies were at least 10-fold higher within the previously purified CD24$^{hi}$CD27⁺ subpopulation when compared with the isolated CD24$^{low}$CD27⁻ B cells. Thus, B10 cells were predominantly CD24$^{hi}$CD27⁺ in vivo.

To determine whether B10pro cells also predominantly localize within the CD24$^{hi}$CD27⁺ subpopulation, blood CD24$^{hi}$CD27⁺ and CD24$^{low}$CD27⁻ subpopulations were purified and then cultured individually with CD40L, and LPS or CpG for 48 h to induce B10pro cell maturation. Again, the frequency of B10 cells was 10-fold higher within the CD24$^{hi}$CD27⁺ subpopulation when compared with CD24$^{low}$CD27⁻ cells (FIG. 6E). To eliminate the possibility that B10pro cell proliferation during the 48 h cultures contributed to their expansion, the purified blood B cells were labeled with CFSE before in vitro stimulation. Regardless of whether the cells were stimulated with LPS or CpG, there was no B cell division until 72-96 h of culture. At this point, B10 cells exhibited a significant proliferative capacity, while IL-10⁻ B cells exhibited a modest proliferative capacity (FIG. 6F). Thus, the preferential localization of blood B10 and B10+B10pro cells within the CD24$^{hi}$CD27$^+$ B cell subpopulation was not due to cell proliferation during the 48 h culture period.

The capacity of freshly isolated CD24$^{hi}$CD27$^+$ and CD24$^{low}$CD27$^-$ B cells to secrete IL-10 was also assessed. CD40L, LPS, and LPS+CD40L stimulation for 72 h induced modestly increased IL-10 production by the CD24$^{hi}$CD27$^+$ population, but not CD24$^{low}$CD27$^-$ cells (FIG. 6G). CD24$^{hi}$CD27$^+$ cells secreted >10-fold more IL-10 in response to either CpG or CpG+CD40L stimulation when compared with LPS stimulation alone. IL-10 secretion by CD24$^{low}$CD27$^-$ B cells was 78% and 82% lower than for CD24$^{hi}$CD27$^+$ B cells in response to CpG and CpG+CD40L, respectively ($p<0.001$). Thus, blood B10 and B10+B10pro cells were predominantly a small subset of the CD24$^{hi}$CD27$^+$ B cell subpopulation.

7.2.7. B10 Cell Development in Patients with Autoimmune Disease

Figures 7A, 7B:
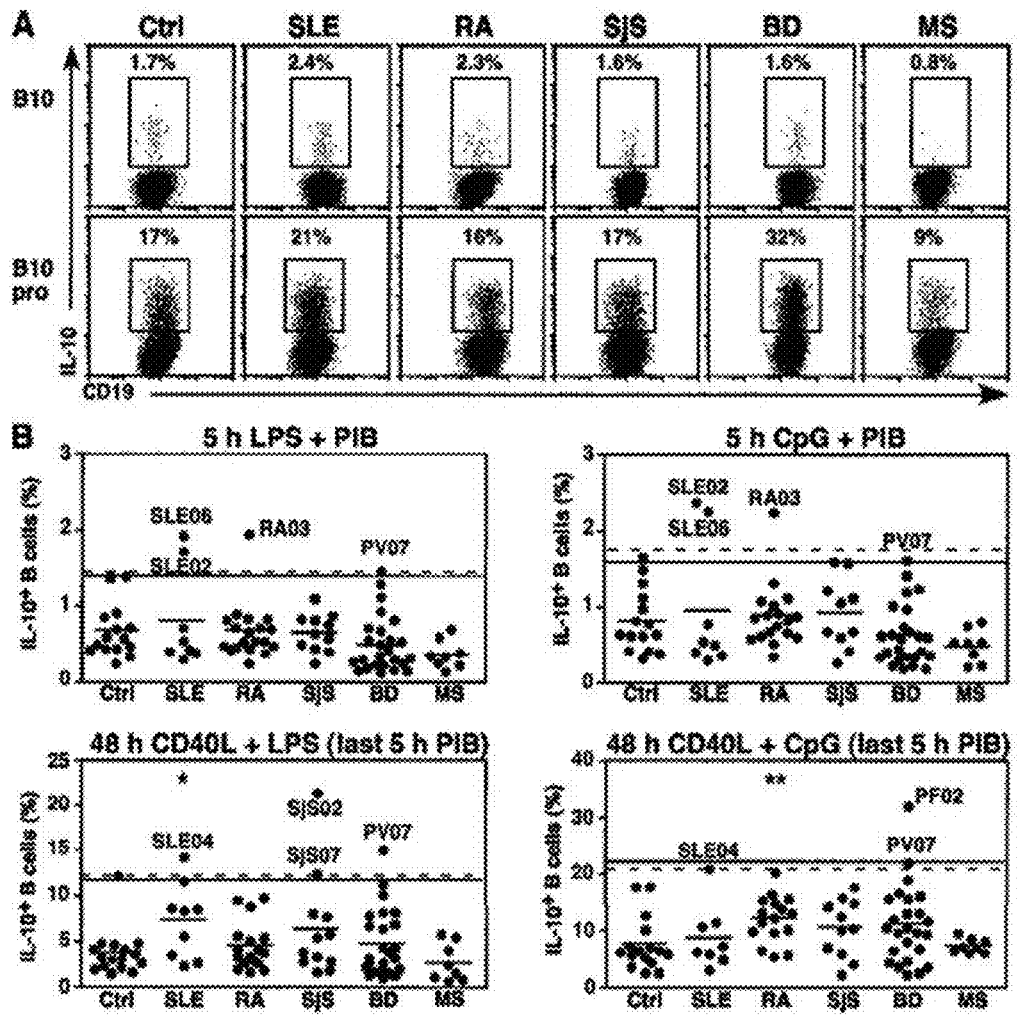
Figures 7C, 7D, 7E:
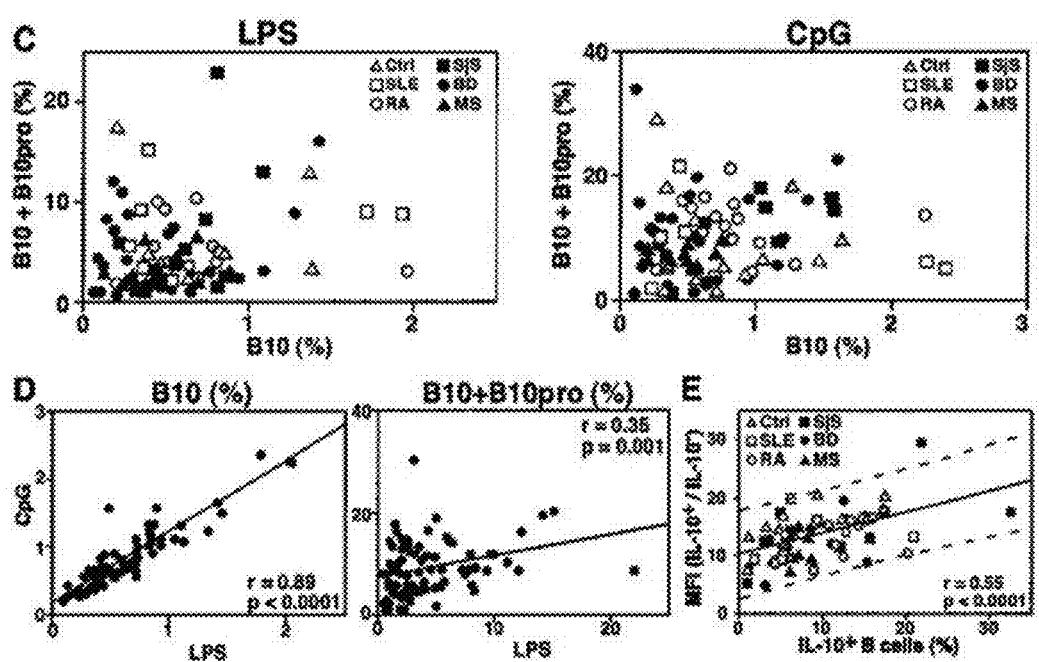

To determine whether blood B10 cell numbers are altered in patients with autoimmune disease, B10 and B10pro cells were examined in healthy controls, and fifty-two patients with SLE, RA, SjS, autoimmune BD, or MS. Most of the patients were undergoing active treatment with immune modulatory agents when the blood was taken (see Table 1, below). Nonetheless, some patients had high blood B10 cell frequencies even though there were no significant differences in mean B10 cell numbers between patient groups in comparison with controls (FIG. 7A-B). One BD patient that had not been given immunosuppressive therapy had blood B10 cell frequencies that were significantly higher than the population mean. Two SLE patients and one RA patient also had blood B10 cell frequencies that were significantly higher than the population mean, but retrospective evaluation of their disease status, autoantibody profile, and treatment regimen did not reveal obvious explanations for why these individuals had higher blood B10 frequencies than other patients. B10 cell frequencies were similar regardless of whether LPS or CPG were added to the PIB-stimulated cultures (FIG. 7D, left panel). No patient groups were identified that expressed significantly lower B10 cell frequencies relative to controls or other patient groups.

Mean B10+B10pro cell frequencies from patients with SLE and BD were significantly higher than controls following CD40L+LPS stimulation, while mean B10+B10pro cell numbers in RA patient's were significantly higher after CD40L+CpG stimulation when compared with the control group (FIG. 7B). Notably, patients with high blood B10 cell frequencies did not necessarily have high B10+B10pro cell frequencies after either LPS or CpG stimulation (FIG. 7C). While B10 cell frequencies were linearly correlated following either LPS or CPG stimulation, the scatter of the results obtained for B10+B10pro cells was broad, suggesting inherently different patient sensitivities to LPS and CpG stimulation (FIG. 7D). Likewise, B10 and B10+B10pro cell frequencies did not correlate with CD27$^+$ B cell frequencies. Regardless, relative B10 and B10+B10pro cell frequencies were significantly correlated with the intensity of cytoplasmic IL-10 expression (FIG. 7E). One patient among the entire group appeared to generate significantly higher ($p<0.05$) cytoplasmic IL-10 expression levels on a per cell basis relative to controls and other patients.

TABLE 1

Patient characteristics.

| Diagnosis Number | Sex | Age | Disease Duration (y) | Autoantibody/Clinical Status | Immunosuppressive Therapy |
|---|---|---|---|---|---|
| RA011 | M | 54 | 11 | RF = 600 IU/ml; anti-CCP = 68.5 U/ml | MTX, ADA, Pred 5 mg/d |
| RA02 | F | 44 | 4 | RF = 352 IU/ml; anti-CCP > 100 U/ml | MTX |
| RA03 | F | 54 | 14 | RF = 146 IU/mL | MTX, LEF |
| RA04 | F | 85 | 18 | RF = neg | MTX, IFX |
| RA05 | M | 69 | 19 | RF = 208 IU/ml; anti-CCP > 100 U/ml | MTX, Pred 5 mg/d |
| RA06 | F | 71 | 8 | RF = neg | MTX |
| RA07 | F | 67 | 13 | RF = 333 IU/ml | ETN |
| RA08 | F | 58 | 25 | RF = 53 IU/ml | MIX, ETN, Pred 3 mg/d |
| RA09 | F | 68 | 7 | RF = 339 IU/ml | MTX, Prod 3 mg/d |
| RA10 | M | 75 | 13 | RF = 420 IU/ml; anti-CCP = 18.9 U/ml | MTX, LEF, Pred 10 mg/d |
| RA11 | F | 73 | 7 | RF and anti-CCP =neg | MTX, LEF |
| RA12 | M | 61 | 27 | RF = 107 IU/ml | MTX, LEF |
| RA13 | F | 66 | 6 | RF = pos | ADA |
| RA14 | F | 84 | 11 | RF = 275 IU/ml; anti-CCP = 28 U/ml | ETN |
| RA15 | F | 52 | 3 | RF = neg; anti-CCP > 100 U/ml | ETN |
| RA16 | F | 76 | 18 | RF = pos | MIX |
| RA17 | M | 63 | 11 | RF = neg; anti-CCP > 100 U/ml | MTX, SSZ, Pred 1 mg/d |
| RA18 | F | 43 | 15 | RF = U/ml | MTX, IFX |
| RA19 | F | 62 | 30 | RF = 148 IU/ml; anti-CCP > 100 U/ml | LEF; Pred 5 mg/d |
| SLE01 | F | 65 | 11 | ANA = 1:2560; IgG CL and anti-dsDNA = pos | HCQ, LEF, Pred 5 mg/d |
| SLE02 | M | 31 | 3 | ANA = 1:640; anti-RNP, anti-Sm, and anti-Ro = pos | HCQ, Pred 3 mg/d |
| SLE03 | M | 63 | 32 | ANA = 1:640; anti-dsDNA and IgG anti-CL = pos | HCQ, Pred 5 mg/d |
| SLE04 | F | 37 | 5 | ANA = 1:2560; anti-Ro = pos | None |
| SLE05 | F | 43 | 15 | ANA = 1:160; RF = IU/ml | HCQ, MMF |
| SLE06 | F | 46 | 8 | ANA = pos; anti-Ro = pos | MMF 2 g/d, Pred 10 mg/d |
| SLE07 | M | 31 | 23 | ANA = 1:160; anti-dsDNA and IgG anti-CL = pos | HCQ |
| SLE08 | F | 47 | 10 | ANA = 1:2560; anti-dsDNA, anti-Ro and anti-La = pos; RF = 103 IU/ml | None |
| SLE09 | F | 37 | 16 | ANA = pos; anti-dsDNA, anti-IgM and IgG CL = pos | HCQ; Pred 10 mg/d |
| SjS01 | F | 52 | 1 | ANA = 1:2560; RF = IU/ml; anti-Ro and anti-La = pos | None |
| SjS02 | F | 65 | 15 | ANA = 1:2560; RF = 22 IU/ml; anti-Ro = pos | HCQ |
| SjS03 | F | 57 | 37 | ANA = 1:160; anti-Ro = pos | MMF, Pred 40 mg/d |
| SjS04 | F | 67 | 22 | ANA = 1:2560; RF 110 IU/ml, anti-Ro and anti-Lagos | HCQ |
| SjS05 | F | 60 | 9 | ANA = 1:2560; RF = 126 IU/ml, anti-Ro = pos | HCQ |

TABLE 1-continued

Patient characteristics.

| Diagnosis Number | Sex | Age | Disease Duration (y) | Autoantibody/Clinical Status | Immunosuppressive Therapy |
|---|---|---|---|---|---|
| SjS06 | F | 58 | 21 | ANA = 1:2560; anti-Ro and anti-La = pos | None |
| SjS07 | F | 41 | 13 | ANA = 1:2560; anti-Ro and anti-Lagos | HCQ |
| SjS08 | F | 59 | 8 | ANA = 1:2560; RF = 508 IU/ml; anti-Ro = pos | None |
| SjS09 | F | 42 | 4 | ANA = 1:2560; RF = 110 IU/ml; anti-Ro and anti-La = pos | HCQ |
| SjS10 | F | 58 | 5 | ANA = 1:2560; anti-Ito and anti-La = pos | HCQ, Pred 3 mg/d |
| SjS11 | M | 66 | 5 | ANA = 1:2560; anti-Ro and anti-Lagos | None |
| SjS12-46 | F | 76 | 13 | ANA = 1:2560; anti-Ro = pos; RF = 32 IU/ml | None |
| BP01 | M | 72 | 0.3 | Anti-BP180 = 84 U/ml; anti-BP230 = 115 U/ml, no clinical disease | Pred 60 mg/d |
| BP02 | M | 54 | 1.2 | Anti-BP180 = 72 U/ml; anti-BP230 = neg, no clinical disease | MMF, Pred 12 mg/d |
| BP03 | F | 56 | 2 | Anti-BP180 = 51 U/ml; anti-BP230 = neg, no clinical disease | Pred 20 mg/d |
| BP04 | M | 75 | 4.3 | Anti-BP180 = 45 U/ml; anti-BP230 = 3, minimal disease | None |
| BP05 | F | 66 | 1.8 | Anti-BP180 = 96 U/ml; anti-BP230 = 131, severe disease | None |
| BP06 | M | 77 | 0.5 | Anti-BP180 = 5 U/ml; anti-BP230 = 95, minimal disease | None |
| BP07 | F | 67 | 17 | Anti-BP180 = 46 U/ml; anti-BP230 = neg, trace disease | RTX (20 mos earlier) |
| PF01 | M | 54 | 8.6 | Anti-DSG1 = 134 U/ml; anti-DSG3 = neg, minimal disease activity | AZA |
| PF02 | M | 55 | 9.8 | Anti-DSG1 = neg; anti-DSG3 = neg, minimal disease activity | RTX (30 mos earlier) |
| PF03 | M | 46 | 6.6 | Anti-DSG1 = neg; anti-DSG3 = neg, minimal disease activity | None |
| PF04 | M | 50 | 5.3 | Anti-DSG1 = neg; anti-DSG3 = neg, minimal disease activity | Cellcept 3 g/d |
| PF05 | M | 72 | 2.8 | Anti-DSG1 = neg; anti-DSG3 = neg, no clinical disease | Dapsone 100 mg/d |
| PV01 | M | 47 | 2.6 | Anti-DSG1 = 24 U/ml; anti-DSG3 = 5171 U/ml, mild disease | AZA |
| PV02 | M | 43 | 3 | Anti-DSG1 = neg; anti-DSG3 = 213 U/ml, mild disease | MMF, Pred 20 mg/d |
| PV03 | M | 73 | 3.3 | Anti-DSG1 = neg; anti-DSG3 = 948 U/ml, mild disease | Pred 12 mg/d |
| PV04 | F | 55 | 4.7 | Anti-DSG1 = neg; anti-DSG3 = 406 U/ml, mild disease | RTX (15 mos earlier) |
| PV05 | M | 59 | 8.3 | Anti-DSG1 = neg; anti-DSG3 = 50 U/ml, no disease activity | AZA |
| PV06 | F | 48 | 8.6 | Anti-DSG1 = neg; anti-DSG3 = 25 U/ml, no disease activity | None |
| PV07 | M | 45 | 0.25 | Anti-DSG1 = 968; anti-DSG3 = 735, severe disease, ~20% body surface area involving ulcerations and erosions | MMF; Pred 80 mg/d |
| PV08 | M | 84 | 0.2 | Anti-DSG1 = 75; anti-DSG3 = 146 U/ml, moderate disease | None |
| PV09 | M | 64 | 9.8 | Anti-DSG1 = 14; anti-DSG3 = 115 U/ml, minimal disease activity | Pred 20 mg/d; IFX |
| PV10 | M | 59 | 3.8 | Anti-DSG1 = 1; anti-DSG3 = 49 U/ml, no disease activity | AZA |
| PV11 | M | 55 | 6 | Anti-DSG1 = 34; anti-DSG3 = 35 U/ml, minimal disease activity | Pred 20 mg/d; MMF 1000 mg/d |
| PV12 | F | 58 | 9.5 | Anti-DSG1 = 1; anti-DSG3 = 43 U/ml, trace disease | AZA |
| MS01 | F | 72 | 54 | SPMS, EDSS 6.5, not clinically active | None |
| MS02 | M | 62 | 24 | RRMS, EDSS 6.5, clinically active | BIFN |
| MS03 | M | 33 | 2 | RRMS, EDSS 1.0, disease not clinically active | BIFN |
| MS04 | M | 75 | 29 | SPMS, EDSS 8.0, disease not clinically active | ITMTX |
| MS05 | M | 52 | 24 | PPMS, EDSS 6.5, disease clinically active | MMF, pulse steroids |
| MS06 | M | 55 | 25 | PPMS, EDSS 7.5, disease clinically active | ITMTX |
| MS07 | F | 39 | 16 | SPMS, EDSS 7.0, disease not clinically active | Natalizumab (2 mos prior) |
| MS08 | F | 51 | 7 | SPMS, EDSS 5.5, disease not clinically active | BIFN |

[1]Abbreviations: ANA, antinuclear Ab; ADA, adalimumab; AZA, azathioprine; BIFN, beta interferon; BP, bullous pemphigoid; CCP, cyclic citrullinated peptide; CL, cardiolipin; DH, dermatitis herpetiformis; dsDNA, double stranded DNA; DSG, desmoglein; EDSS, disability scale from 0 = normal to 10 = death; ETN, etanercept; HCQ, hydroxychloroquine; IFX, infliximab; ITMTX, intrathecal methotrexate; LEF, leflunomide; MMF, mycophenolate mofetil; MTX, methotrexate; PF, pemphigus foliaceus; PPMS, primary progressive multiple sclerosis; Pred, Prednisone; PV, pemphigus vulgaris; RA, rheumatoid arthritis; RF, rheumatoid factor; RRMS, relapsing remitting multiple sclerosis; RTX, rituximab; SjS, primary Sjögren's syndrome; SLE, lupus; SPMS, secondary progressive multiple sclerosis; SSZ, sulfasalazine; y, year.
[2]Normal values: anti-BP = 180, anti-BP = 230, anti-DSG1 and anti-DSG3 antibodies <9 IU/ml.

7.3 Discussion

This example demonstrates the existence of human IL-10-competent B10 cells, which were readily identified by their ability to express cytoplasmic IL-10 after appropriate in vitro stimulation. Peripheral blood B10 cell frequencies were characteristically low (0.6%) in most individuals, consistent with their low frequencies in mice. Human B10pro cells were also identified by their ability to express IL-10 after in vitro maturation. Remarkably, the adaptive and innate activation pathways that induced human B10 and B10pro cell generation, maturation, cytoplasmic IL-10 expression, and IL-10 secretion were similar to those used by mouse regulatory B10 cells. Human B10 cell frequencies were also similar in the blood, spleen, and lymph nodes (FIG. 2-3).

In this example, B10 cells were defined by their IL-10 production using optimized stimulation conditions similar to those that have defined mouse B10 and B10pro cells. IL-10-competence remains the best phenotypic marker for defining human B10 cells. However, freshly isolated blood B10 and B10pro cells were also predominantly $CD24^{hi}CD27^+$, with ~60% also expressing CD38 at high levels (FIG. 6A, C). B10 cells were also predominantly $CD48^{hi}$ and $CD148^{hi}$ (FIG. 6A). CD148 is considered a marker for human splenic memory B cells (see Tangye et al., 1988, J. Exp. Med. 188:1691-1703) and CD48 is upregulated on activated B cells (see Yokoyama et al., 1991, J. Immunol. 146:2192-2200). By contrast, most $CD24^{lo}CD27^-$ B cells were not IL-10 competent, even after 48 h of LPS or CpG stimulation along with agonistic CD40 ligation. CD27 expression is a well-characterized marker for memory B cells, although some memory B cells may be CD27⁻ (see Sanz et al., 2008, *Sem. Immunol.* 20:67-82; Klein et al., 1998, *J. Exp. Med.* 188:1679-1689; and Agematsu et al., 2000, *Immunol. Today* 21:204-206). The CD27⁺ B cell subpopulation can also expand during the course of autoimmunity and may serve as a marker for disease activity (see Sanz et al., 2008, *Sem. Immunol.* 20:67-82; and Agematsu et al., 2000, *Immunol. Today* 21:204-206). However, B10 cell frequencies did not parallel the size of the CD27⁺ memory B cell pool in the blood of normal donors or in patients with autoimmune diseases, suggesting that these two subsets may be regulated independently. Thus, the CD24$^{hi}$CD27⁺ phenotype of B10 and B10pro cells indicates that they may either be selected into the memory B cell pool during their development or B10 and B10pro cells represent a distinct B cell subset that shares common cell surface markers with memory B cells. However, consistent with their memory phenotype, the proliferative capacity of blood B10 cells in response to mitogen stimulation was higher than that for other B cells (FIG. 6F), as is also seen in mice (see Yanaba et al., 2009, *J. Immunol.* 182:7459-7472). Human transitional B cells are also rare (2-3% of B cells) in adult blood, and are generally CD10⁺CD24$^{hi}$CD38$^{hi}$ cells that are IgD⁺ CD27⁻ (see Sims et al., 2005, *Blood* 105:4390-4398; and Cuss et al., 2006, *J. Immunol.* 176:1506-1516). Given that CD10 expression is a well-accepted marker for most cells within the transitional B cell pool (see Wardemann et al, 2003, *Science* 301:1374-1377), its absence on B10 cells suggests that these cells are not recent emigrants from the bone marrow. Thereby, IL-10 competence and elevated proliferative responses characterize the human blood B10 cell subset, with most blood B10 cells expressing a CD24$^{hi}$CD27⁺ phenotype.

While a small subset of blood B cells was inherently competent to express IL-10, a subset of blood B cells also had the capacity to acquire IL-10 competence following stimulation with LPS, CpG, and other TLR agonists (FIGS. 2D and G). Combining TLR stimulation with prolonged CD40 stimulation facilitated the acquisition of IL-10 competence. Since IL-10 is critical for B cell regulatory activity in mice, the current studies demonstrate that B10 cells in normal individuals and autoimmune disease patients are functionally competent to express IL-10 (FIG. 7A-B).

Mean blood B10 cell frequencies in most patients with SLE, RA, SjS, autoimmune BD, and MS were not significantly different from those observed in normal controls (FIG. 7B). However, four patients did have significantly higher B10 or B10+B10pro cell frequencies, including two SLE patients. This also included one PV patient (PV07) with severe disease involving 20% of the skin (Table 1). Significantly increased B10+B10pro cell frequencies were also found in an untreated SLE patient (SLE04). Interestingly, one patient previously treated with rituximab had elevated B10+B10pro cell frequencies (PF02). Thus, some patients may have elevated B10/B10pro cell frequencies as found in some autoimmune prone mouse strains (see Haas et al., 2010, *J. Immunol.* (in press); and Yanaba et al., 2009, *J. Immunol.* 182:7459-7472) and during inflammation (see Yanaba et al., 2008, *Immunity* 28:639-650; and Matsushita et al., 2008, *J. Clin. Invest.* 118:3420-3430).

The current assessment of B10 and B10+B10pro cell frequencies in patients provides a context for previous studies, where spontaneous IL-10 production by resting blood B cells is reported to be dramatically higher in untreated patients with RA, SLE, and systemic sclerosis than in controls, as measured by RT-PCR and ELISA assays (see Llorente et al., 1994, *Arthritis & Rheumatism* 37:1647-1655). More recently, B cell cytoplasmic IL-10 production by blood mononuclear cells has been examined in patients with SLE compared with normal controls after 24 h in culture with or without PMA plus ionomycin, or LPS (see Amel Kashipaz et al., 2003, *Lupus* 12:356-363). In that study, significantly more SLE B cells spontaneously produced cytoplasmic IL-10 (1.1%) than controls (0.6%). However, after stimulation by PMA plus ionomycin, the number of IL-10⁺ B cells was no higher in the SLE patients (1.3%) when compared with the unstimulated cultures, but was slightly higher in the controls (1.5%). By contrast, LPS stimulation failed in either case to increase intracellular IL-10-producing B cell frequencies in comparison with unstimulated cells. Furthermore, unstimulated and stimulated CD5⁺ B cells from SLE patients were enriched for cells producing high levels of IL-10, although stimulation of CD5⁺ B cells from normal controls induced more IL-10 production than stimulation of CD5⁺ cells from normal controls. In other studies, 26% of SLE patients' blood B cells spontaneously expressed cytoplasmic IL-10, while 50% were IL-10⁺ after mitogen activation (see Diaz-Alderete et al., 2004, *J. Autoimmun.* 23:379-383). In this case, IL-10 expression was confined to a CD154⁺ (CD40L⁺) subset of B cells, but not to CD5⁺ B cells.

Various publications are cited herein, the disclosures of which are incorporated by reference in their entireties.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

---

We claim:

1. A method comprising: (i) selecting B lymphocytes in a sample from a human or mouse; (ii) contacting and selecting the B lymphocytes with an anti-CD24 antibody to select for CD24$^{high}$ B cells; (iii) contacting and selecting the B lymphocytes with an anti-CD27 antibody to select for CD27+ B cells; and (iv) stimulating the selected CD24$^{high}$ CD27$^+$ B cells in vitro with PMA (phorbol 12-myristate 13-acetate) and ionomycin to generate B10 cells.

2. The method of claim 1, further comprising (v) selecting for B10 cells.

3. The method of claim 1, further comprising selecting the CD24$^{high}$ CD27$^+$ B cells positive for at least one of CD19, CD20, CD21, CD22, CD38, CD40, CD48, CD72, or CD148.

4. The method of claim 2, further comprising stimulating the CD24$^{high}$ CD27$^+$ B cells with a CD40 agonist or a TLR agonist prior to selecting for B10 cells.

5. The method of claim 1, wherein the CD24$^{high}$ CD27$^+$ B cells in step (iv) are stimulated for at least 5 hours.

6. The method of claim 1, further comprising contacting the CD24$^{high}$ CD27$^+$ B cells with a growth stimulatory composition.

7. The method of claim 6, wherein the growth stimulatory composition comprises at least one of a mitogen, a cytokine, a growth factor, an antibody, a CD40 agonist or a TLR agonist.

8. The method of claim 1, wherein step (ii) is performed prior to or simultaneously with step (iii).

* * * * *